(12) United States Patent
Prausnitz et al.

(10) Patent No.: US 11,730,937 B2
(45) Date of Patent: Aug. 22, 2023

(54) SEPARABLE MICRONEEDLE ARRAYS FOR SUSTAINED RELEASE OF DRUG

(71) Applicant: Georgia Tech Research Corporation, Atlanta, GA (US)

(72) Inventors: Mark R. Prausnitz, Atlanta, GA (US); Richard N. Terry, Conyers, GA (US); Wei Li, Atlanta, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 378 days.

(21) Appl. No.: 16/755,449

(22) PCT Filed: Oct. 11, 2018

(86) PCT No.: PCT/US2018/055519
§ 371 (c)(1),
(2) Date: Apr. 10, 2020

(87) PCT Pub. No.: WO2019/075275
PCT Pub. Date: Apr. 18, 2019

(65) Prior Publication Data
US 2020/0238065 A1 Jul. 30, 2020

Related U.S. Application Data

(60) Provisional application No. 62/713,857, filed on Aug. 2, 2018, provisional application No. 62/571,012, filed on Oct. 11, 2017.

(51) Int. Cl.
*A61M 37/00* (2006.01)
*A61K 9/46* (2006.01)
(Continued)

(52) U.S. Cl.
CPC ....... *A61M 37/0015* (2013.01); *A61K 9/0007* (2013.01); *A61K 9/0024* (2013.01);
(Continued)

(58) Field of Classification Search
CPC ...... A61M 37/0015; A61M 2037/0023; A61M 2037/0046; A61M 2037/0053;
(Continued)

(56) References Cited

U.S. PATENT DOCUMENTS 6,503,231 B1 1/2003 Prausnitz et al.
8,075,826 B2 12/2011 Lastovich et al.
(Continued)

FOREIGN PATENT DOCUMENTS

CN 104069585 A 10/2014
JP 2010233674 A 10/2010
(Continued)

OTHER PUBLICATIONS

Written Opinion of the International Searching Authority, dated Jan. 7, 2019, for PCT/US2018/055519.
(Continued)

*Primary Examiner* — Amber R Stiles
(74) *Attorney, Agent, or Firm* — Eversheds Sutherland (US) LLP

(57) ABSTRACT

Separable microneedle arrays and microneedle patches are provided that may achieve sustained release of drug. The microneedle arrays may include one or more features that facilitate separation of the microneedles, such as a bubble structure. The microneedle arrays may include an effervescent material.

34 Claims, 19 Drawing Sheets

(51) Int. Cl.
*A61K 9/00* (2006.01)
*A61K 31/57* (2006.01)

(52) U.S. Cl.
CPC ..... *A61K 31/57* (2013.01); *A61M 2037/0023* (2013.01); *A61M 2037/0046* (2013.01); *A61M 2037/0053* (2013.01); *A61M 2037/0061* (2013.01)

(58) Field of Classification Search
CPC ......... A61M 2037/0061; A61K 9/0007; A61K 9/0024; A61K 31/57
See application file for complete search history.

(56) References Cited

U.S. PATENT DOCUMENTS

| | | | |
|---|---|---|---|
| 8,708,966 | B2 | 4/2014 | Allen et al. |
| 9,549,746 | B2 | 1/2017 | Woolfson et al. |
| 9,848,853 | B2 | 12/2017 | Mitragotri et al. |
| 10,265,511 | B2 | 4/2019 | McAllister et al. |
| 2002/0082543 | A1 | 6/2002 | Park et al. |
| 2004/0106904 | A1 | 6/2004 | Gonnelli et al. |
| 2005/0065463 | A1 | 3/2005 | Tobinaga et al. |
| 2005/0137525 | A1 | 6/2005 | Wang et al. |
| 2005/0137531 | A1 | 6/2005 | Prausnitz et al. |
| 2007/0078414 | A1 | 4/2007 | McAllister et al. |
| 2007/0225676 | A1 | 9/2007 | Prausnitz et al. |
| 2007/0260201 | A1 | 11/2007 | Prausnitz et al. |
| 2008/0009825 | A1 | 1/2008 | Ringsred et al. |
| 2008/0167601 | A1 | 7/2008 | Laermer et al. |
| 2008/0213461 | A1 | 9/2008 | Gill et al. |
| 2008/0269666 | A1 | 10/2008 | Wang et al. |
| 2009/0041810 | A1 | 2/2009 | Andrianov et al. |
| 2009/0118672 | A1 | 5/2009 | Gonnelli et al. |
| 2009/0131905 | A1 | 5/2009 | Allen et al. |
| 2009/0182306 | A1 | 7/2009 | Lee et al. |
| 2009/0187160 | A1 | 7/2009 | McAllister et al. |
| 2012/0226260 | A1 | 9/2012 | Prausnitz et al. |
| 2013/0165902 | A1 | 6/2013 | Stumber et al. |
| 2013/0338596 | A1 | 12/2013 | McAllister |
| 2013/0338597 | A1 | 12/2013 | McAllister |
| 2014/0005606 | A1 | 1/2014 | Chen et al. |
| 2014/0180201 | A1 | 6/2014 | Ding et al. |
| 2014/0236089 | A1 | 8/2014 | Brouwers et al. |
| 2014/0316333 | A1* | 10/2014 | Kwon ................. A61K 31/137 424/443 |
| 2015/0209180 | A1 | 7/2015 | Prausnitz et al. |
| 2016/0001053 | A1* | 1/2016 | Quan ................ A61M 37/0015 427/2.31 |
| 2016/0101272 | A1 | 4/2016 | McAllister |
| 2016/0107189 | A1 | 4/2016 | Hashimoto et al. |
| 2016/0213908 | A1 | 7/2016 | McAllister et al. |
| 2017/0036003 | A1* | 2/2017 | Wakamatsu .......... A61M 37/00 |
| 2017/0050010 | A1* | 2/2017 | Mcallister .............. B33Y 80/00 |
| 2017/0252546 | A1 | 9/2017 | Park et al. |
| 2017/0273827 | A1 | 9/2017 | Prausnitz et al. |
| 2018/0078498 | A1 | 3/2018 | Petersson et al. |
| 2018/0133447 | A1 | 5/2018 | McAllister et al. |
| 2019/0001108 | A1 | 1/2019 | Ono |
| 2019/0015651 | A1 | 1/2019 | Tadros et al. |
| 2019/0358441 | A1* | 11/2019 | Zvezdin ............... A61K 9/0021 |

FOREIGN PATENT DOCUMENTS

| | | |
|---|---|---|
| JP | 2017164191 A | 9/2017 |
| WO | 2008053481 A1 | 5/2008 |

OTHER PUBLICATIONS

Li, et al., "Rapidly Separable Microneedle Patches for Sustained Release of Contraceptive Hormones," Abstract published by Biomedical Engineering Society, Apr. 24, 2017 (1 page).

Chu, et al., "Fabrication of Dissolving Polymer Microneedles for Controlled Drug Encapsulation and Delivery: Bubble and Pedestal Microneedle Designs," J. Pharmaceutical Sciences, 99(10): 4228-38 (Oct. 2010).

Wang, et al. "Microneedles with Controlled Bubble Sizes and Drug Distributions for Efficient Transdermal Drug Delivery," Scientific Reports, 6:38755, DOI:10.1038/srep38755 (Dec. 2016).

First Office Action issued in China application No. 201880079792.2, dated Feb. 10, 2023, 21 pages.

* cited by examiner

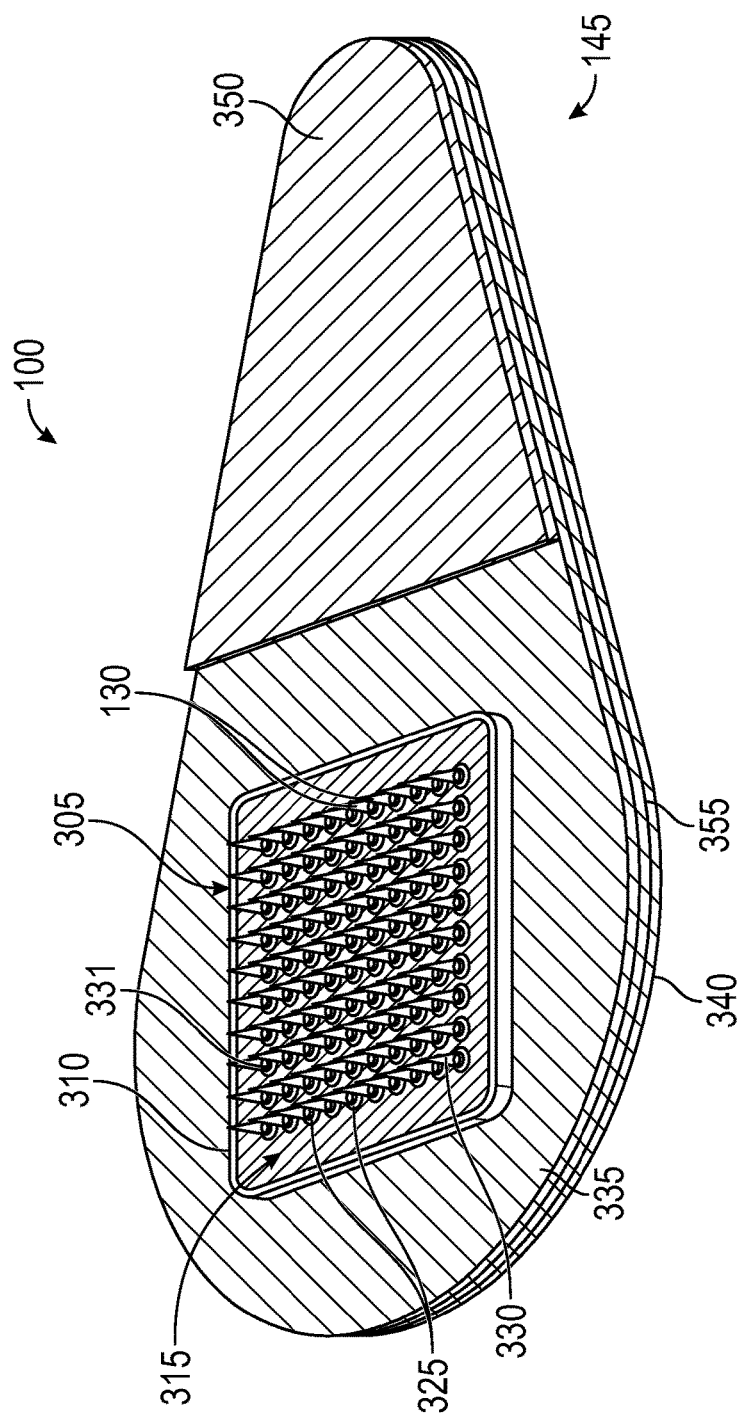
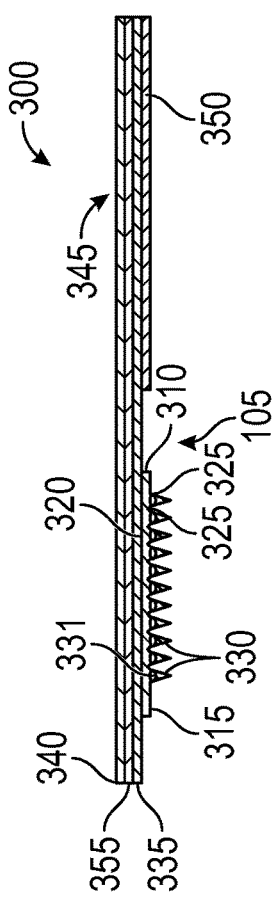
FIG. 3A
FIG. 3B

SEPARABLE MICRONEEDLE ARRAYS FOR SUSTAINED RELEASE OF DRUG

CROSS-REFERENCE TO RELATED APPLICATIONS

This application claims priority to U.S. Provisional Patent Application No. 62/571,012, filed Oct. 11, 2017, and U.S. Provisional Patent Application No. 62/713,857, filed Aug. 2, 2018, which are incorporated herein by reference.

STATEMENT REGARDING FEDERALLY SPONSORED RESEARCH

This invention was made with Government support under Contract Number AID-OAA-A-15-00045 awarded by the United States Agency for International Development. The Government has certain rights in the invention.

BACKGROUND

Microneedles are micron-scale structures that can administer drugs in a minimally invasive manner. Microneedles have been used for the bolus delivery of drugs and vaccines using either coated or water-soluble microneedles. A previous study reported the use of dissolvable microneedles for delivery of levonorgestrel (LNG) for emergency contraception (Yao, G. T. et al., Int. J. Pharm. 534, 378-86 (2017)). The patches were worn for up to two hours and did not provide sustained drug release.

Despite advances in contraceptive methods, the percentage of pregnancies that are unintended remains significant. The high number of unintended pregnancies can cause economic and emotional burden to women and society at large. One of, if not the, primary reason for unintended pregnancy is a lack of contraceptive methods that meet the needs of diverse populations of women at various stages of their reproductive life cycle.

Non-hormonal contraceptive methods, such as condoms and diaphragms, provide physical barriers for pregnancy protection, but these barrier methods, even when accompanied by spermicide, usually have an relatively high failure rate, typically due to poor patient acceptance and compliance with correct use guidelines. Hormonal contraceptives, such as oral pills, vaginal rings, intrauterine devices, subdermal injections and implants, generally provide better protection, but either require frequent dosing, which typically results in significant compliance problems, or delivery by healthcare professionals, which can be especially problematic in low-income countries.

A number of different contraceptive hormones are safe, effective, and low-cost. Some contraceptives are long-acting because of sustained-release formulations, but options for self-administration are limited. A well-established method of sustained release involves encapsulating drug in biodegradable polymers, which slowly release drug by drug diffusion and/or polymer degradation. This approach is utilized in many pharmaceutical products, and have been investigated as injectable or depot formulations for birth control. However, these formulations typically require administration by trained personnel, thereby limiting patient access. Moreover, the safety of these methods can be hampered by needle re-use and needle-based injuries.

There has been prior research on the incorporation of bubbles into microneedle patches to provide a barrier between the microneedle and the rest of the patch, in order to prevent migration of materials from the microneedle into the rest of the patch, and vice versa (see, e.g., Chu, L. Y. et al., J. Pharm. Sci. 2010, 99(10), 4228-38). The bubble-containing microneedles, however, were not configured to separate from the patches.

Therefore, there remains a need for drug delivery methods and devices, including contraceptive delivery methods and devices, that are safe, are effective, can allow sustained release, are capable of facilitating good patient access and compliance through self-administration, are relatively inexpensive and, therefore, suitable for use globally, or a combination thereof.

It also be would be desirable, in some cases, to provide drug delivery systems and methods in which no components of the system remain outside of the patient's body, for example, during a period of extended drug release of days, weeks, or months. For example, wearable drug delivery systems, e.g., skin adherent patches, are known in the art, but undesirably may not be easily concealed and/or may be uncomfortable to the patient having to wear the system for an extended period.

BRIEF SUMMARY

Provided herein are microneedle arrays having separable microneedles that can address one or more of the foregoing disadvantages. For example, the separable microneedle patches can overcome one or more of the disadvantages of current birth control methods by achieving a sustained-release of drug, such as a contraceptive hormone. The separable microneedle patches advantageously obviate injections of sustained-release formulations by conventional needle-and-syringe methods. Instead, a separable microneedle patch, as described herein, may be briefly and painlessly applied to skin to break off embedded biodegradable microneedles in the skin for slow-release of a drug, such as a contraceptive hormone.

The microneedle arrays described herein may include a feature, such as an internal air bubble or an effervescent material, which facilitates the separation of the microneedles from the devices after insertion in the skin, after which the remaining portion of the device may be removed and discarded. The remaining portion of the device may be non-sharps waste. The detached microneedles may biodegrade in the skin for a sustained release and systemic delivery of a substance of interest.

In one aspect, microneedle arrays are provided, which may be used to administer a substance of interest into a biological tissue, such as a patient's skin. The microneedle arrays may release the substance of interest for a sustained period of at least 2 weeks.

In some embodiments, the microneedle array for administering a substance of interest into a patient's biological tissue includes: a base substrate having a microneedle side and an opposing back side; and two or more solid microneedles extending from the base substrate, wherein at least a tip end portion of each microneedle comprises a substance of interest, wherein a bubble structure is disposed, at least partially, in each of the two or more solid microneedles, and the two or more solid microneedles are configured to penetrate into the patient's biological tissue under compression and then to fracture at the bubble structure, e.g., by a shear force applied to the array. A primary funnel portion may be disposed between and connect the base substrate and the microneedles. The bubble structure may be at least partially included in the primary funnel portion. For example, the bubble structure may be disposed at an interface of the base substrate (or the primary funnel portion, if present) and a base end of each microneedle.

In some embodiments, the microneedle array for administering a substance of interest into a patient's biological tissue includes: a base substrate having a microneedle side and an opposing back side; a primary funnel portion extending from the microneedle side of the base substrate; and two or more solid microneedles extending from the primary funnel portion, wherein at least a tip end portion of each microneedle comprises a substance of interest, wherein a bubble structure is disposed at an interface of the primary funnel portion and a base end of each microneedle, and the two or more solid microneedles are configured to penetrate into the patient's biological tissue under compression and then to separate from the primary funnel portion under shear, by fracture at the bubble structure.

In some embodiments, the microneedle arrays include a base substrate having a microneedle side and an opposing back side; at least one primary funnel portion extending from the microneedle side of the base substrate; and two or more solid microneedles extending from the at least one primary funnel portion, wherein the two or more solid microneedles include a substance of interest and a secondary funnel portion extending from the at least one primary funnel. The two or more solid microneedles may be constructed to penetrate into the patient's skin under compression and then to separate from the secondary funnel portions under shear following the penetration. The two or more solid microneedles may include a bubble structure at or near a base end of each microneedle, and the bubble structures may facilitate the separation of the microneedles from the secondary funnel portions. The bubble structures may be located at each interface of the two or more microneedles and the secondary funnel portions. In some embodiments, the substance of interest is a therapeutic or prophylactic agent, such as a contraceptive hormone.

In some embodiments, the microneedle arrays include a base substrate having a microneedle side and an opposing back side, and two or more solid microneedles extending from the base substrate, wherein at least a tip end portion of each microneedle includes a substance of interest, and an effervescent material is disposed in a portion of each of the two or more solid microneedles, at least a portion of the base substrate, or a combination thereof. The two or more solid microneedles may be configured to penetrate into a patient's biological tissue under compression and then to separate at least the tip end portion of each microneedle from the base substrate upon at least partial dissolution of the at least a portion of the base substrate and/or the portion of each of the two or more microneedles in which the effervescent material is disposed. A primary funnel portion may be disposed between and connect the base substrate and the microneedles. The effervescent may be at least partially disposed in the primary funnel portion. For example, the effervescent material may be disposed at an interface of the base substrate (or the primary funnel portion, if present) and a base end of each microneedle.

In some embodiments, the microneedle arrays include a base substrate having a microneedle side and an opposing back side; at least one primary funnel portion extending from the microneedle side of the base substrate; and two or more solid microneedles extending from the at least one primary funnel portion, wherein the two or more solid microneedles include a substance of interest and a secondary funnel portion extending from the at least one primary funnel, wherein the secondary funnel portions include a first matrix material and an effervescent material. The two or more solid microneedles may be constructed to penetrate into the patient's skin under compression and then to separate from the secondary funnel portions upon at least partial dissolution of the secondary funnel portions.

In some embodiments, the microneedle arrays include a base substrate having a microneedle side and an opposing back side; at least one primary funnel portion extending from the microneedle side of the base substrate; and two or more solid microneedles extending from the at least one primary funnel portion, wherein the two or more solid microneedles include a substance of interest and a secondary funnel portion extending from the at least one primary funnel; wherein the two or more solid microneedles are configured to (i) penetrate into the patient's skin under compression and then to separate from the secondary funnel portions, and (ii) release a therapeutically or prophylactically effective amount of the substance of interest to the patient for a sustained period of at least 2 weeks. In some embodiments, the substance of interest is a therapeutic or prophylactic agent, such as a contraceptive hormone.

In another aspect, microneedle patches are provided that include any of the microneedle arrays described herein. In some embodiments, the microneedle patches include a microneedle array as described herein; an adhesive layer; and a handle layer affixed to the base substrate, wherein the handle layer includes a tab portion which extends away from the two or more solid microneedles and permits a person to manually hold the tab portion to manipulate the patch without contacting the two or more solid microneedles.

In yet another aspect, methods of administering a substance of interest to a patient are provided. In some embodiments, the methods include inserting into a biological tissue of the patient the microneedles of an array of microneedles described herein; separating the inserted microneedles from the base substrate (or a funnel portion if present); and releasing the substance of interest, from the separated inserted microneedles, into the biological tissue. The biological tissue may include skin, and the substance of interest may include a contraceptive hormone, such as a progestin. In some embodiments, the separation includes fracture of a bubble structure by application of a shear force to the microneedle array, and/or the separation may include dissolution of wall material surrounding the bubble structure that results in thinning and mechanical failure without application of a shear force. In some embodiments, the separation includes wetting of an effervescent material by biological fluid and subsequent dissolution of material forming part of the microneedles and/or the base substrate (or funnel portion if present).

In a further aspect, methods of making an array of microneedles are provided. In some embodiments, the methods include (a) providing a mold having an upper surface, an opposed lower surface, and an opening in the upper surface, wherein the opening leads to a first cavity proximal to the upper surface and to a second cavity below the first cavity, wherein the first cavity defines at least one funnel portion, and wherein the second cavity defines at least one microneedle; (b) filling at least the second cavity, via the opening in the mold, with a first material which includes a first matrix material and a substance of interest that are dissolved or suspended in a first liquid vehicle; (c) drying the first material in the mold to remove at least a portion of the first liquid vehicle to form at least a tip portion of a microneedle in the second cavity, wherein the tip portion includes the substance of interest; (d) filling the first cavity, and the second cavity if any is unoccupied following steps (b) and (c), via the opening in the mold, with a second material, and entrapping a bubble of gas between the first material and the second material to form a bubble structure at or near a base end of each of the at least one microneedle, wherein the second material includes a second matrix material that is dissolved or suspended in a second liquid vehicle; (e) drying the second material in the mold to remove at least a portion of the second liquid vehicle to form (i) the at least one funnel portion, and (ii) any portion of the at least one microneedle unformed following steps (b) and (c), wherein the at least one funnel portion includes the second matrix material; and (f) removing from the mold the at least one microneedle together with the at least one funnel portion connected thereto, wherein more of the substance of interest is located in the at least one microneedle than is located in the at least one funnel portion.

In some embodiments, the methods include (a) providing a mold having an upper surface, an opposed lower surface, and an opening in the upper surface, wherein the opening leads to a first cavity proximal to the upper surface and to a second cavity below the first cavity, wherein the first cavity defines at least one funnel portion, and wherein the second cavity defines at least one microneedle; (b) filling at least the second cavity, via the opening in the mold, with a first material which includes a first matrix material and a substance of interest that are dissolved or suspended in a first liquid vehicle; (c) drying the first material in the mold to remove at least a portion of the first liquid vehicle to form at least a tip portion of a microneedle in the second cavity, wherein the tip portion includes the substance of interest; (d) filling the first cavity, and the second cavity if any is unoccupied following steps (b) and (c), via the opening in the mold, with a second material which includes an effervescent material and a second matrix material that are dissolved or suspended in a non-aqueous second liquid vehicle; (e) drying the second material in the mold to remove at least a portion of the second liquid vehicle to form (i) the at least one funnel portion, and (ii) any portion of the at least one microneedle unformed following steps (b) and (c), wherein the at least one funnel portion includes the effervescent material and the second matrix material; and (f) removing from the mold the at least one microneedle together with the at least one funnel portion connected thereto, wherein more of the substance of interest is located in the at least one microneedle than is located in the at least one funnel portion.

Additional aspects will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

FIGS. 3A and 3B depict an embodiment of a microneedle patch.

DETAILED DESCRIPTION

Figure 1A:
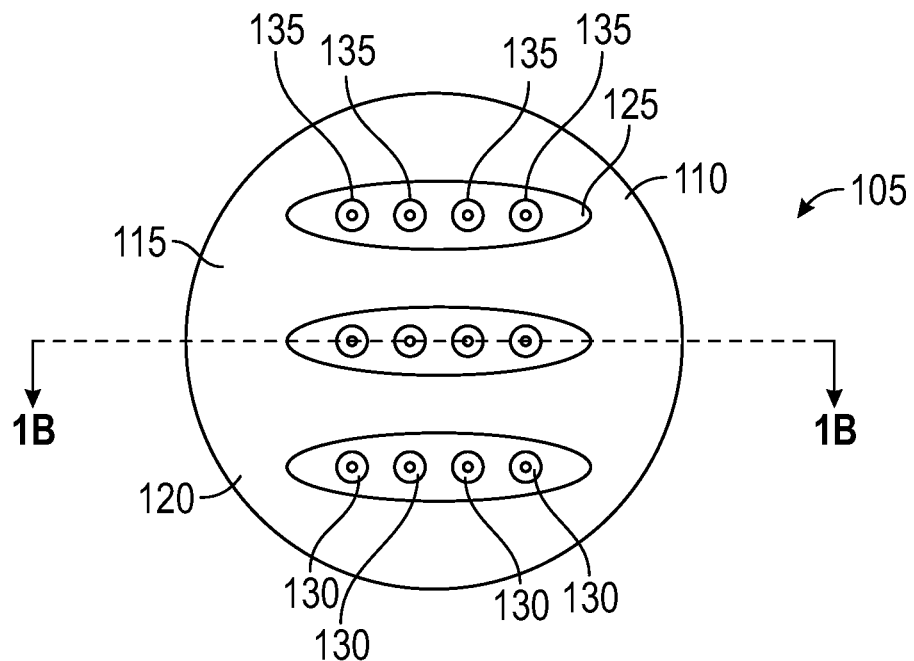
FIGS. 1A-1E depict an embodiment of a microneedle array that includes bubble structures.

Improved microneedle arrays, microneedle patches, and methods of manufacture have been developed. The microneedles described herein may easily and/or rapidly separate from the base of the microneedle patches. As a result, a user may only wear the microneedle patch for seconds prior to removal of the base, after which there is little or no evidence of patch use.

In some embodiments, the microneedles include an active pharmaceutical ingredient or other substance of interest, and arrays of these microneedles are particularly suited for use as/in drug delivery patches, such as for application to a patient's skin. Provided herein are microneedle patches, which, in some embodiments, can be used to self-administer a drug, such as a contraceptive. In some embodiments, the microneedle patches can provide sustained drug release. For example, the microneedle patches can provided long-term contraception by encapsulating a contraceptive hormone in biodegradable microneedles for slow release.

The microneedles can be made of biodegradable, bioerodible, or bioadsorbable polymers (e.g., polylactic acid and poly(lactic-co-glycolic acid)) that may encapsulate a drug, such as a contraceptive hormone (e.g., a progestin, such as levonorgestrel, etonogestrel, or nesterone) for continuous release for at least two weeks, and, in some embodiments, four weeks or longer.

The microneedle patches may be well tolerated, leave little visible evidence of use, and/or maintain plasma concentrations of a drug at or greater than a human therapeutic level for at least two weeks, and, in some embodiments, at least four weeks, at least 2 months, at least 3 months, at least 4 months, at least 5 months, or at least 6 months.

The microneedle arrays described herein may include a feature, such as a bubble structure or effervescent material that facilitates the separation of the microneedles. As used herein with regard to the separation of microneedles, the terms "facilitate", "facilitating", and the like, refer to a feature that (i) reduces a minimum force (e.g., a shearing force) necessary to achieve separation of the microneedles, (ii) reduces the amount of a matrix material that must dissolve in order achieve separation of the microneedles (for example, a bubble structure may result in thinner walls in a microneedle), (iii) increases the rate of dissolution of a funnel portion to which the microneedles are initially connected, a portion of the microneedles that includes an effervescent material, or a combination thereof, or (iv) a combination thereof.

Upon separation of the microneedles, the microneedles of a microneedle array may be embedded in a biological tissue, such as a patient's skin. A microneedle is "embedded" in a biological tissue, when all or a portion of the microneedle's structure is below the surface of the biological tissue. In some embodiments, all of the embedded microneedles' structures are below the surface of a biological tissue. FIG. 1E, for example, depicts a series of four separated and completely embedded microneedles.

Bubble Structures

In some embodiments, the microneedles of the microneedle patches provided herein include a bubble structure. The bubble structures may facilitate separation of a microneedle from a funnel portion. For example, the bubble structures may lessen the minimum shearing force that is necessary to separate the microneedles from the funnels. While the bubble structures may alter the effect of a shearing force on the microneedles, the bubble structures may not undermine the ability of the microneedles to penetrate skin. In other words, the bubble structures do not undesirably impact the microneedles' ability to withstand, without breaking, a compressive force applied during normal use that is effective to penetrate a biological tissue, such as through the stratum corneum of a patient's skin.

As used herein, a microneedle array has a "bubble structure" when one or more bubbles of a gas are present. In some embodiments, the bubble structures are at or near a base end of a microneedle, wherein the base end of a microneedle is the end that contacts a funnel. A bubble of gas is "at or near a base end of a microneedle" when the bubble of gas is (i) at the interface of a microneedle and a funnel, (ii) in the funnel (i.e., defined entirely by a material from which the funnel is formed), and the distance between the tip of the microneedle and the edge of the bubble of gas closest to the base end of the microneedle is less than or equal to 125% of the length of the microneedle, or (iii) in the microneedle (i.e., defined entirely by a material from which the microneedle is formed) and the distance between the tip of the microneedle and the edge of the bubble of gas closest to the tip of the microneedle is greater than or equal to 75% of the length of the microneedle.

In some embodiments, the bubble of gas of a bubble structure is located at the interface of a microneedle and a funnel. A bubble of gas is located at the interface of a microneedle and a funnel when the bubble of gas is bounded partially by (i) a material from which the microneedle is formed, and (ii) a material from which the funnel is formed. For example, X % of the surface area of the bubble of gas may be defined by the material from which the microneedle is formed and the remaining 100-X % of the surface of area of the bubble of gas may be defined by the material from which the funnel is formed.

In some embodiments, the bubble of gas of a bubble structure is in a microneedle, and not at or near a base end of the microneedle. For example, a bubble of gas may be located in a microneedle and the distance between the tip of the microneedle and the edge of the bubble of gas closest to the tip of the microneedle may be less than 75% of the length of the microneedle. In some embodiments, the distance between the tip of the microneedle and the edge of the bubble of gas closest to the tip of the microneedle is about 10% to about 74% of the length of the microneedle, about 20% to about 70% of the length of the microneedle, about 30% to about 70% of the length of the microneedle, or about 40% to about 60% of the length of the microneedle.

The gas of the bubble structures may be, or include, air. In some embodiments, the gas of the bubble structures includes an inert gas, such as argon, nitrogen, etc. The bodies, or volumes, of gas generally may have any shape, but typically are spherical or spheroidal. When spheroidal in shape, the body of gas may be a regularly-shaped spheroid or an irregularly-shaped spheroid. For example, a spheroidal body of gas may have a portion that is less curved, e.g., flatter, than another portion.

The bubble of gas of the bubble structures has a diameter (when spherical) or a largest diameter (when spheroidal), and the ratio of the diameter or largest diameter of the bubble of gas to the width of a microneedle at the microneedle-funnel interface may be about 0.5:1 to about 3:1, about 0.5:1 to about 2.5:1, about 0.5:1 to about 2:1, about 0.5:1 to about 1.9:1, about 0.5:1 to about 1.8:1, about 0.5:1 to about 1.7:1, about 0.5:1 to about 1.6:1, about 0.5:1 to about 1.5:1, about 0.5:1 to about 1.4:1, about 0.5:1 to about 1.3:1, about 0.5:1 to about 1.2:1, about 0.5:1 to about 1.1:1, about 0.5:1 to about 1:1, about 0.5:1 to about 0.99:1, about 0.6:1 to about 0.99:1, about 0.7:1 to about 0.99:1, about 0.8:1 to about 0.99:1, or about 0.9:1 to about 0.99:1. For example, if a microneedle has a width of 300 μm at the microneedle-funnel interface, then a bubble of gas at or near the base end of the microneedle may have a diameter or largest diameter of about 150 μm to about 900 μm. Within an array of microneedles having bubble structures, the bubble structures may have substantially the same diameter or largest diameter, or the bubble structures may have diameters and largest diameters that differ. As explained here, the diameters or largest diameters of the bubble structures may be controlled, and, therefore, selected based one or more desired features. For example, relatively larger bubble structures may be selected to decrease a minimum shearing force necessary to achieve separation of the microneedles.

The bubble of gas of a bubble structure may be centered or off-centered relative to the sides of a microneedle and/or funnel, e.g., relative to a central axis extending from the base to the tip of the microneedle. An array of microneedles may include bubble structures that are centered, off-centered, or a combination thereof. A bubble is "centered" when the shortest distances from the center of the bubble to any side of a funnel or microneedle are substantially identical.

Figure 1B:
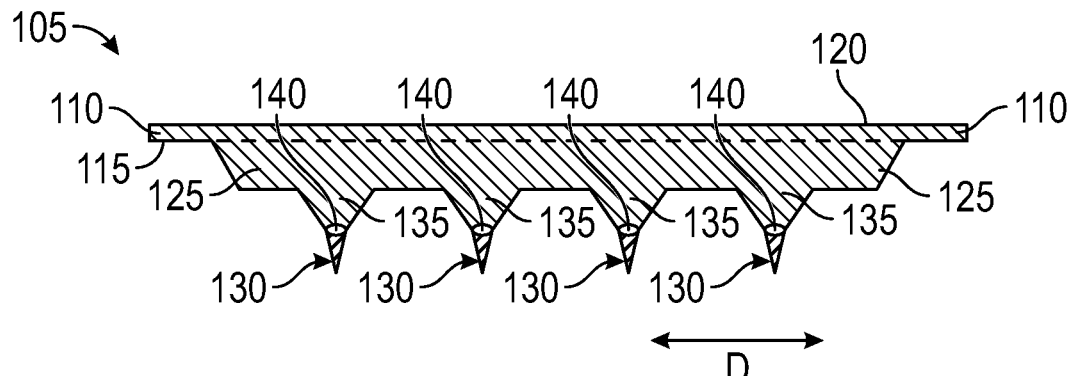

In one embodiment, as illustrated in FIG. 1A (plan view) and FIG. 1B (side cross sectional view), a microneedle array 105 includes a base substrate 110 with a microneedle side 115 and an opposing back side 120. The microneedle array 105 also includes three sets of microneedles 130 with each set having a primary funnel portion 125 extending from the microneedle side 115 of the base substrate 110 and secondary funnel portions 135 extending from the primary funnel portion 125. At the interface of each secondary funnel portion 135 and microneedle 130 is a bubble structure 140. Each primary funnel portion 125 is elongated in a direction (D) that is parallel to the base substrate 110. In this embodiment, the microneedles 130 and funnel portions 125, 135 contain the same substances of interest and excipients, respectively.

The secondary funnel portion is highly advantageous in many embodiments for facilitating insertion of the region of fracture/separation of the microneedles to be located below the surface of the skin or other biological tissue, for example, so that essentially no part of the separated microneedle protrudes out of the biological tissue, which would for example, impede a proper and complete delivery of a dose of the substance of interest. However, in some other embodiments that result may be of little or no concern. Therefore, in some embodiments, the second funnel portions are omitted, and the microneedles extend directly from the primary funnel portions. For example, the bubble structure may be disposed at an interface of the primary funnel portion and a base end of each microneedle. The microneedles are configured to penetrate into a biological tissue under compression and then to separate from the primary funnel portion under shear, by fracture at the bubble structure.

Figure 1C:
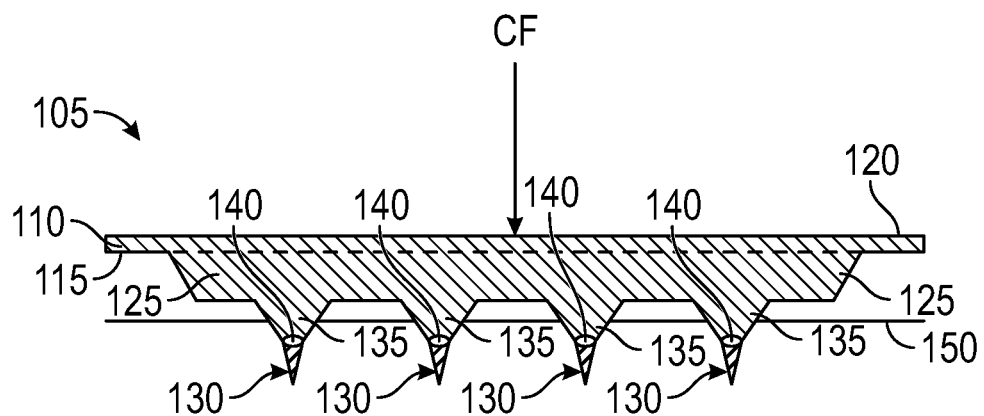
Figure 1D:
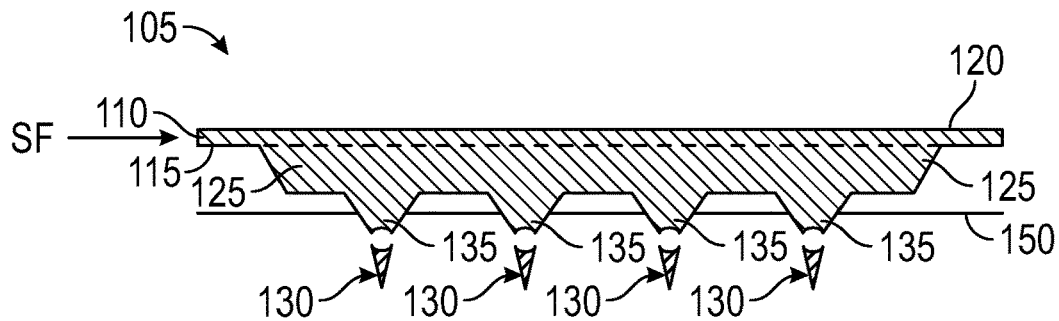
Figure 1E:
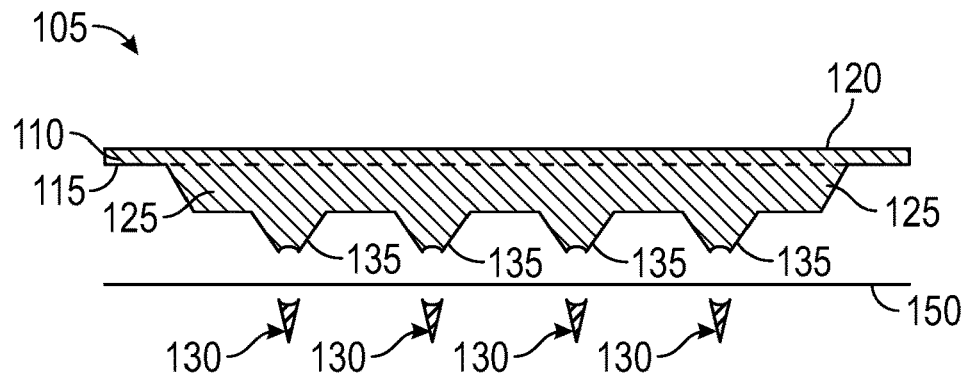

The microneedle array 105 of FIG. 1A and FIG. 1B may be placed on a tissue surface, such as the skin, and upon the application of a compressive force (CF), the microneedles 130 and a portion of the secondary funnels 135 may penetrate the tissue surface 150, as depicted at FIG. 1C (side cross sectional view). As depicted at FIG. 1D (side cross sectional view), the application of a shearing force (SF) to the microneedle array 105 causes the microneedles 130 to separate from the secondary funnels 135. The base substrate 110, the primary funnel portion 125, and the secondary funnel portions 135 then may be removed from the tissue surface. The microneedles 130 remain embedded in the tissue, as depicted at FIG. 1E (side cross sectional view).

Figure 29:
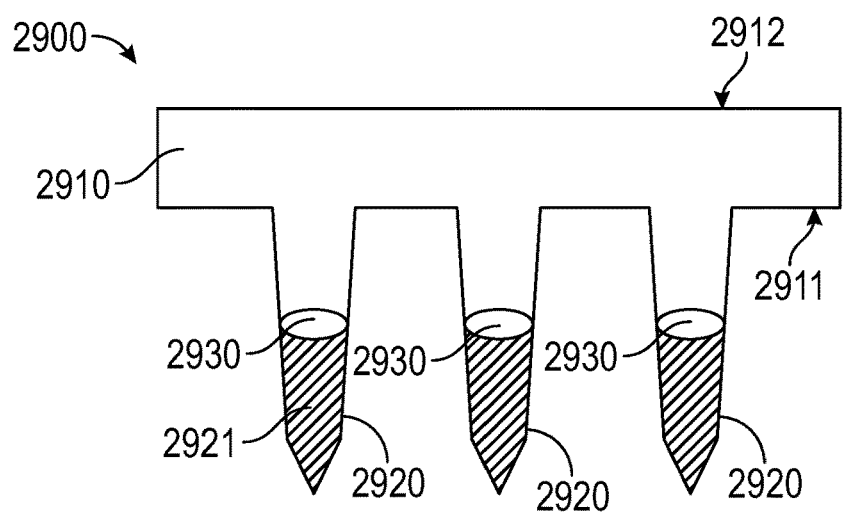
FIG. 29 is a cross-sectional view of one embodiment of a microneedle array including one embodiment of bubble structures.

FIG. 29 depicts a cross-sectional view of one embodiment of a microneedle array 2900. The microneedle array 2900 includes a base substrate 2910 having a microneedle side 2911 and an opposing back side 2912. The microneedle array 2900 includes solid microneedles 2920 extending from the microneedle side 2911 of the base substrate 2910. The solid microneedles 2920 have an obelisk shape, and include a tip end portion 2921 that includes a substance of interest. Each of the solid microneedles 2920 also includes a bubble structure 2930. The solid microneedles 2920 are configured to fracture at the bubble structures 2930 and separate at least the tip end portions 2921 of each microneedle from the base substrate 2910. The bubble structures 2930 of the microneedle array 2900 may facilitate separation of the microneedles 2920 by (i) reducing a minimum shearing force necessary to fracture the microneedles 2920 at the bubble structures 2930, (ii) reducing the thickness of the walls of the microneedles 2920 at or adjacent to the bubble structures 2920, thereby reducing the amount of microneedle-forming matrix material that is required to dissolve in order to fracture the microneedles 2920 at the bubble structures 2930, or a combination thereof. Although the microneedles depicted at FIG. 29 are obelisk-shaped, other microneedle shapes (e.g., conical, cylindrical) may include bubble structures that are not at or near an interface of a microneedle and a funnel portion.

Effervescent Materials

In some embodiments, the microneedle arrays include an effervescent material. The effervescent material may be disposed at any location that facilitates the separation of the microneedles from a base or separation of tip portions of the microneedles from base portions of the microneedles. An effervescent material may be disposed in all or a portion of a funnel portion. For example, a portion of a funnel portion that is adjacent to a base end of a microneedle may include an effervescent material. An effervescent material may be disposed in a portion of a microneedle, particularly a portion that includes and/or is adjacent to a base end of a microneedle. An effervescent material may be disposed in (i) all or a portion of a funnel portion and (ii) a portion of a microneedle. In some embodiments, the microneedles may extend from a funnel portion (e.g., a secondary funnel portion) that includes an effervescent material. In some embodiments, the microneedles may extend from a funnel portion that does not include an effervescent material, but an effervescent material is included in the microneedles, for example, a portion of the microneedles that includes and/or is adjacent to the base ends of the microneedles. As used herein, the phrase "effervescent material" refers to a material or combination of two or more materials that generate a gas upon contacting an aqueous liquid.

When only a portion of a funnel portion includes an effervescent material, the portion of the funnel portion that includes an effervescent material may include a water soluble matrix material, while the portion of the funnel portion that does not include an effervescent material may include a matrix material that is water soluble or non-water soluble.

When a microneedle array includes an effervescent material, the effervescent material may react when contacted with an aqueous liquid, such as a biological fluid (e.g., an interstitial fluid) on, in, or under a biological tissue, thereby generating a gas. Alternatively, the aqueous liquid can be provided externally. For example, the aqueous liquid can be applied to the microneedle array, a biological tissue surface, or a combination thereof. The generated gas may form bubbles in the funnel portion. The gas generated may rapidly impart porosity or increase the porosity of the funnel portion. In addition to generating a gas, an effervescent material also may generate water, which may increase the rate at which the funnel portion including an effervescent material, and/or a water-soluble excipient or matrix material, is dissolved. The generated water also may increase the rate at which the effervescent material dissolves and, therefore, reacts to generate gas.

The rate at which the funnel portion dissolves, therefore, may be increased by (i) the porosity or increased porosity imparted by a gas generated by the effervescent material, (ii) the water generated by the effervescent material, if applicable, or (ii) a combination thereof.

In some embodiments, the effervescent material includes an acid and a salt. The acid may be an organic acid, such as citric acid. The salt may be a salt that imparts a basic pH (i.e., >7) to water in which it is hydrolyzed. The salt may be sodium bicarbonate.

In some embodiments, the effervescent material includes citric acid and sodium bicarbonate. Upon contacting a biological fluid on, in, or under a biological tissue, sodium bicarbonate and citric acid may dissolve and react with each other to generate carbon dioxide and water. The carbon dioxide may increase the porosity of a funnel portion, and the water may contribute to dissolving more of the material of which the funnel is formed, citric acid, and sodium bicarbonate, thereby stimulating the reaction between the citric acid and sodium bicarbonate, and further increasing the rate of dissolution of the funnel portion.

When an effervescent material is included in a funnel portion, the effervescent material and the material(s) of which the funnel portion is formed may be present in the funnel portion at a weight ratio of about 0.1:1 to 1:0.1, about 0.2:1 to 1:0.2, about 0.3:1 to 1:0.3, about 0.4:1 to 1:0.4, about 0.5:1 to 1:0.5, about 0.5:1 to about 1:1, about 0.6:1 to about 1:1, about 0.7:1 to about 1:1, about 0.8:1 to about 1:1, about 1:1 to about 1:0.8, about 1:1 to about 1:0.7, about 1:1 to about 1:0.6, or about 1:1 to about 1:0.5. For example, the effervescent materials may be in a powder form dispersed in the matrix material forming the funnel portion of a microneedle array. The structural component of the microneedle array that includes the effervescent material generally includes at least 10 wt % effervescent material.

When an effervescent material includes two components, such as an acid and a salt, the ratio of the components may be selected to generate a desired amount of gas. The ratio may vary depending on the equivalence factor of one or more of the components.

Figure 2A:
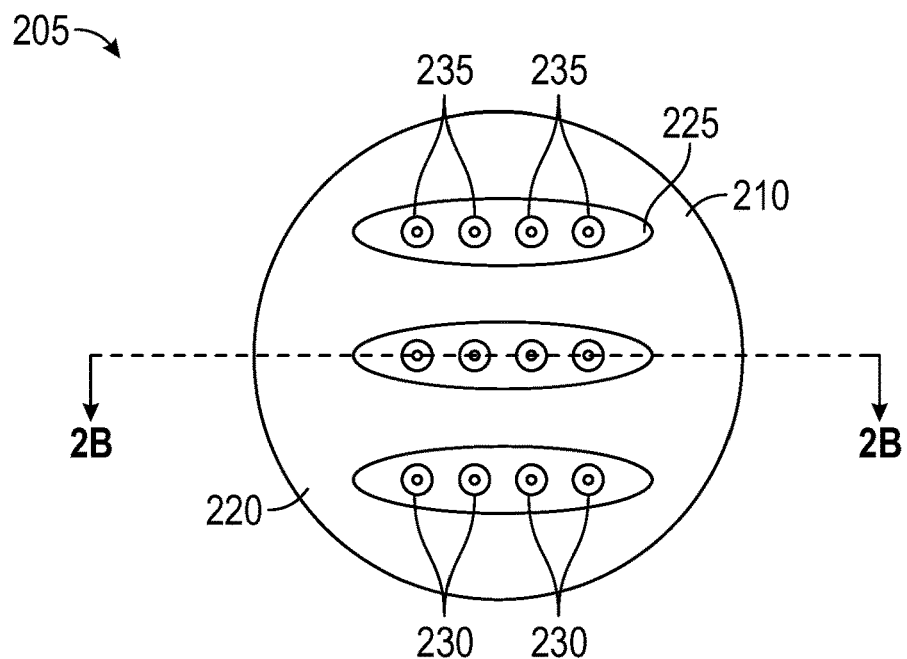
FIGS. 2A-2E depict an embodiment of a microneedle array that includes an effervescent material.
Figure 2B:
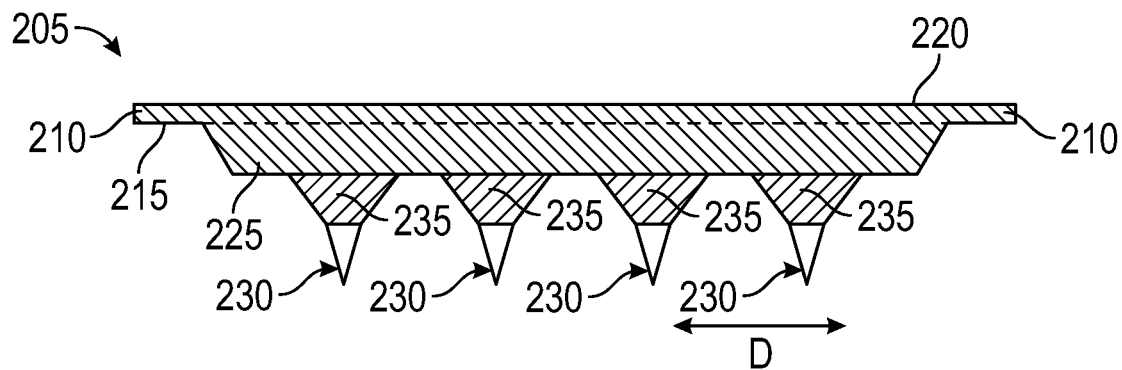

In one embodiment, as illustrated in FIG. 2A (plan view) and FIG. 2B (side cross sectional view), a microneedle array 205 includes a base substrate 210 with a microneedle side 215 and an opposing back side 220. The microneedle array 205 also includes three sets of microneedles 230 with each set having a primary funnel portion 225 extending from the microneedle side 215 of the base substrate 210 and secondary funnel portions 235 extending from the primary funnel portion 225.

The secondary funnel portions 235 include an effervescent material. Each primary funnel portion 225 is elongated in a direction (D) that is parallel to the base substrate 210. In this embodiment, the microneedles 230 include a substance of interest, and the primary funnel portion 135 does not include an effervescent material.

Figure 2C:
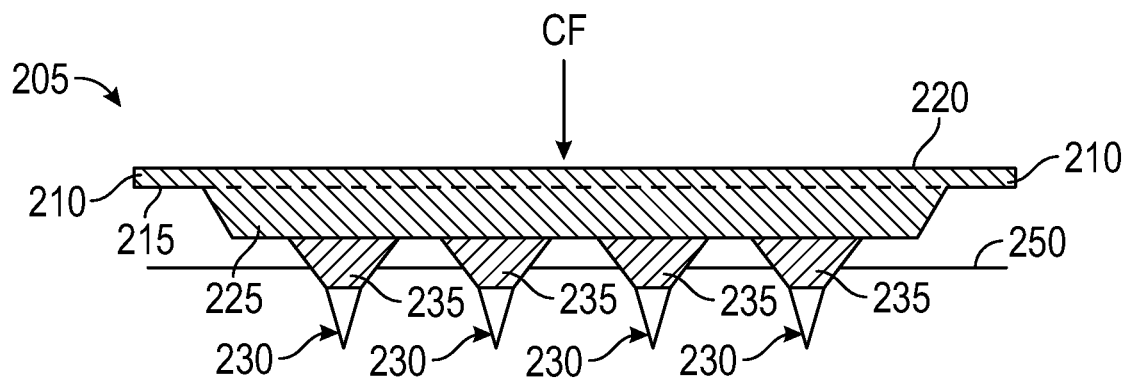
Figure 2D:
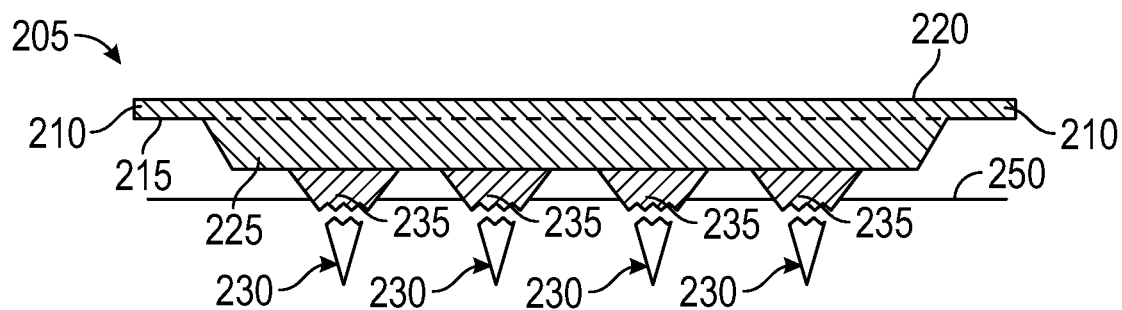
Figure 2E:
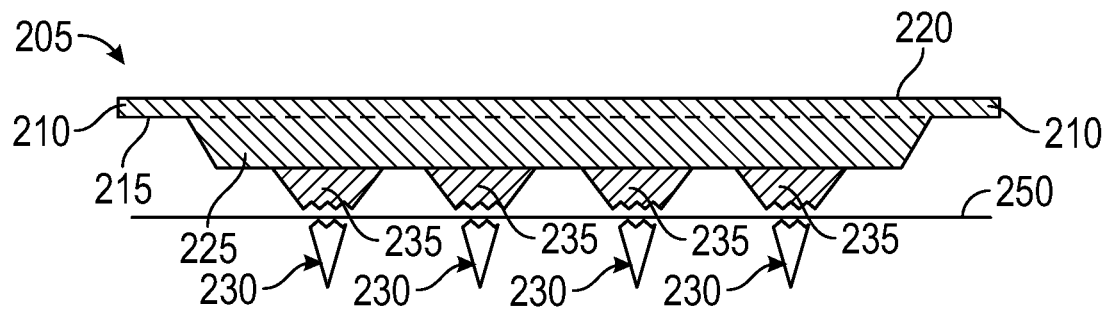

The microneedle array 205 of FIG. 2A and FIG. 2B may be placed on a tissue surface 150, such as the skin, and upon the application of a compressive force (CF), the microneedles 230 and a portion of the secondary funnels 235 may penetrate the tissue surface 250, as depicted at FIG. 2C (side cross sectional view). The secondary funnels 235 therefore may contact a biological fluid, e.g., an interstitial fluid, beneath the tissue surface 250, which wets and activates the effervescent material. The effervescent may increase the rate at which the secondary funnels 235 dissolve and subsequently separate from the microneedles 230, as depicted at FIG. 2D (side cross sectional view). The base substrate 210, the primary funnel portion 225, and the secondary funnel portions 235 then may be removed from the tissue surface. The microneedles 130 remain embedded in the tissue, as depicted at FIG. 2E (side cross sectional view).

Figure 27:
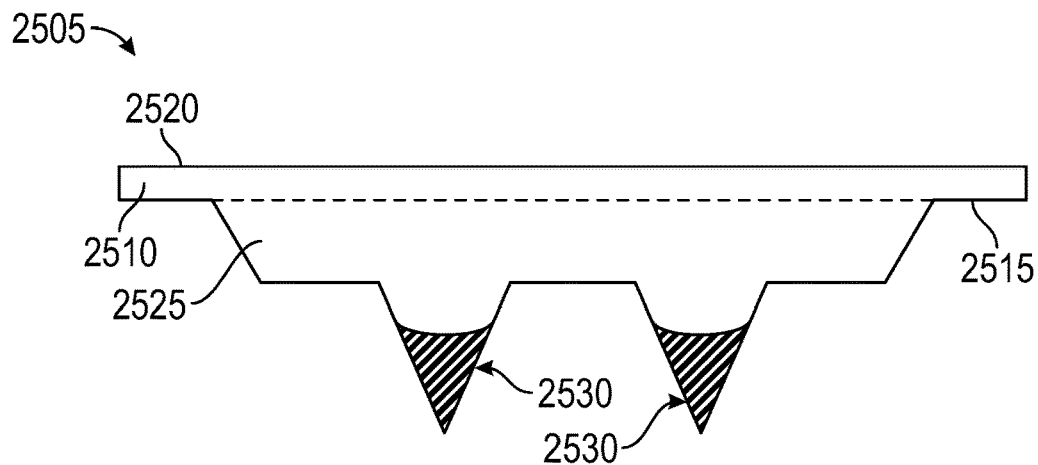
FIG. 27 is a cross-sectional view of one embodiment of a microneedle comprising an effervescent material.
Figure 28:
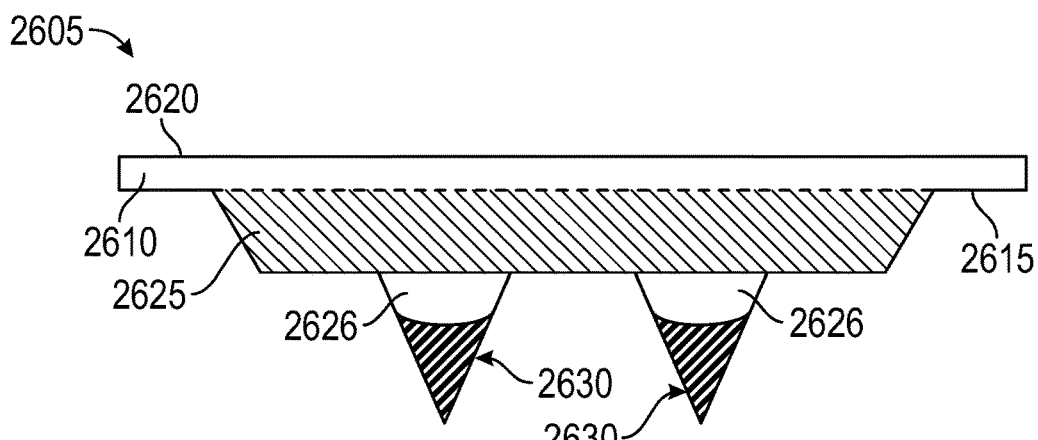
FIG. 28 is a cross-sectional view of another embodiment of a microneedle comprising an effervescent material.

The secondary funnel portion may be highly advantageous for facilitating wetting of the effervescent material and providing that the region of dissolution/separation of the microneedles is located below the surface of the skin or other biological tissue, for the advantages mentioned above. However, in some other embodiments the second funnel portions are omitted, and the microneedles extend directly from the primary funnel portions. The structure of the microneedle array and placement of the effervescent material may differ. For example, FIG. 27 depicts an embodiment of a microneedle array 2505 that includes a base substrate 2510 with a microneedle side 2515 and an opposing back side 2520. The microneedle array 2505 includes a primary funnel portion 2525 from which microneedles 2530 extend. The primary funnel portion 2525 and a base portion of each of the microneedles 2530 include an effervescent material. The tip portions of the microneedles 2530 do not include an effervescent material. FIG. 28 depicts another embodiment of a microneedle array 2605 that includes a base substrate 2610 with a microneedle side 2615 and an opposing back side 2620. The microneedle array 2605 includes a primary funnel portion 2625 from which microneedles 2630 extend. The microneedles 2630 include a base portion 2626 that includes an effervescent material. An effervescent material is not present in the tip portions of the microneedles 2630 or the primary funnel portion 2625. In these figures, second funnel portions are omitted, and the microneedles extend directly from the primary funnel portions.

Microneedle Arrays and Patches

The microneedle arrays include a base substrate and two or more microneedles which extend from a surface of the base substrate. Each microneedle has a proximal end attached to the base substrate directly, or indirectly via one or more funnel portions, and a distal tip end which is sharp and effective to penetrate biological tissue. The microneedle has tapered sidewalls between the proximal and distal ends. The microneedles generally may have any cross-sectional shape, e.g., circular, polygonal, etc.

In some embodiments, the microneedles, or a portion thereof, are substantially conical. In some embodiments, the microneedles, or a portion thereof, are obelisk-shaped. The obelisk-shaped microneedles may be advantageous in some embodiments, because the wider angle at the tip of the microneedles may permit a relatively high loading of material to be arranged at or near the tip.

The funnel portion may be integrally formed with the microneedle. The outer surface of the funnel portion can be distinguished from the microneedle portion of the protruding structure by the distinct change/expansion in the angle of the surfaces defining the different portions of the structure, which can be seen as a rapid expansion in at least one dimension (e.g., radially) as one progresses from the distal end toward the proximal end of the microneedle. The funnel portion is wider at its base end than its microneedle end. This expansion may be designed so that little to no funnel portion is inserted into the targeted tissue layer or space. For example, when the microneedle arrays include an effervescent material dispersed in a funnel portion, the expansion may be designed to permit at least a part of the funnel portion to be inserted into the targeted tissue layer so that a biological fluid, e.g., an interstitial fluid, can contact the funnel portion.

In some embodiments, a microneedle array is provided for administration of a contraceptive hormone or other substance of interest into a biological tissue such as skin, wherein the array includes a base substrate having a microneedle side and an opposing back side; at least one primary funnel portion extending from the microneedle side of the base substrate; and two or more solid microneedles extending from the at least one primary funnel portion, wherein the two or more solid microneedles include a substance of interest and a secondary funnel portion extending from the at least one primary funnel. The primary and secondary funnel portions may include from 0% to 20% of the substance of interest present in the combination of the two or more solid microneedles and the primary and secondary funnel portions from which the two or more solid microneedles extend. This embodiment advantageously avoids wasting the drug in the funnel portions. In some embodiments, the primary and secondary funnel portions include 0% of the substance of interest.

FIG. 3A (perspective view) and FIG. 3B (side cross sectional view) show one example of a microneedle array 305 as part of a microneedle patch 300, wherein each microneedle 330 extends from a funnel portion 325. Each microneedle 330 includes a bubble structure 331 at the interfaces of the microneedles 330 and the funnel portions 325. The microneedle array 305 has a microneedle side 315 and an opposing back side 320. An adhesive layer 335 is applied to the opposing back side 320 of the microneedle array. The microneedle array 305 is affixed to a handling layer 340 by the adhesive layer 335. The handling layer 340 includes a tab portion 345 that extends away from the microneedle array. The tab portion 345 enables a person to manually hold and manipulate the microneedle patch 300 without having to contact the microneedles 330. An adhesive cover 350 is affixed to a portion of the adhesive layer 335 that overlays the tab portion 345 of the handling layer 340. The adhesive cover 350 enables a person to manually hold and manipulate the microneedle patch 300 without having to contact the adhesive layer 335. Although bubble structures are depicted in the embodiment shown at FIG. 3A and FIG. 3B, other embodiments of the microneedle patches do not include bubble structure, and, instead, having secondary funnel portions 325, a portion of the microneedles 330 (e.g., a base end portion of the microneedles 330), or a combination thereof that includes an effervescent material.

An optional mechanical force indicator 355 is disposed between the adhesive layer 335 and the handling layer 340. The mechanical force indicator may be used to indicate to a person the amount of force and/or pressure applied to the patch during its use. For example, in one embodiment, the indicator is configured to provide a signal when a force applied to the patch by a person (in the course of applying the patch to a patient's skin to insert the one or more microneedles into the patient's skin) meets or exceeds a predetermined threshold. The predetermined threshold is the minimum force or some amount greater than the minimum force that is required for a particular microneedle patch to be effectively applied to a patient's skin. That is, it is the force needed to cause the microneedles to be properly, e.g., fully, inserted into a patient's skin.

The length of a microneedle (LAIN) may be between about 50 μm and 2 mm. In most cases they are between about 200 μm and 1200 μm, and ideally between about 500 μm and 1000 μm. The length (height) of a funnel ($L_{FUN}$) may be between about 10 μm and 1 cm. In most cases, funnels are between about 200 μm and 2000 μm, and more preferably between about 500 μm and 1500 μm. The ratio $L_{FUN}/L_{MN}$ may be between about 0.1 and 10, more typically between about 0.3 and 4 and more preferably between about 0.5 and 2 or between about 0.5 and 1, although a ratio between about 1 and 2 is also useful. The ratio $L_{FUN}/L_{MN}$ could be less than about 1 or could be greater than about 1. The sum $L_{MN}+L_{FUN}$ may be between about 60 μm and 1.2 cm, more typically between about 300 μm and 1.5 mm and more preferably between about 700 μm and 1.2 mm. $L_{MN}+L_{FUN}$ can be greater than about 1 mm, or greater than about 1.2 mm or greater than about 1.5 mm.

The volume of a microneedle ($V_{MN}$) can be between about 1 nl and 100 nl. In most cases, it is between about 5 nl and 20 nl. The volume of a funnel ($V_{FUN}$) can be about 1 nl to 20,000 nl, more typically between about 5 nl and 1000 nl and more preferably between about 10 nl and 200 nl. The ratio $V_{FUN}/V_{MN}$ can be between about 0.1 to 100, more typically between about 0.5 and 20 and more preferably between about 1 and 10 or between about 2 and 5.

The cross-sectional area of the microneedle (or, if applicable, the combined cross-sectional area of the microneedle and a bubble structure) where it meets the funnel ($A_{MN\text{-}FUN}$) is between about 300 μm² and 800,000 μm². In most cases, it is between about 10,000 μm² and 500,000 μm² and more preferably between about 50,000 μm² and 200,000 μm². The cross-sectional area of the funnel-base interface ($A_{FUN\text{-}BASE}$) is between about 301 μm² and 8×10 μm², more typically between about 10,000 μm² and 5×10⁶ μm² and more preferably between about 100,000 μm² and 2×10⁶ μm². The ratio $A_{FUN\text{-}BASE}/A_{MN\text{-}FUN}$ is always greater than 1, because the funnel expands out from the microneedle. The ratio $A_{FUN\text{-}BASE}/A_{MN\text{-}FUN}$ is between about 1.1 to 2500, more typically between about 1.5 and 100 and more preferably between about 2 and 10.

Two or more microneedles may be arranged on a base substrate in any suitable density. For example, a plurality of microneedles may be arranged in even or staggered rows in an array, wherein each microneedle is separated from its nearest neighboring microneedle by a distance about equal to the height of the microneedle.

The width at the microneedle-funnel interface ($W_{MN/FUN}$) is between about 20 μm and 1000 μm. In most cases, it is between about 100 μm and 500 μm and more preferably between about 200 μm and 400 μm. The width at the funnel-base interface ($W_{FUN\text{-}BASE}$) is between about 30 μm and 1 cm, more typically between about 300 μm and 1500 μm and more preferably between about 500 μm and 1000 μm. The ratio $W_{FUN\text{-}BASE}/W_{MN\text{-}FUN}$ is always greater than 1, because the funnel expands out from the microneedle. The ratio $W_{FUN\text{-}BASE}/W_{MN\text{-}FUN}$ can be between about 1.1 and 50, more typically between about 1.5 and 10 and more preferably between about 2 and 5.

A microneedle patch may include different microneedles. For example, the different microneedles of a microneedle patch may include different compositions of materials, including different actives and/or excipients and/or other materials. Microneedles that contain the same composition of materials may be connected to common funnel(s). In addition to different microneedles, rows, or regions having different material loaded within them, the microneedles and funnels themselves may have discrete layers of materials. The discrete layers may appear to be in a stacked, or striped, or the discrete layers may be in the form of shell layers starting from the sidewall of the cavity in the mold inward.

Funnel Portions

In some embodiments, the microneedle patches provided herein advantageously include one or more funnel portions between the base substrate and the microneedles themselves. The addition of a funnel portion (sometimes referred to herein as a "funnel," a "funnel portion," "a pedestal," a "primary funnel portion," a "secondary funnel portion," or a "funnel lead-in") imparts certain advantages in its use, its manufacture, or in both its use and manufacturing.

First, tissue insertion difficulties may be lessened by incorporating funnels into the microneedle patches, because they raise the microneedles off their base or backing layer allowing the microneedles to more simply contact and penetrate the targeted tissue—without having to make the microneedles longer. This can increase the microneedle insertion efficiency (e.g., success rate of microneedle penetration) and decrease the amount of force required to successfully apply a microneedle patch. That is, a larger number of the collection of microneedles puncture the tissue (for example, greater than or equal to 80% or 90% or 95% of the microneedles in a patch) or a larger fraction of each microneedle penetrates into the skin (for example, an average of greater than or equal to 50% or 75% or 80% or 90% of 95% of the length or the volume of the microneedles in a patch). The net result of either of these measures of microneedle penetration success rate is that a larger portion of a substance of interest being administered by the microneedles is delivered into the tissue.

This approach to microneedle design can also advantageously provide microneedle insertion with little to no funnel insertion after applying a minimum force. That is, the resulting insertion depth of the microneedles with funnels is less sensitive to the application of excessive force during patch application because the rapid expansion of the funnel section hinders insertion and results in insertion up to the microneedle-funnel interface. This allows them to be inserted by simple thumb pressure alone, thumb pressure with a mechanism to indicate the minimum required force has been applied, or simpler and less aggressive applicators that may not rely on impact. For example, if an array of longer microneedles is pressed against the skin, it is possible to only partially insert the microneedles, allowing them to still penetrate shallowly. However, the actual depth of microneedle insertion is very difficult to control since the minimum force required will vary due to differences between individuals (e.g., skin types) and application sites (e.g., locations on a patient's body). Therefore, the insertion force to partially insert an array of longer microneedles will vary and by applying a force that is too small or too large will result in improper microneedle insertion depth. This is alleviated when using microneedles with funnel lead-ins because the rapid expansion of the funnel portion limits insertion depth. If the minimum force (or greater) has been applied, the insertion depth is consistent.

Second, manufacturing challenges can be significantly lessened by adding funnels, because they greatly increase the target area during a mold filling step, since the funnels expand out from the microneedle cavity. This larger area target (i.e., funnel-base interface) greatly relaxes the positional accuracy required for the deposition/filling system compared to a mold containing no funnels, in which the target area would be the microneedle-base interface. In addition, the volume to fill a microneedle with a funnel can be many times greater than the microneedle itself, thereby reducing this constraint too.

Other advantages and benefits of the microneedle array designs and the methods of manufacture that have been developed are described throughout the rest of the specification. Certain of the improved manufacturing methods are applicable to microneedle arrays that include funnel portions, as well as to microneedle arrays that do not include funnel portions.

The funnel portions can be formed into a variety of different configurations. The funnel portions can have tapered walls (steeply or shallowly), 'stepped' walls, tapered walls that then become vertical, hemispherical walls, or a combination thereof. Funnel portions can be symmetric or asymmetric. Some of these configurations are illustrated in the cross-sectional views shown at FIGS. 4A-4I.

Figure 4A:
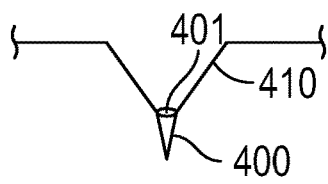
FIGS. 4A-4I depict embodiments of funnel portions and microneedles.
Figure 4B:
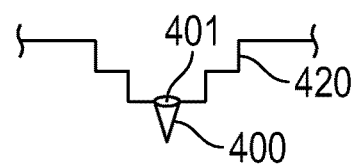
Figure 4C:
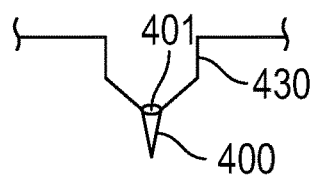
Figure 4D:
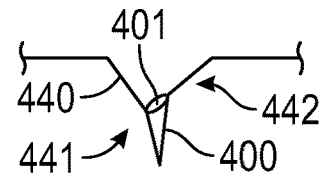
Figure 4E:
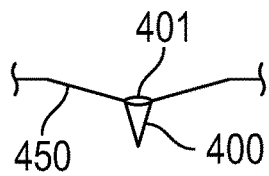
Figure 4F:
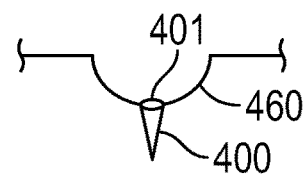

Each configuration of the microneedles depicted at FIGS. 4A-4F (cross-sectional side views) include a bubble structure 401 at or near the base end of the microneedles. FIG. 4A shows a cone shaped funnel portion 410 which has a straight tapered sidewall and microneedle 400 extending therefrom. FIG. 4B shows a funnel portion 420 with a stepped sidewall and a microneedle 400 extending therefrom. FIG. 4C shows a funnel portion 430 with a sidewall that has both a tapered portion and an untapered (vertical) portion and a microneedle 400 extending therefrom. FIG. 4D shows an axially asymmetric funnel portion 440 with a sidewall that tapers at a different angle on one side 441 of the funnel portion as compared to another (e.g., opposed) side 442 of the funnel portion, with a microneedle 300 extending therefrom. FIG. 4E shows a shallow cone shaped funnel portion 450 which has a straight tapered sidewall and a microneedle 400 extending therefrom. FIG. 4F shows a hemispherical shaped funnel portion 460 which has a curved sidewall and a microneedle 400 extending therefrom.

Figure 4G:
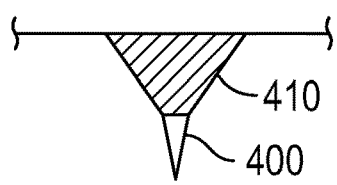
Figure 4H:
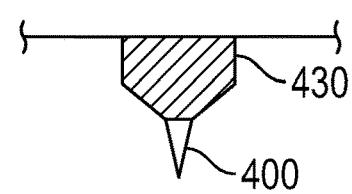
Figure 4I:
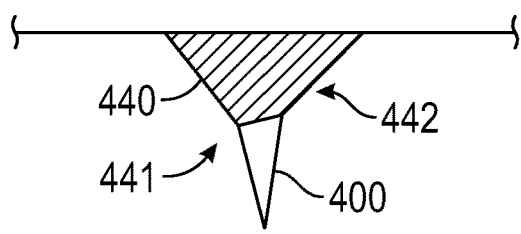

Each configuration of the microneedles depicted at FIGS. 4G-4I (cross-sectional side views) includes a funnel portion that includes an effervescent material. When an effervescent material is included in a funnel portion, the funnel portion may be configured to contact a biological fluid, e.g., an interstitial fluid, upon penetration of a biological tissue by the microneedle array. FIG. 4G shows a cone shaped funnel portion 410 which has a straight tapered sidewall and microneedle 400 extending therefrom. FIG. 4I1 shows a funnel portion 430 with a sidewall that has both a tapered portion and an untapered (vertical) portion and a microneedle 400 extending therefrom. FIG. 4I shows an axially asymmetric funnel portion 440 with a sidewall that tapers at a different angle on one side 441 of the funnel portion as compared to another (e.g., opposed) side 442 of the funnel portion, with a microneedle 300 extending therefrom. The funnel portions that include an effervescent material, such as those depicted at FIGS. 4G-4I may be used in the microneedle patch depicted at FIGS. 3A and 3B. In some embodiments, an effervescent material is present in only a portion of a funnel portion. In some embodiments, an effervescent material is present in a portion of a microneedle, e.g., a base end portion of a microneedle. When an effervescent material is present in a portion of a microneedle, the effervescent material may not be present in a funnel portion corresponding to the microneedle, or the effervescent material may be present in at least a portion of the funnel portion corresponding to the microneedle.

A single microneedle array or patch may have funnel portions having two or more different geometries. For example, an array could include one row of microneedles having funnel portions of a first size or shape and a second row of microneedles having funnel portions of a second size or shape. Such differences could be beneficially designed, for example, to deliver two different substances of interest.

Manufacturing and use considerations also drive the selection of the geometry of the funnel portion. For example, the density of the microneedles and funnels within an array (i.e., the spacing) may also be balanced with microneedle/funnel geometry to allow for simple needle insertion with little to no funnel insertion (i.e., because more closely space microneedles are generally more difficult to insert). As another example, during manufacturing, a volume of solution is deposited into the funnel portions of a mold and when dried/cured, the solute substantially migrates into the microneedle and its tip portion of the mold. The funnel shape, in one embodiment, is designed to promote and maximize this solute migration.

Figure 5A:
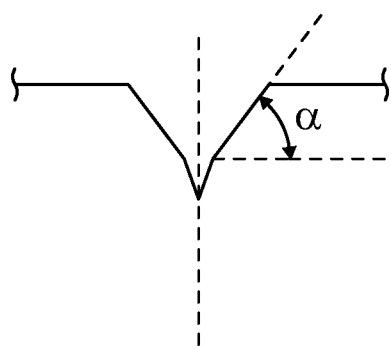
FIGS. 5A-5C depict embodiments of funnel portions and microneedles.
Figure 5B:
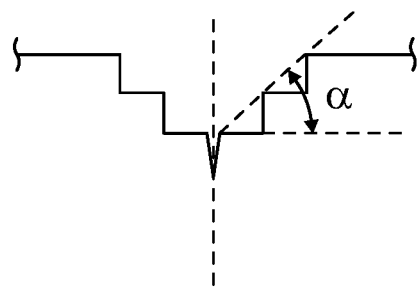
Figure 5C:
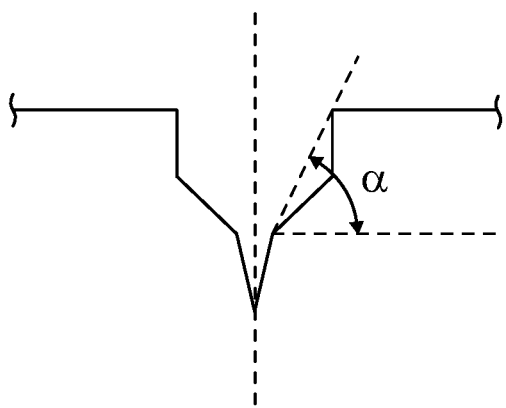

The funnel portion expands from the location where it connects to the microneedle in at least one dimension. In most cases it expands radially. The minor angle $\alpha$ is located between a line that extends from the funnel-microneedle interface to where the funnel portion meets the base and a line that extends from the same point and is perpendicular the central axis of the microneedle, as shown in the cross-sectional side views in FIG. 5A, FIG. 5B, and FIG. 5C. The angle $\alpha$ is less than about 90°, but greater than about 10°. In most cases, the angle is between about 30° and 75° and more preferably between about 45° and about 60°.

Each microneedle can be associated with one funnel and each funnel associated with one microneedle. Alternatively, one microneedle can be associated with more than one funnel. Alternatively, one funnel can be associated with more than one microneedle. In general, on a per patch basis the number of microneedles number of funnels. However, the number of funnels may exceed the number of microneedles when the funnels are used in series. The number of microneedles per patch is generally between 1 and 10,000, and in most cases is between about 20 and 1000 and more preferably between about 50 and 500. The number of funnels per patch is generally between about 1 and 10,000, and in most cases is between about 5 and 500 and more preferably between about 10 and 500. The ratio of funnels to microneedle is between about 0.01 to 10, more typically between about 0.05 and 4 and more preferably between 0.1 and 1. In some cases, the ratio of funnels to microneedle is about 1. In other cases, the ratio of funnels to microneedle is about 2 or greater. In some cases, a plurality of microneedles all in a row is associated with the same funnel. In some cases, some of the microneedles are associated with funnels and other microneedles are not associated with funnels. In some cases, the number of funnels that each microneedle is associated with within a patch is not the same for all microneedles or for all funnels.

Funnels can also be used in series, i.e., a collection of funnels where the first funnel (i.e., a primary funnel portion) (base end) feeds a number of other funnels (i.e., secondary funnel portions). For example, each microneedle may have its own funnel and a row or section of a patch of microneedles and funnels may be connected to a larger elongated funnel. This is particularly useful when filling a microneedle patch with multiple actives for one reason or another (e.g., actives are incompatible with one another, formulated differently for stability and/or release kinetics). For example, some microneedles could release the active rapidly thereby providing an immediate burst to raise the blood levels of the active into the therapeutic range quickly and other microneedles could be designed to release the active slowly to keep the blood levels of the active in the therapeutic range for an extended period of time. Alternatively, a single large funnel may be connected to an entire microneedle (with or without their own separate funnels) patch. This may be useful for filling of a single active ingredient.

Substance of Interest/Active Pharmaceutical Ingredient

A wide range of substances may be formulated for delivery to biological tissues with the present microneedles and methods. As used herein, the term "substance of interest" includes active pharmaceutical ingredients, allergens, vitamins, cosmetic agents, cosmeceuticals, diagnostic agents, markers (e.g., colored dyes or radiological dyes or markers), and other materials that are desirable to introduce into a biological tissue. The "substance of interest" is sometimes referred to herein as "the active." In a preferred embodiment, the biological tissue is a tissue of a human or other mammal, including but not limited to the skin, ocular tissues, or other mucosa (e.g., buccal, nasal, gastrointestinal, rectal, etc.) of human or other mammal. In an alternative embodiment, the biological tissue is a plant tissue.

In some embodiments, the substance of interest is a prophylactic, therapeutic, or diagnostic agent useful in medical or veterinary application. In some embodiments, the substance of interest is a prophylactic or therapeutic substance, which may be referred to herein as an API. In some embodiments, the API is selected from suitable proteins, peptides and fragments thereof, which can be naturally occurring, synthesized or recombinantly produced. Representative examples of types of API for delivery include antibiotics, antiviral agents, analgesics, anesthetics, antihistamines, anti-inflammatory agents, anti-coagulants, allergens, vitamins, antineoplastic agents.

In some embodiments, the substance of interest is a hormone. The hormone may include a contraceptive hormone, such as a progestin. Examples of contraceptive hormones include levonorgestrel, etonogestrel, and nesterone. The hormone may include glucagon-like peptide-1 (GLP-1). The hormone may include testosterone. The hormone may include an estrogen, e.g., ethinyl estradiol.

In some embodiments, the substance of interest includes a vaccine. Examples of vaccines include vaccines for infectious diseases, therapeutic vaccines for cancers, neurological disorders, allergies, and smoking cessation or other addictions. Some examples of current and future vaccines for the prevention of, anthrax, cervical cancer (human papillomavirus), dengue fever, diphtheria, Ebola, hepatitis A, hepatitis B, hepatitis C, Haemophilus influenzae type b (Hib), HIV/AIDS, human papillomavirus (HPV), influenza (seasonal and pandemic), Japanese encephalitis (JE), lyme disease, malaria, measles, meningococcal, monkeypox, mumps, pertussis, pneumococcal, polio, rabies, rotavirus, rubella, shingles (herpes zoster), smallpox, tetanus, typhoid, tuberculosis (TB), varicella (chickenpox), West Nile, and yellow fever.

In some embodiments, the substance of interest includes a therapeutic agent. The therapeutic agent may be selected from small molecules and larger biotechnology produced or purified molecules (e.g., peptides, proteins, DNA, RNA). Examples of therapeutics, which may include their analogues and antagonists, include but are not limited to insulin, insulin-like growth factor, insultropin, parathyroid hormone, pramlintide acetate, growth hormone release hormone, growth hormone release factor, mecasermin, Factor VIII, Factor IX, antithrombin III, protein C, protein S, β-glucocerebrosidase, alglucosidase-α, laronidase, idursulphase, galsulphase, agalsidase-β, α-1 proteinase inhibitor, lactase, pancreatic enzymes, adenosine deaminase, pooled immunoglobulins, human albumin, erythropoietin, darbepoetin-α, filgrastim, pegfilgrastim, sargramostim, oprelvekin, human follicle-stimulating hormone, human chorionic gonadotropin, lutropin-α, interferon (alpha, beta, gamma), aldesleukin, alteplase, reteplase, tenecteplase, urokinase, factor VIIa, drotrecogin-α, salmon calcitonin, exenatide, octreotide, dibotermin-α, recombinant human bone morphogenic protein 7, histrelin acetate, palifermin, becaplermin, trypsin, nesiritide, botulinum toxin (types A and B), collagenase, human deoxyribonuclease I, hyaluronidase, papain, 1-asparaginase, peg-asparaginase, rasburicase, lepirudin, bivalirudin, streptokinase, anistreplase, bevacizumab, cetuximab, panitumumab, alemtuzumab, rituximab, trastuzumab, abatacept, anakinra, adalimumab, etanercept, infliximab, alefacept, efalizuman, natalizumab, eculizumab, antithymocyte globulin, basiliximab, daclizumab, muromonab-CD3, omalizumab, palivizumab, enfuvirtide, abciximab, pegvisomant, crotalidene polyvalent fab (ovine), digoxin immune serum fab (ovine), ranibizumab, denileukin diftitox, ibritumomab tiuxetan, gemtuzumab ozogamicin, tositumomab, I-tositumomab, anti-rhesus (rh) immunoglobulin G, desmopressin, vasopressin, deamino [Va14, D-Arg8] arginine vasopressin, somatostatin, somatotropin, bradykinin, bleomycin sulfate, chymopapain, glucagon, epoprostenol, cholecystokinin, oxytocin, corticotropin, prostaglandin, pentigetide, thymosin alpha-1, alpha-1 antitrypsin, fentanyl, lidocaine, epinephrine, sumatriptan, benztropine mesylate, liraglutide, fondaparinux, heparin, hydromorphone, omacetaxine mepesuccinate, pramlintide acetate, thyrotropin-alpha, glycopyrrolate, dihydroergotamine mesylate, Bortezomib, triptoreline pamaote, teduglutide, methylnaltrexone bromide, pasireotide, ondansetron hydrochloride, droperidol, triamcinolone (hex)acetonide, aripiprazole, estradiol valerate, morphine sulfate, olanzapine, methadone hydrochloride, and methotrexate.

In some embodiments, the substance of interest is a vitamin, herb, or dietary supplement known in the art. Non-limiting examples include 5-HTP (5-hydroxytryptophan), acai berry, acetyl-L-carnitine, activated charcoal, aloe vera, alpha-lipoic acid, apple cider vinegar, arginine, ashitaba, ashwagandha, astaxanthin, barley, bee pollen, beta-alanine, beta-carotene, beta-glucans, biotin, bitter melon, black cherry, black cohosh, black currant, black tea, branched-ahain amino acids, bromelain (bromelin), calcium, camphor, chamomile, chasteberry, chitosan, chlorella, chlorophyll, choline, chondroitin, chromium, cinnamon, citicoline, coconut water, coenzyme Q10, conjugated linoleic acid, cordyceps, cranberry, creatine, D-mannose, damiana, deer velvet, DHEA, DMSO, echinacea, EDTA, elderberry, emu Oil, evening primrose oil, fenugreek, feverfew, folic acid, forskolin, GABA (gamma-aminobutyric acid), gelatin, ginger, Ginkgo biloba, ginseng, glycine, glucosamine, glucosamine sulfate, glutathione, gotu kola, grape seed extract, green coffee, guarana, guggul, gymnema, hawthorn, hibiscus, holy basil, horny goat weed, inulin, iron, krill oil, L-carnitine, L-citrulline, L-trypotophan, *lactobacillus*, magnesium, magnolia, milk thistle, MSM (methylsulfonylmethane), niacin, olive, omega-3 fatty acids, oolong tea, oregano, passionflower, pectin, phenylalanine, phosphatidylserine, potassium, probiotics, progesterone, quercetin, ribose, red yeast rice, reishi mushroom, resveratrol, rosehip, saffron, SAM-e, saw palmetto, schisandra, sea buckthorn, selenium, senna, slippery elm, St. John's wort, stinging nettle, tea tree oil, theanine, tribulus terrestris, turmeric (curcumin), tyrosine, valerian, vitamin A, vitamin B12, vitamin C, vitamin D, vitamin E, vitamin K, whey protein, witch hazel, xanthan gum, xylitol, yohimbe, and zinc.

The microneedle patches may include a single substance of interest or they may include two or more substances of interest. In the latter case, the different substances may be provided together within one of the microneedles, or some microneedles in an array of microneedles contain one substance of interest while other microneedles contain another substance of interest.

The API desirably is provided in a stable formulation or composition (i.e., one in which the biologically active material therein essentially retains its physical stability and/or chemical stability and/or biological activity upon storage). Stability can be measured at a selected temperature for a selected period, as known in the art.

In some embodiments, the substance of interest is provided as a solid that is "dry" or has been "dried" to form the one or more microneedles and becomes solubilized in vivo following insertion of the microneedle into the patient's biological tissue. As used herein, the term "dry" or "dried" refers to a composition from which a substantial portion of any water has been removed to produce a solid phase of the composition. The term does not require the complete absence of moisture (e.g., the API or the formulation including the API may have a moisture content from about 0.1% by weight and about 25% by weight).

The substance of interest may be included in a formulation with one or more excipients and other additives, as detailed below.

Matrix Materials/Excipients

Matrix materials form the bulk of the microneedles, funnel portions, including the primary funnel portion and secondary funnel portions, and optionally the base substrate. The microneedles, primary funnel portion, and secondary funnel portions may be formed of the same or different matrix materials. The matrix materials typically include a biocompatible polymeric material, alone or in combination with other materials. An effervescent material may be dispersed in the matrix material used to form a funnel portion, a portion of a microneedle, or a combination thereof. A substance of interested may be dispersed in the matrix material used to form microneedles and/or funnel portions.

The matrix materials may be biodegradable, bioerodible, and/or bioabsorbable. One or more matrix materials may be selected based on the rate at which the one or more matrix materials biodegrade, bioerode, or become bioabsorbed. In some embodiments, the matrix materials are water soluble. The water soluble matrix materials may dissolve within minutes to tens of minutes upon contacting a fluid, such as a biological fluid.

In some embodiments, microneedles are formed of a matrix material that is biodegradable, bioerodible, and/or bioabsorbable, and the matrix material encapsulates a substance of interest. The substance of interest is released as the matrix material degrades, erodes, is absorbed, or a combination thereof.

In some embodiments, microneedles are formed of a water soluble matrix material that encapsulates biodegradable polymer microparticles. The biodegradable polymer microparticles, in turn, encapsulate a substance of interest. The microneedles may dissolve relatively quickly upon contacting a biological fluid, leaving the biodegradable polymer microparticles behind (e.g., within a biological tissue), which slowly degrade and release the substance of interest.

In some embodiments, the bulk of the microneedles are formed from a matrix material including poly-lactic acid, poly-lactic glycolic acid, polycaprolactone, or a combination thereof. In some embodiments, the funnel portions, including the primary funnel portion and/or the secondary funnel portions, are formed from a matrix material include poly-vinyl alcohol, a carbohydrate, or a combination thereof. In some embodiments, the carbohydrate is sucrose. In some embodiments, the funnel portions, including the primary funnel portion and/or the secondary funnel portions, are formed from a matrix material that includes polyvinylpyrrolidone. Other matrix materials, however, are envisioned.

As used herein, the terms "matrix material" and "excipient" are used interchangeably when referring to any excipients that are not volatilized or otherwise removed during drying and formation of the microneedles and funnels.

The fluid solution used in the mold filling processes described herein may include any of a variety of excipients. The excipients may consist of those that are widely used in pharmaceutical formulations or ones that are novel. In a preferred embodiment, the excipients are ones in FDA approved drug products (see the Inactive Ingredient Search for Approved Drug Products at http://www.accessdata.fda-.gov/scripts/cder/iig/index.Cfm). None, one, or more than one excipient from the following categories of excipients may be used: stabilizers, buffers, bulking agents or fillers, adjuvants, surfactants, disintegrants, antioxidants, solubilizers, lyo-protectants, antimicrobials, antiadherents, colors, lubricants, viscosity enhancer, glidants, preservatives, materials for prolonging or controlling delivery (e.g., biodegradable polymers, gels, depot forming materials, and others). A single excipient may perform more than one formulation role. For example, a sugar may be used as a stabilizer and a bulking agent, or a buffer may be used to both buffer pH and protect the active from oxidation. Some examples of excipients include lactose, sucrose, glucose, mannitol, sorbitol, trehalose, fructose, galactose, dextrose, xylitol, maltitol, raffinose, dextran, cyclodextrin, collagen, glycine, histidine, calcium carbonate, magnesium stearate, serum albumin (human and/or animal sources), gelatin, chitosan, DNA, hylaruronic acid, polyvinylpyrrolidone, polyvinyl alcohol, polylactic acid (PLA), polyglycolic acid (PGA), polylactive co-glycolic acid (PLGA), polyethylene glycol (PEG, PEG 300, PEG 400, PEG 600, PEG 3350, PEG 4000), cellulose, methylcellulose, carboxymethyl cellulose, sodium carboxymethyl cellulose, hydroxypropyl methylcellulose, acacia, Lecithin, Polysorbate 20, Polysorbate 80, Pluronic F-68, Sorbitantrioleate (span 85), EDTA, hydroxypropyl cellulose, sodium chloride, sodium phosphate, ammonium acetate, potassium phosphate, sodium citrate, sodium hydroxide, sodium carbonate, Tris base-65, Tris acetate, Tris HCl-65, citrate buffer, talc, silica, fats, methyl paraben, propyl paraben, selenium, vitamins (A, E, C, retinyl palmitate, and selenium), amino acids (methionine, cysteine, arginine), citric acid, sodium citrate, benzyl alcohol, chrlorbutanol, cresol, phenol, thimerosal, EDTA, acetone sodium bisulfate, ascorbyl palmitate, ascorbate, castor oil, cottonseed oil, alum, aluminum hydroxide, aluminum phosphate, calcium phosphate hydroxide, paraffin oil, squalene, Quil A, IL-1, IL-2, IL-12, Freund's complete adjuvant, Freund's incomplete adjuvant, killed *Bordetella pertussis, Mycoobacterium bovis*, and toxoids. The one or more selected excipients may be selected to improve the stability of the substance of interest during drying and storage of the microneedle devices, as well providing bulk and/or mechanical properties to the microneedle array.

In some preferred embodiments, the microneedle is made of a biodegradable matrix material that encapsulates an API, and upon insertion into a patient the whole microneedle separates and degrades slowly in the skin. In some other embodiments, the microneedle is made of water soluble matrix materials that encapsulate biodegradable polymer microparticles that in turn encapsulate the API. Upon insertion in the skin, the microneedle separate quickly from the backing (by bubble or effervescence) and the microneedle itself also relatively quickly dissolves, leaving microparticles in the skin, which slowly biodegrade and release the API.

Microneedle Patches

The microneedle arrays described above may be combined with one or more other components to produce a microneedle patch, such as a patch that can be manually applied to a biological tissue, e.g., the skin, of a patient. For example, the microneedle array may be combined with an adhesive layer, which may be used to facilitate securing the patch to a patient's skin during the period of administration of the substance of interest. A backing or handle layer may further be included to facilitate handling of the patch, as described above and illustrated in FIGS. 3A-3B.

The backing layer may be made out of a variety of materials, and may be the same or different than the tab portion. In some embodiments, the backing layer may be a composite material or multilayer material including materials with various properties to provide the desired properties and functions. For example, the backing material may be flexible, semi-rigid, or rigid, depending on the particular application. As another example, the backing layer may be substantially impermeable, protecting the one or more microneedles (or other components) from moisture, gases, and contaminants. Alternatively, the backing layer may have other degrees of permeability and/or porosity based on the desired level of protection. Non-limiting examples of materials that may be used for the backing layer include various polymers, elastomers, foams, paper-based materials, foil-based materials, metallized films, and non-woven and woven materials.

The microneedle patches may include any one or more of the features and/or configurations described in U.S. Patent Application Publication No. 2017/0050010, which is incorporated herein by reference.

Methods of Making Microneedle Arrays

Embodiments of the manufacturing methods described herein are used to make microneedle arrays, which, generally described, include a base substrate with one or more microneedles extending from the base substrate. Generally speaking, the method includes a molding process, which advantageously is highly scalable. The process entails providing a suitable mold; filling the mold with suitable fluid materials; drying the fluid materials to form the microneedles, the funnel portions if included, and the base substrate; and then removing the formed part from the mold. These filling and drying steps may be referred to herein as "casting." The methods herein may include one or more features, parts, and/or techniques described in U.S. Patent Application Publication No. 2017/0050010, which is incorporated herein by reference.

Figure 6:
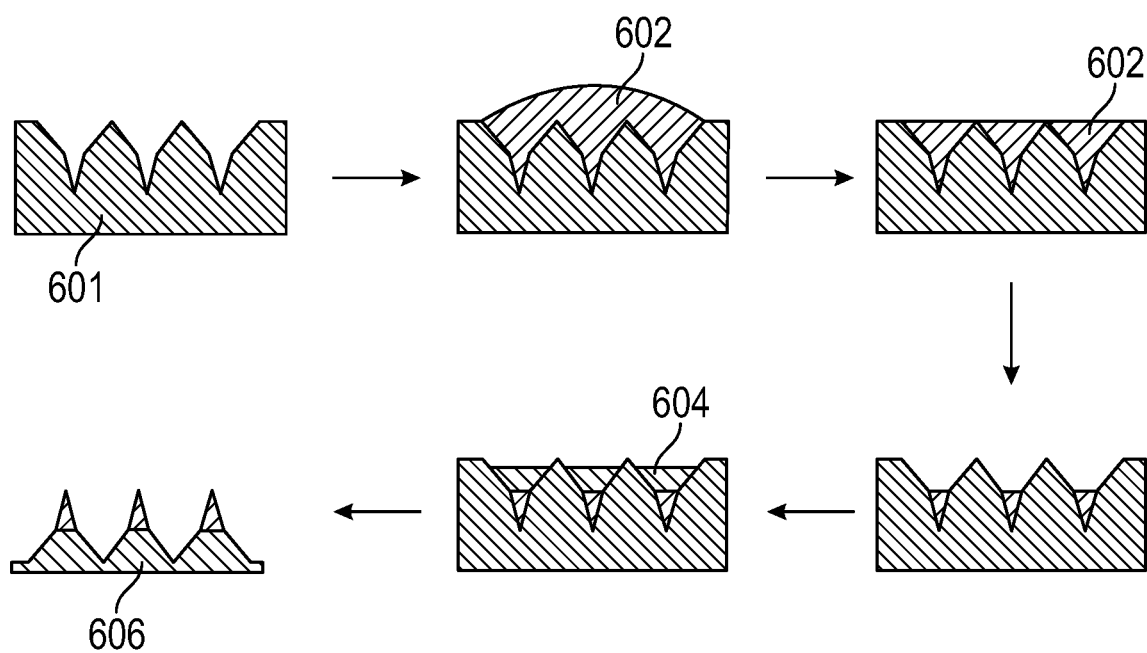
FIG. 6 depicts an embodiment of a process for forming an embodiment of a microneedle array.
Figure 7:
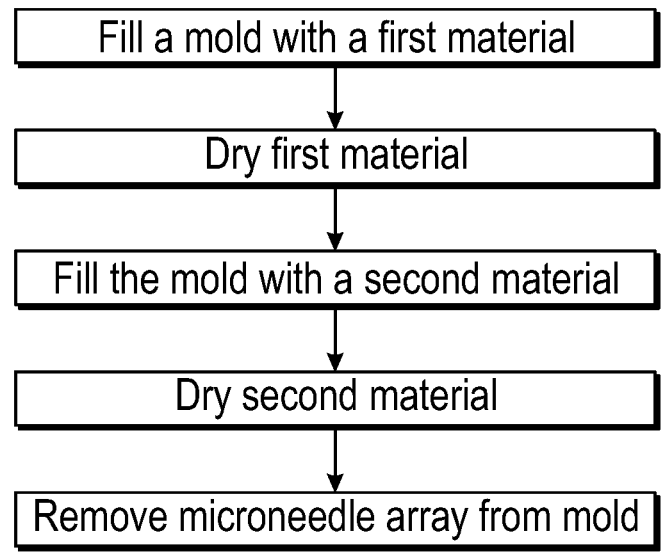
FIG. 7 is a block diagram of one embodiment of a process described herein.

FIG. 6 illustrates one embodiment of a molding process that includes two castings. In this embodiment, a mold 601 is provided and then filled with a first fluid material 602, followed by drying the first fluid material 602 thereby forming microneedles of a microneedle array 606. After which, the mold 602 is filled with a second fluid material 604, followed by drying the second fluid material 604 thereby forming a corresponding funnel portion for each microneedle of the microneedle array 606. The second fluid material includes a matrix material and an effervescent material. The microneedle array 606 is then removed from the mold 601. In a preferred embodiment, the first fluid material 602 includes a substance of interest, and the second fluid material 604 does not include a substance of interest. A process flow diagram of one method of making the microneedle arrays as described herein is illustrated the block flow diagram shown at FIG. 7.

In some embodiments, the methods include (a) providing a mold having an upper surface, an opposed lower surface, and an opening in the upper surface, wherein the opening leads to a first cavity proximal to the upper surface and to a second cavity below the first cavity, wherein the first cavity defines at least one funnel portion, and wherein the second cavity defines at least one microneedle; (b) filling at least the second cavity, via the opening in the mold, with a first material which includes a first matrix material and a substance of interest that are dissolved or suspended in a first liquid vehicle; (c) drying the first material in the mold to remove at least a portion of the first liquid vehicle to form at least a tip portion of a microneedle in the second cavity, wherein the tip portion includes the substance of interest; (d) filling the first cavity, and the second cavity if any is unoccupied following steps (b) and (c), via the opening in the mold, with a second material which includes an effervescent material and a second matrix material that are dissolved or suspended in a non-aqueous second liquid vehicle; (e) drying the second material in the mold to remove at least a portion of the second liquid vehicle to form (i) the at least one funnel portion, and (ii) any portion of the at least one microneedle unformed following steps (b) and (c), wherein the at least one funnel portion includes the effervescent material and the second matrix material; and (f) removing from the mold the at least one microneedle together with the at least one funnel portion connected thereto, wherein more of the substance of interest is located in the at least one microneedle than is located in the at least one funnel portion.

Figure 8:
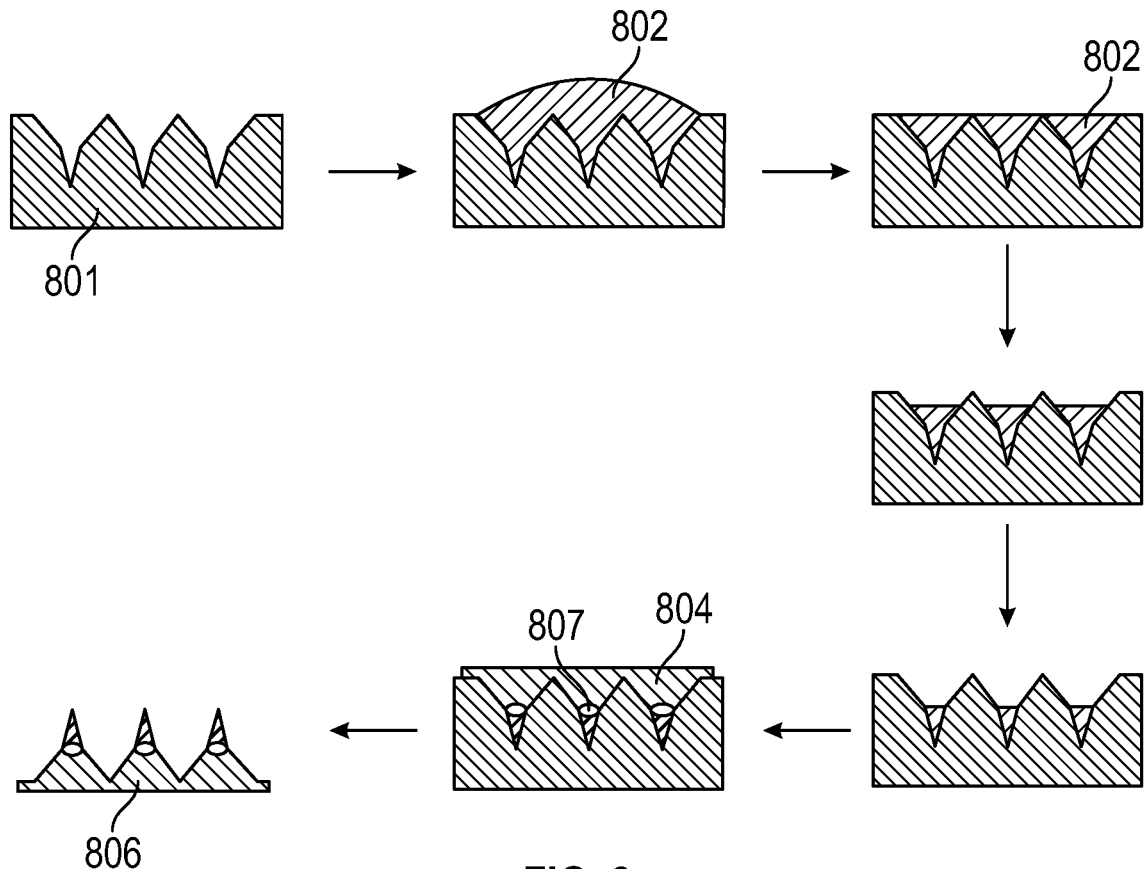
FIG. 8 depicts an embodiment of a process for forming an embodiment of a microneedle.

FIG. 8 illustrates another embodiment of a molding process that includes two castings. In this embodiment, a mold 801 is provided and then filled with a first fluid material 802, followed by drying the first fluid material 802 thereby forming microneedles of a microneedle array 806. After which, the mold 802 is filled with a second fluid material 804, and an air bubble 807 is entrapped between the microneedles and the second fluid material. The second fluid material 804 is then dried, thereby forming a corresponding funnel portion for each microneedle of the microneedle array 806. The second fluid material includes a matrix material. The microneedle array 806 is then removed from the mold 801. In a preferred embodiment, the first fluid material 802 includes a substance of interest, and the second fluid material 804 does not include a substance of interest.

In some embodiments, the methods include (a) providing a mold having an upper surface, an opposed lower surface, and an opening in the upper surface, wherein the opening leads to a first cavity proximal to the upper surface and to a second cavity below the first cavity, wherein the first cavity defines at least one funnel portion, and wherein the second cavity defines at least one microneedle; (b) filling at least the second cavity, via the opening in the mold, with a first material which includes a first matrix material and a substance of interest that are dissolved or suspended in a first liquid vehicle; (c) drying the first material in the mold to remove at least a portion of the first liquid vehicle to form at least a tip portion of a microneedle in the second cavity, wherein the tip portion includes the substance of interest; (d) filling the first cavity, and the second cavity if any is unoccupied following steps (b) and (c), via the opening in the mold, with a second material, and entrapping a bubble of gas between the first material and the second material to form a bubble structure at or near a base end of each of the at least one microneedle, wherein the second material includes a second matrix material that is dissolved or suspended in a second liquid vehicle; (e) drying the second material in the mold to remove at least a portion of the second liquid vehicle to form (i) the at least one funnel portion, and (ii) any portion of the at least one microneedle unformed following steps (b) and (c), wherein the at least one funnel portion includes the second matrix material; and (f) removing from the mold the at least one microneedle together with the at least one funnel portion connected thereto, wherein more of the substance of interest is located in the at least one microneedle than is located in the at least one funnel portion.

Methods for manufacturing microneedle arrays and patches preferably are performed under a minimum ISO 5 (100) process, an ISO 7 process, or an ISO 8 process. Terminal sterilization may be utilized when compatibility of the sterilization method with the active has been demonstrated.

Filling

The composition of the filling solutions generally reflects the desired materials in the final microneedle array, with the exception of the solvents that may be substantially removed during the process.

In a preferred embodiment, the substance of interest is loaded preferentially into the microneedles and their tips, and not into the funnel portions. The substance of interest is part of a filling material that is transferred into the mold. The filling material may also include a liquid vehicle. The filling material may be in the form of a solution, slurry or suspension of particles, melt, powder or particles, or a combination of any of these forms. One or more of these forms may be used in a multi-step filling process. This "filling material" may be referred to herein as a "solution" or as a "fluid material".

In various filling steps, the filling material may include a liquid vehicle. The term "liquid vehicle" may be referred to herein as a "solvent" or a "carrier fluid." In various embodiments, the filling material may include (1) only the solvent, (2) no solvent, (3) only a matrix material, (4) a combination of a solvent and a matrix material with no substance of interest, (5) a combination of only a solvent and a substance of interest, or (6) a combination of a solvent, a substance of interest, and a matrix material. The solvent may be water, an organic solvent, such as a volatile organic solvent, or a combination thereof. Some examples are Class 3 solvents that include acetic acid, heptane, acetone, isobutyl acetate, anisole, isopropyl acetate, 1-butanol, methyl acetate, 2-butanol, 3-methyl-1-butanol, butyl acetate, methylethyl ketone, tert-butylmethyl ether, methylisobutyl ketone, dimethyl sulfoxide, 2-methyl-1-propanol, ethanol, pentane, ethyl acetate, 1-pentanol, ethyl ether, 1-propanol, ethyl formate, 2-propanol, formic acid, and propyl acetate. When a microneedle array includes an effervescent material, the liquid vehicle that includes the effervescent material should be a non-aqueous liquid vehicle. The term "non-aqueous", as used herein, refers to liquids that include less than 1% by volume of water.

The microneedle and funnel cavities may be completely filled, partially filled, or overfilled. After a filling step occurs, it is generally followed by a drying or curing step. The drying or curing step can be achieved by heating or reduction in pressure (e.g., to evaporate solvent), by cooling or elevation of pressure (to solidify matrix material), exposure to light (e.g., polymerization due to ultraviolet light exposure) or combinations of these. This drying or curing step may fully, substantially or only partially dry or cure the deposited material. In general, the solution transfers more of the active into the microneedle and their tips when its viscosity is low, it has high surface energy within the funnel, and is not saturated with active (i.e., active is highly soluble in the solvent). However, none of these three characteristics are required, rather they have been found typically to enable more preferential loading of the microneedles and their tips.

In a preferred embodiment, a two-step filling process is used, wherein the first filling step contains the substance of interest, which substantially migrates into the microneedle and its tip during the drying/curing process. This is followed by a second filling step and a subsequent drying/curing process. This second filling step contains the matrix material (s) that give the microneedles and funnels their mechanical structure and may be overfilled to create the base substrate or part of the base substrate. The second filling step may result in the trapping of an air bubble between the material applied during the first filling step and the material applied during the second filling step.

One embodiment of a process that includes more than two-filling steps is as follows: The molds may be filled with a first solution containing an active (as well as possible excipients), which is then dried. The mold is filled again with the same solution and dried. This can be repeated until the desired quantity of active is loaded into the microneedles. This is followed by one or more final filling steps in which the molds are filled with excipients (which could be the same and or different excipients as in prior fillings) and without active, which provide the microneedles with their mechanical structure once dried.

In one embodiment, the filling solution is provided to have a low viscosity. A fill solution having a relatively low viscosity is more fluid and as it dries it can more easily flow down into the microneedles. In embodiments in which the solution includes the active, it is generally preferred that the viscosity of the solution be less than about 100 cp, more preferably less than about 50 cP, more preferably less than about 10 cP, or more preferably less than about 5 cP. The viscosities of the fill solutions may be modified to control the size and/or shape of a bubble structure.

In one embodiment, a centrifuge or similar device is used to spin the molds to create a force normal and into the molds, creating a gravitational force to drive the solution down into the microneedles as it dries/cures. This process also can useful be to drive larger molecules (e.g., the active) down into the microneedles and their tips while the filling fluid is still in the solution state. The term "larger molecules" is used to mean molecules that are larger than those of the liquid vehicle, or solvent, and can also include nanoparticles, microparticles and other particles made up of many molecules.

In various embodiments, the microneedle molding process includes one or more of the following steps before, during and/or after any or all of the mold filling steps: application of vibration, ultrasound, pressure, vacuum, an electromagnetic field, and centrifugation.

Microneedle-by-microneedle filling is difficult using conventional microneedle molds due to the small target size (e.g., leads to misalignment and missing the individual microneedle reservoirs in the mold) and small volume that needs to be deposited (e.g., extremely small deposition volumes will lead to increased variation in the volume deposited). This becomes increasingly difficult in high-volume manufacturing. However, funnel-to-funnel (i.e., depositing filling materials into individual funnel mold cavities) and 'blanket' filling (i.e., covering areas of the mold surface that include multiple individual microneedle/funnel mold cavities) is much easier because the target area can be many times larger than the opening area of an individual microneedle cavity. With funnel-to-funnel filling, the fill volume (i.e., volume of microneedles and funnels) and targeted area (i.e., area of funnel-base interface) advantageously are many times larger than the fill volume and target area of a microneedle alone, so this can greatly reduce variation in the volume deposited (e.g., 5 nl±1 nl is 5 nl±20% and 100 nl±1 nl is 100 nl±1%—a 20-fold difference in the absolute variation in this scenario) and drop-to-target misalignments. With blanket filling, the entire area is covered with solution thereby further reducing the volume and positional constraints. The volume deposited via the blanketing method can be less than, equal to, or greater than the combined volume of the microneedles and funnels. Any excess solution is removed (e.g., wiped, air purged) once the microneedle and funnel cavities are filled.

The volume of solution deposited into the microneedle molds may be controlled by the volume of the cavities within a mold (i.e., completely fill cavity with solution and then clean surface) or the filler (i.e., dispense or load controlled volume, mass, etc.). For microneedle arrays produced by multiple filling steps, these volume control methods may both be used. For example, the solution containing the active is blanket coated over the entire surface, the microneedle and funnel cavities are filled, the solution is cleaned from the surface of the mold, the solution is dried, a second solution is deposited in a controlled amount by a filler, the second solution is dried, etc.

In some embodiments, the second solution includes the matrix material that forms the funnels that contact the base ends of the microneedles, and the volume of the second solution deposited into the microneedle molds is adjusted to control the size of the bubble structures. In some embodiments, increasing the volume of the second solution deposited into a mold reduces the size of the resulting bubble structures. In the embodiment depicted at FIG. 9, second solutions having volumes between 30 and 90 μL created bubble structures measuring 310-105 μm in depth, respectively.

In some embodiments, a fluid handling/dispensing technology/system known in the art to be capable of depositing solutions onto the molds is used. Some are suited for 'blanket' coating (regional or full patch), targeted deposition, or both. Examples of fluid handling/dispensing systems include: syringe or other pumps coupled with dispensing heads (Tecan/Cavro, Gilson, Hamilton), automated pipetting systems (Tecan, Biotek, Eppendorf), screen printing or other mask and clean type systems, slot coating or similar systems, inkjet printing systems (MicroFab), pin or capillary array dispensing technologies, active capillary systems (Nanodrop by Innovadyne), aerosol or spraying based systems, dipping, brushing, stamping, surface chemistry controlled deposition (PRINT—Particle Replication In Non-wetting Templates), acoustic based systems (Picoliter, Inc.), and any combination of these deposition technologies (e.g., BioJet by BioDot, a syringe pump-inkjet hybrid). The filling heads may be automated and move, the molds may move, or both may move, in order to deposit the solutions in the desired locations. This may be in the form of single-cavity molds, multi-cavity mold plates, or on a continuous reel-to-reel process.

A number of drying and/or curing methods can be used throughout the manufacturing process. Heat may be applied in the form of a batch process, but it may be preferred to be integrated into a semi-batch or continuous process. Some of the drying methods, which harden the solution by removing the solvent via evaporation, include the application of: 1) heat—through convection, conduction (i.e., hot plate or heated surface), and/or radiation (heat lamp, IR or NIR light), 2) convection—dry, desiccated, sterile air or nitrogen blower, 3) vacuum—exposure to reduced pressure, 4) ambient drying, 5) desiccation, 6) lyophilization or freeze drying, 7) dielectric drying (e.g., RF or microwaves), 8) supercritical drying, and 7) a combination of one or more these drying methods.

A number of the curing methods (hardening of the substance results from polymerization/cross-linking or reversible polymerization/cross-linking of polymer chains) are brought about by electron beams, heat, or chemical additives/reactions. Curing triggers may include time ultraviolet radiation (e.g., UV light), pressure, heat, etc.

As used herein, the term "drying," "dried," or "dry" as it refers to the material in the mold (e.g., the matrix material and/or the substance of interest) refers to the material becoming at least partially solidified. In embodiments, the microneedles may be removed from the mold before being fully dried. In one embodiment, the microneedles are removed from the mold after the microneedles are dried to be an operational state. However, in a preferred embodiment, the microneedles are removed from the mold when the microneedles are in a rubbery state but strong enough to be pulled or peeled out of the mold. This has been found to improve demolding without microneedle breakage. As used herein, the term "operational state" means that the microneedles are sufficiently rigid to be used for their intended purpose, e.g., to penetrate skin. As used herein the term "rubbery state" means that the microneedles are not in an operational state, as they are too soft and flexible to penetrate their intended target tissue, e.g., skin. For example, a microneedle, such as one comprised of a bulk/matrix material including polyvinyl alcohol and a sugar, would, when undergoing a drying process, enter a rubbery state, as its moisture content is reduced, before entering the operational state.

Methods of Using the Microneedle Arrays

The microneedle arrays and patches provided herein may be self-administered or administered by another individual (e.g., a parent, guardian, minimally trained healthcare worker, expertly trained healthcare worker, and/or others). The microneedle patches provided herein may be directly handled and administered by the person applying the patch without requiring use of an applicator to apply the required force/pressure, thereby allowing for a very simple, low-profile (i.e., thin and patch-like) microneedle patch (e.g., the total patch thickness, including any application aids, does not exceed 2 cm, more preferably 1.5 cm, more preferably 1 cm, and more preferably 0.5 cm).

In some embodiments, the methods of using the microneedle arrays include a simple and effective method of administering a substance of interest with a microneedle patch. The methods may include identifying an application site and, preferably, sanitizing the area prior to application of the microneedle patch (e.g., using an alcohol wipe). If needed, the application site may be allowed to dry before application of the microneedle patch. The patch then is applied to the patient's skin/tissue and manually pressed into the patient's skin/tissue (e.g., using the thumb or finger) by applying a sufficient pressure to insert the one or more microneedles into the patient's skin/tissue.

The microneedles will then separate from the microneedle patch upon dissolution of the funnel portion if the funnel portion includes an effervescent material. When an effervescent material is included in the funnel portion, the microneedles may separate from the microneedle patch within about 10 seconds to about 120 seconds after the microneedle patch is pressed into the patient's skin/tissue. In some embodiments, the microneedles separate from the microneedle about 40 second to about 60 seconds after the microneedle patch is pressed into the patient's skin/tissue.

When the microneedle patch includes bubble structures, a shearing force is applied to the microneedle patch after the microneedle patch is pressed into the patient's skin/tissue. The shearing force may be applied to any part of microneedle patch. For example, the shearing force may be applied by pulling a tab portion. As a further example, the shearing force may be applied by pushing a base structure and/or funnel portion. The shearing force may be applied for a time effective to separate the microneedles from the microneedle patch. The shearing force may be applied in one or more directions. The shearing force may be generated as part of a relatively continuous motion that starts moving substantially perpendicularly to the tissue surface and then changes direction (suddenly or gradually) to a direction substantially parallel to the tissue surface. In this way, a single motion (i.e., pressing on the back of the microneedle array or patch) can initially generate the force to insert the microneedles into the tissue and then generate the shear force to separate the microneedles from the array or patch. In some embodiments, the shear force is applied between 0.01 second and 60 seconds, or between 1 second and 60 seconds following the insertion of the microneedles. In some embodiments, the shear force is applied instantaneously upon insertion of the microneedles.

After separation of the microneedles from the patch, the patch may be removed from the patient's skin/tissue. The patch may be removed by manually grasping and pulling a tab portion (e.g., between the thumb and finger), and discarding the patch. Due to the separation of the microneedles from the patch, the patch may be discarded as non-sharps waste.

In some embodiments, following microneedle separation, the microneedles may dissolve readily (within minutes to tens of minutes). In some embodiments, the microneedles may dissolve, bioerode, biodegrade, and/or be bioabsorbed over days, weeks or months.

In some embodiments, the microneedle patches described herein are used to deliver one or more substances of interest (e.g., vaccines, therapeutics, vitamins) into the body, tissue, cells, and/or organs. In some embodiments, the microneedles are used to deliver the active into skin by inserting the microneedles across the stratum corneum (outer 10 to 20 microns of skin that is the barrier to transdermal transport) and into the viable epidermis and dermis. The small size of the microneedles enables them to cause little to no pain and target the intradermal space. The intradermal space is highly vascularized and rich in immune cells and provides an attractive path to administer both vaccines and therapeutics. The microneedles are preferably dissolvable and once in the intradermal space they dissolve within the biological fluid and release the active into the skin. The microneedles can be formulated to release active over extended periods. The extended period may be at least two weeks, at least four weeks, at least six weeks, at least eight weeks, at least three months, at least six months, at least nine months, or at least a year.

In one embodiment, a method is provided for administering a substance of interest to a patient, which includes providing one of the microneedle arrays described herein; and applying the microneedles of the array to a tissue surface of the patient, wherein the insertion of the microneedles of the array into the skin is done manually without the use of a separate or intrinsic applicator device. In this particular context, the term "applicator device" is a mechanical device that provides its own force, e.g., via a spring action or the like, which serves as the primary force to drive the microneedle array against the tissue surface, separate from any force the user may impart in holding the device and/or microneedles against the tissue surface.

Unless otherwise defined herein or below in the remainder of the specification, all technical and scientific terms used herein have meanings commonly understood by those of ordinary skill in the art to which the present disclosure belongs. It is also to be understood that the terminology used herein is for the purpose of describing particular embodiments only, and is not intended to be limiting. In describing and claiming the present embodiments, the following terminology will be used in accordance with the definitions set out below.

As used in this specification and the appended claims, the singular forms "a," "an," and "the" include plural referents unless the content clearly dictates otherwise. Thus, for example, reference to "a component" can include a combination of two or more components; reference to "a buffer" can include mixtures of buffers, and the like.

The term "about", as used herein, indicates the value of a given quantity can include quantities ranging within 10% of the stated value, or optionally within 5% of the value, or in some embodiments within 1% of the value.

EXAMPLES

Example 1—Fabrication of Rapidly Separable Microneedle Patches

The studies explained at Examples 1-6 herein were designed with the objective of developing a microneedle patch with rapidly separable microneedles that slowly released levonorgestrel (LNG) and maintain LNG plasma concentration above the human therapeutic level for one month.

The approach was first to formulate an embodiment of a microneedle patch that met the following criteria: (i) sharp tips and mechanical strength suitable for penetration into skin, (ii) incorporation of a bubble at the microneedle patch backing interface that enables rapid microneedle separation in skin after application of mild shear, (iii) encapsulation of LNG in microneedles formulated to release LNG at a steady rate that maintains LNG plasma concentration above the human therapeutic level for one month, (iv) use of well-established biocompatible materials, (v) generation of no sharps waste, and (vi) expectation of simple and painless self-administration by patients. The resulting microneedle patches were studied in vitro and in vivo in rats to assess the ability of the patch to meet these criteria.

Polydimethylsiloxane (PDMS) molds were used to fabricate the microneedle patches of this example. The microneedles were arranged in a 10×10 array with a center-to-center interval of 600 µm in an area of 7×7 mm, and each microneedle was conical, with a base radius of 150 µm, a height of 600 µm, and a tip radius of about 10 µm. To demonstrate feasibility of scale-up to a human dose, also fabricated were patches containing 20×20 arrays of microneedles, which could be inserted and detached into skin, and contained 1.52±0.08 mg LNG per patch.

The patch backing contained an array of pedestals (base diameter 600 µm, top diameter 150 µm and height 350 µm) that were positioned at the base of each microneedle to elevate the microneedles above the base of the backing.

The microneedles were molded by casting an organic solvent (dioxane/tetrahydrofuran, 70%/25%, v/v) to solubilize poly-lactic acid (PLA), poly-lactic glycolic acid (PLGA), and LNG, and 5% v/v water to slow evaporation during fabrication. Polymer and LNG were filled into mold cavities by centrifugation to form the microneedles and enhance microneedle strength by minimizing void formation. Next, an aqueous PVA/sucrose backing solution was applied to the mold, which entrapped an air bubble due to poor wetting of the dried polymer microneedles by the aqueous backing solution. The resulting microneedle patches (i.e., "bubble-microneedle" patch) included a 10×10 array of microneedles in about 0.5 $cm^2$ mounted on a slightly larger, rigid tape. This patch was designed small enough to simplify transportation/storage, while large enough for convenient patient handling.

Microneedle array fabrication involved sequentially casting two solutions onto the mold. The first casting solution contained 5% (w/v) solids dissolved in a mixture of dioxane/tetrahydrofuran/water (70%/25%/5%, v/v). The solids were composed of PLGA/PLA/LNG (72%/8%/20%, w/w). The formulation containing PLGA:PLA in a ratio of 90:10 was selected so that PLGA would provide primary control over drug release rate, and PLA was added to increase mechanical strength.

Figure 9:
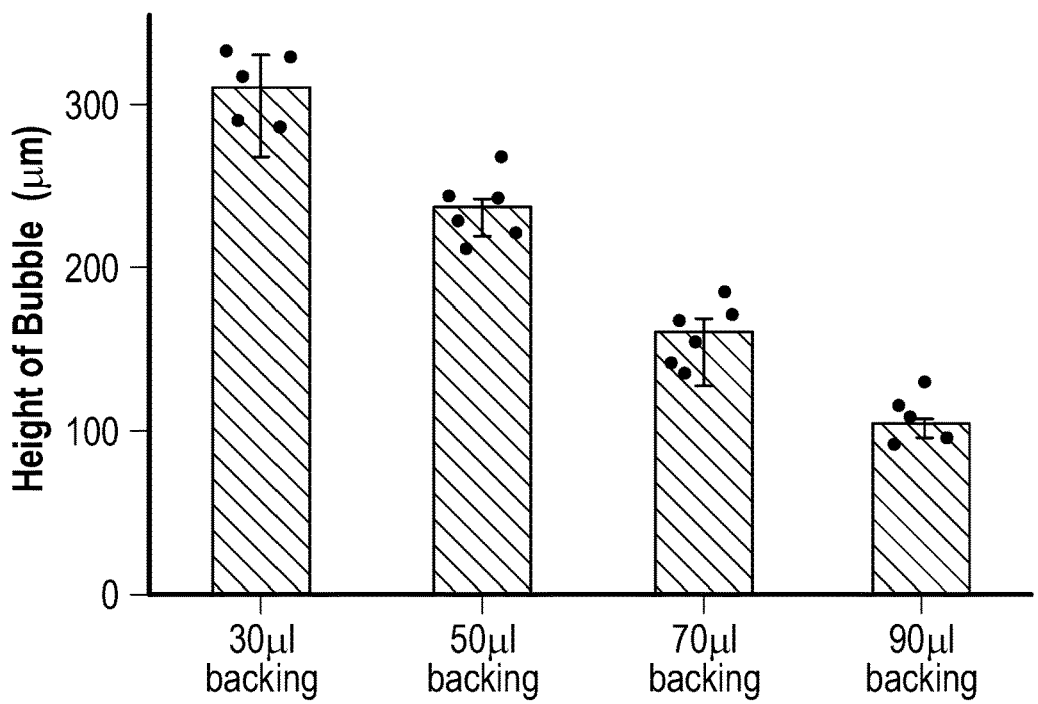
FIG. 9 is a graph depicting a possible correlation between backing solution volume and the size of embodiments of bubble structures.

Air bubble size at the base of each microneedle was important to control, because the bubble structure, at least in part, determined mechanical strength of the microneedle-backing interface. Bubble size was controlled by adjusting the backing solution volume applied during the second cast, because an increased weight of larger amounts of backing solution forced more air from the microneedle-backing interface. Varying backing solution volumes between 30 and 90 µL created bubble structures measuring 310-105 µm in depth (i.e., height, or the distance from the bubble/microneedle interface and the bubble/backing interface), as depicted at FIG. 9. The bubble structures extended into the patch backing pedestals, thereby not altering the size and shape of the microneedles.

Specifically, the casting solution was made by dissolving 0.45 g PLGA (50/50 lactide/glycolide molar ratio, inherent viscosity 0.59 dL/g, Durect, Binningham, AL) and 0.05 g PLA (inherent viscosity 1.02 dL/g, Durect) in 2 mL dioxane (Sigma-Aldrich, St. Louis, Mo.); then adding a solution of 0.125 g LNG (Chemo Industriale Chimica S.R.L, Saronno, Italy) in 3.375 mL tetrahydrofuran (Thermo Fisher Scientific, Waltham, Mass.); and finally mixing them together with additional dioxane and deionized (DI) water to obtain the final casting solution.

To fabricate blank microneedle patches, no LNG was added in the polymer solution which contained 5% (w/v) solids composed of PLGA/PLA (90%/10%, vdw) in dioxane/DI water (95%/5% v/v). To fabricate microneedle patches containing Nile red (Sigma Aldrich), 20 mg Nile red powder was added into the blank casting solution without LNG. Twenty microliters of the casting solution were applied to the top of the microneedle mold and then centrifuged at 3200 g for 2 minutes to fill the mold. Then, 20 µL dioxane was applied to the top of the mold and centrifuged at 3200 g for 2 minutes to wash residual casting solution on the top of the mold into the mold cavities. The loading and washing process was repeated three more times to fully fill the mold, and then the mold was placed in a 60° C. oven with vacuum for 12 hours for drying.

The second casting solution, including 18% (w/v) PVA (MW 6000 Da, Sigma-Aldrich) and 18 (w/v) sucrose (Sigma-Aldrich) in DI water, was gently applied to the dried PDMS mold surface to form the patch backing. During this casting, an air bubble could be trapped between each of the microneedles and the pedestals of the patch backing, such that the bubble size was controlled by adjusting the volume (30 μl, 50 μl, 70 μl, 90 μl) of the second casting solution. After drying in a chemical hood for 2 hours, the mold was placed in a desiccator for 2 days at room temperature (20-25° C.) for complete drying, after which the patch was peeled from the mold and stored in a desiccator until use.

The microneedles were made of PLGA, which facilitated controlled LNG release as explained in the following examples, and a small amount of PLA, which was used to impart additional mechanical strength to the microneedles. While essentially all LNG was released in vivo within two months, in the examples, some biodegradable polymer may have remained in the skin. The relevant literature indicates that PLGA and PLA should biodegrade on a timescale of months or a year, respectively, to oligomers and monomers of lactic and glycolic acid, which can be safely cleared from the body. The total amount of PLGA and PLA in the microneedle arrays here was about 1.1 mg and about 0.1 mg, respectively. For comparison, the amount of PLGA in Lupron Depot, which has been safely administered to patients since FDA approval in 1995, is about 33 mg and the amount of PLA in Lupron Depot-PED is about 99 mg (Lee, B. K. et al., *Adv. Drug Deliv. Rev.* 107, 176-191 (2016)). Therefore, PLGA/PLA administered by these microneedle arrays/patches should be safely cleared from the body.

Example 2—Microneedle Patch Mechanical Properties

Figure 10:
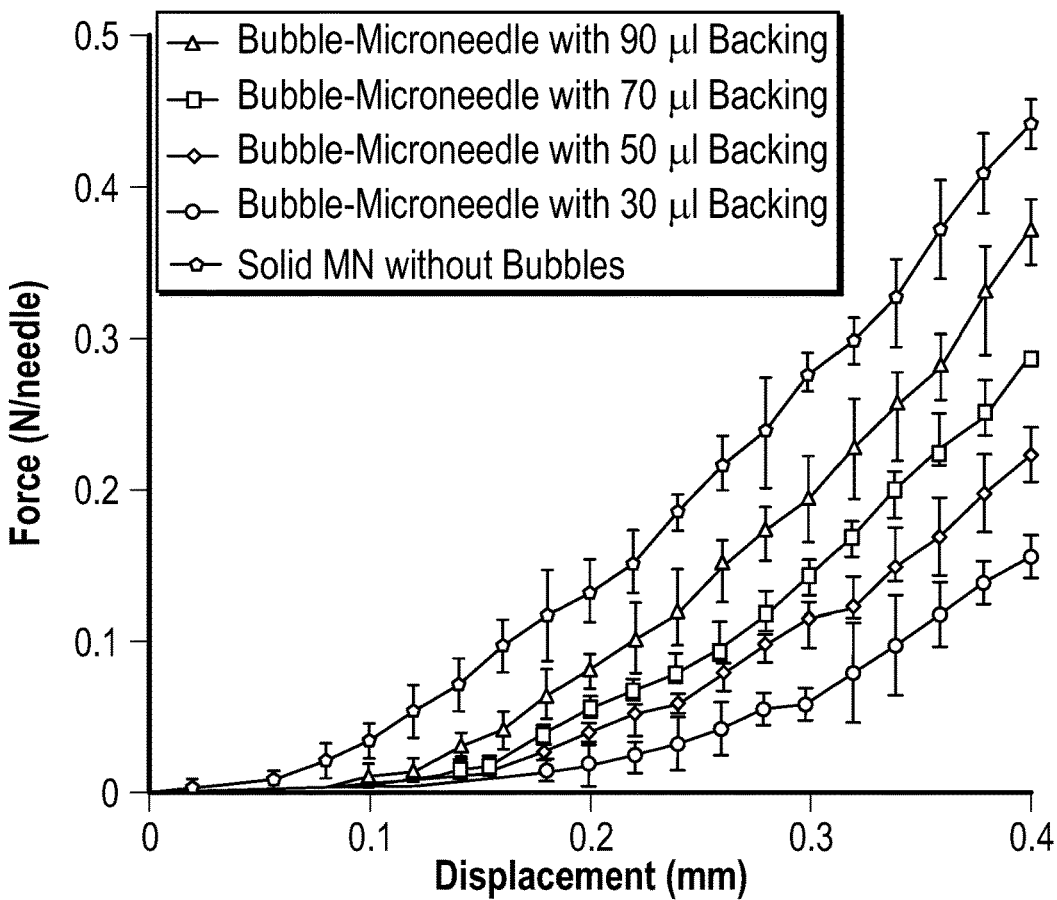
FIG. 10 is a graph depicting the mechanical behavior of embodiments of bubble-microneedle patches under compression administered by a vertical force.
Figure 11:
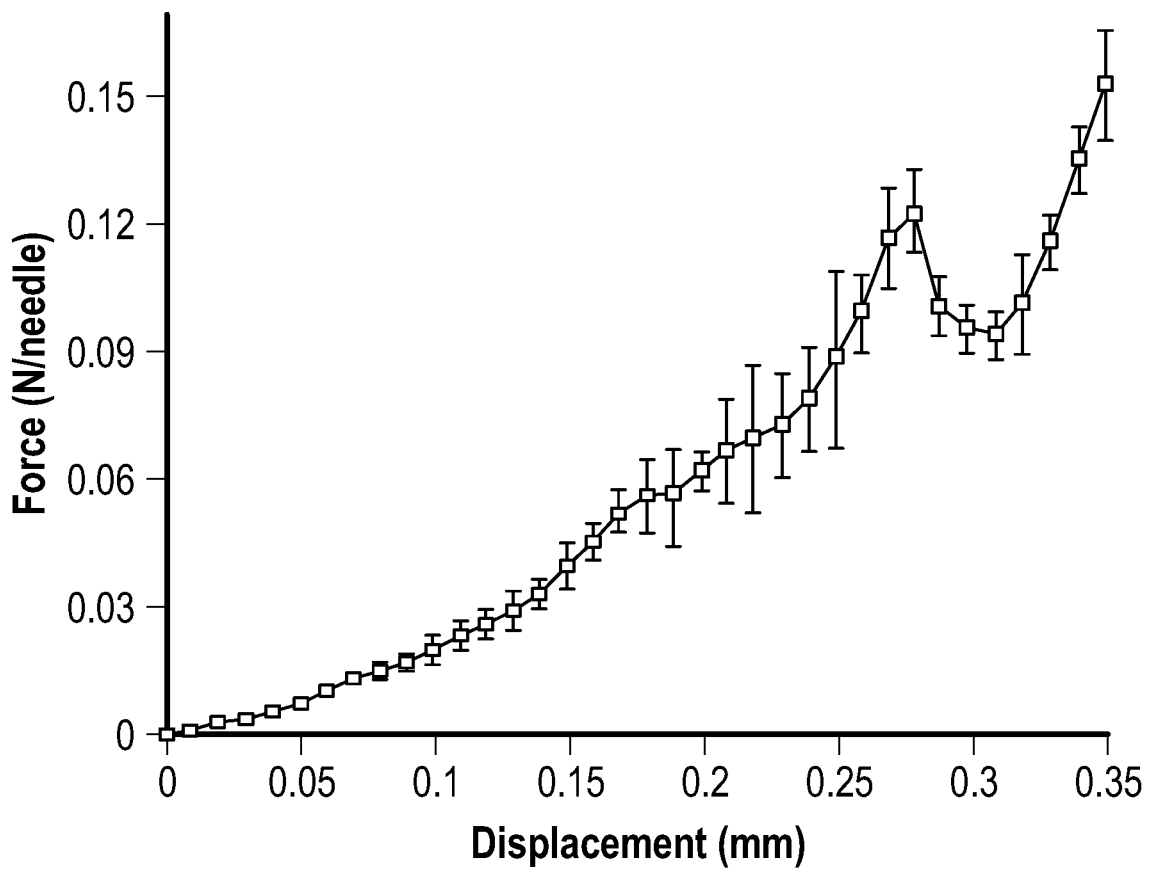
FIG. 11 is a graph depicting the mechanical behavior of embodiments of individual microneedle containing a 240 µm bubble structure.

Tests were conducted to investigate whether the bubble-microneedle patches of Example 1 had sufficient mechanical strength to penetrate skin under compression but still detach in skin under mild shear. It was determined that microneedle strength during compression decreased with increasing bubble size when measured using 100-microneedle arrays, as depicted at FIG. 10, and individual microneedles, as depicted at FIG. 11.

Although the bubble-microneedles of Example 1 were weaker than solid-microneedles (without bubbles), the microneedles with the largest bubbles (i.e., 30 backing solution/310 μm bubbles) tolerated compressive forces of 0.05-0.08 N/microneedle, which is expected to permit skin puncture without breaking (see Prausnitz, M. R., Adv. Drug Deliv. Rev. 56, 581-87 (2004)).

Figure 12:
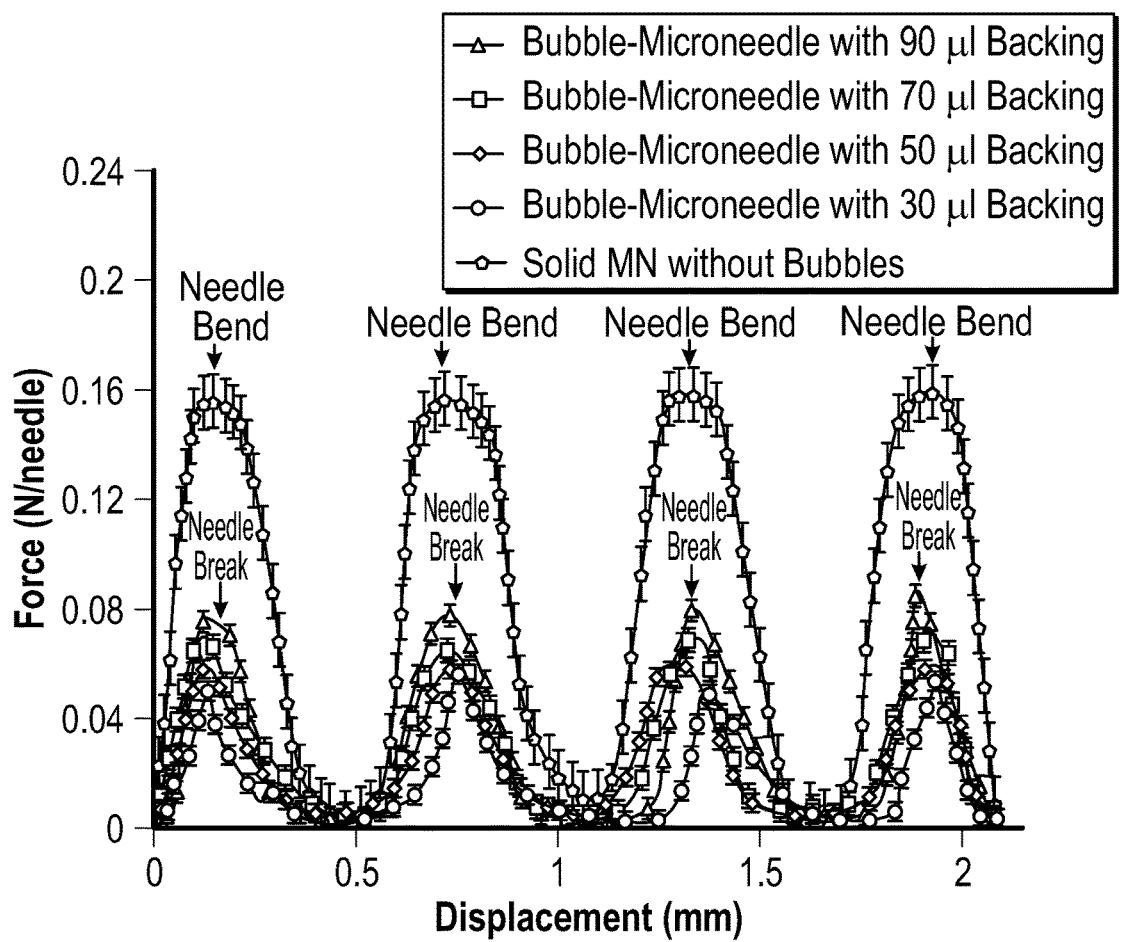
FIG. 12 is a graph depicting the mechanical behavior of embodiments of bubble-microneedle patches under shear administered by a horizontal force.

In contrast, bubble-microneedles were easily broken under shear forces of 0.05-0.08 N/needle, as depicted at FIG. 12, which is a force that can easily be applied by hand. Solid-microneedles required shear of 0.157±0.001 N/needle to deform, and these solid microneedles bent without fracture, indicating that shear force would not break off microneedles in skin without the bubbles.

Specifically, the mechanical properties of solid microneedles and rapidly separable microneedles of Example 1 containing bubble structures with different sizes were measured by a displacement-force test station (Force Gauge, Mark-10, Copiague, N.Y.).

To test the microneedle patches under compression, a single patch was attached to a rigid stainless-steel platform positioned vertically (with the microneedles facing upward), and the test station sensor probe approached the microneedles in the vertical direction at a speed of 0.1 mm/s. The initial distance between the sensor and microneedle tips was 1 cm; displacement and force measurements began when the sensor first touched the microneedle tips and continued until the sensor travelled 0.4 mm from the microneedle tips toward the patch backing.

To test microneedle patches under shear, a single microneedle patch was attached to a rigid platform positioned horizontally (with the microneedle facing to the side). The starting position was 1 cm away from the top row of microneedles, and the sensor approached the microneedles in the vertical direction at a speed of 0.1 mm/s; displacement and force began when the sensor first touched the microneedles and continued until the sensor travelled 2.1 mm parallel to the patch backing.

Example 3—Skin Insertion of Microneedle Patches Ex Vivo

Figure 13:
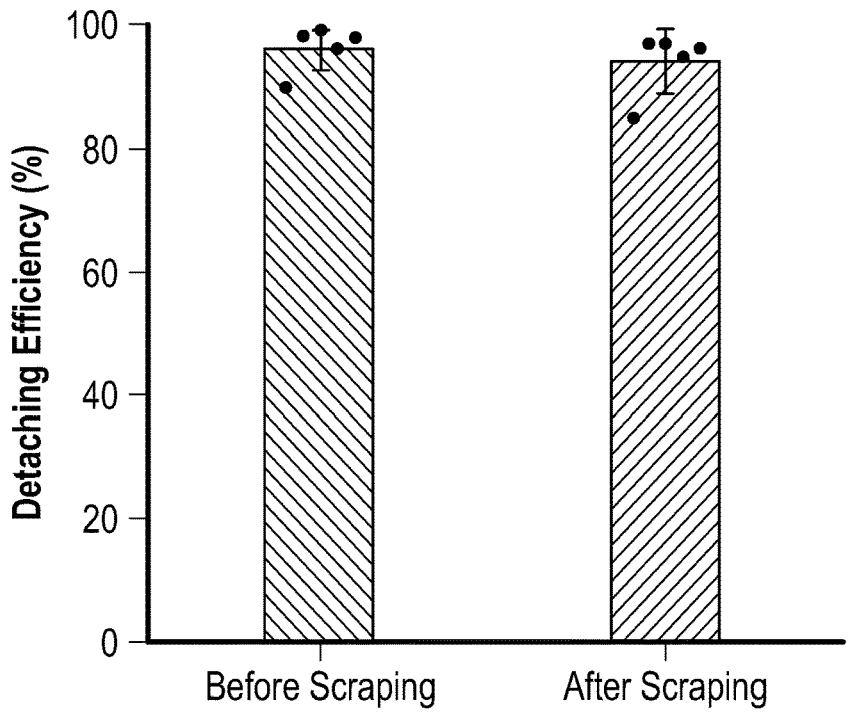
FIG. 13 is a graph depicting the detaching efficiency of embodiments of microneedles before and after a scraping test.

To determine if microneedles could rapidly separate from the base when applied to skin, bubble-microneedle patches were pressed into porcine skin. Microneedles were loaded with Nile red dye for visualization. Microneedles penetrated the skin and, after applying gentle shear (~0.07 N/needle) by thumb 5 seconds after patch application, the microneedles detached from the patch backing and remained embedded in skin. After microneedle separation, there was little residual red dye in the patch, further demonstrating efficient delivery of microneedles into skin. Histological sections showed that microneedles separated fully within the skin below the skin surface. Gently and repeatedly scraping sites of microneedle patch treatment with a swab showed that microneedles were not removed from the skin, as depicted at FIG. 13. FIG. 13 depicts a quantification of microneedle detaching efficiency before and after the scraping test. There was no significant difference between the two data points (Student's t-test, $p > 0.05$). The data indicated that the detached microneedles in the skin were not significantly removed by scraping the skin surface with a swab. Each point represents mean±S.D. (n=5).

Figure 14:
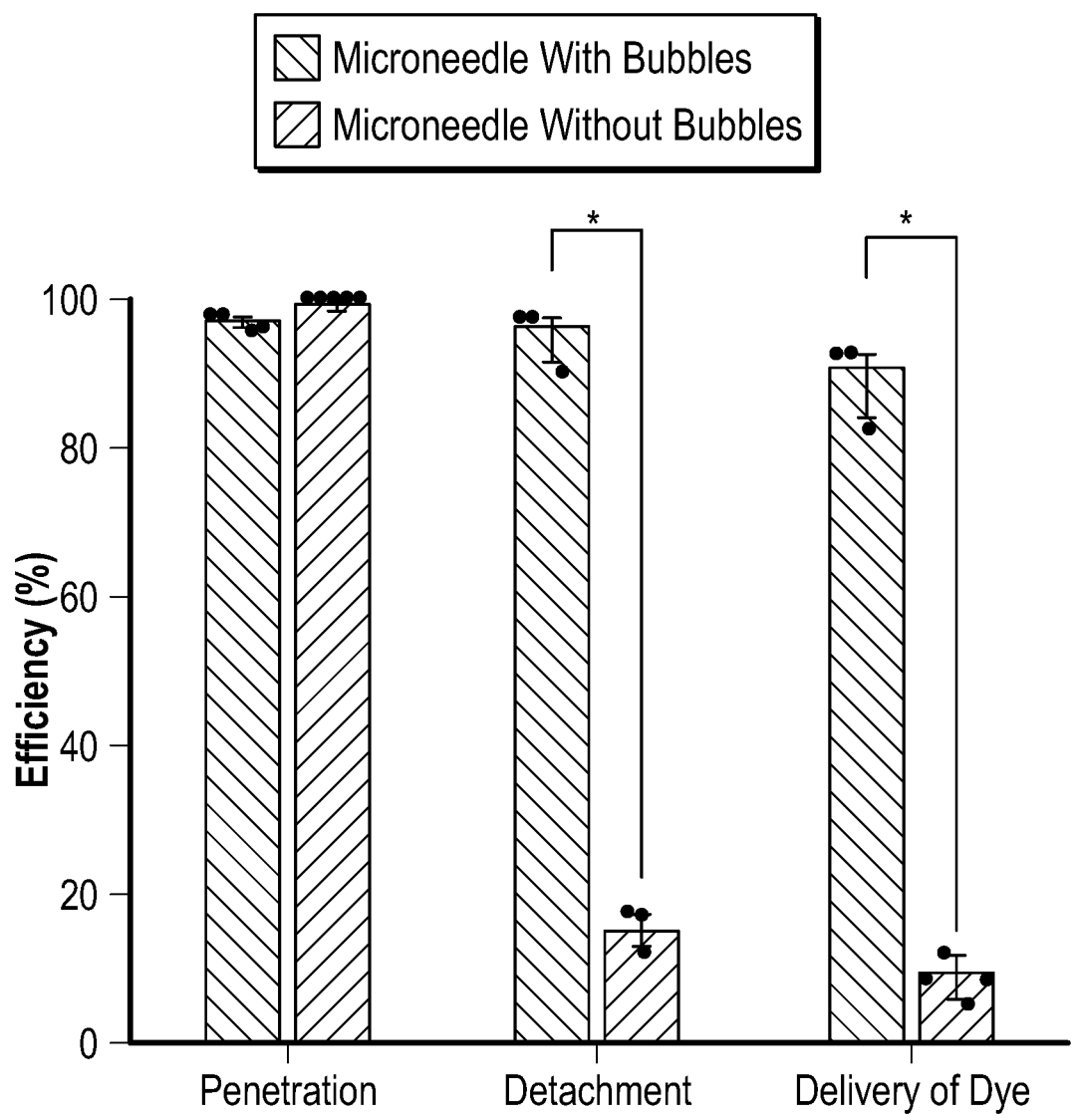
FIG. 14 is a graph depicting the efficiency of penetration, detachment, and delivery for embodiments of microneedles.

Although about 100% of the microneedles penetrated the skin, >95% of the bubble-microneedles detached from the patch backing and >90% of encapsulated dye (simulating encapsulated hormone) was delivered into skin (FIG. 14). In contrast, only 15 of solid-microneedles detached and <10% of dye was delivered into the skin. These results demonstrated rapid and efficient separation and high delivery efficiency of the bubble-microneedle patches of this example. FIG. 14 depicts a quantification of the efficiency of microneedle penetration, microneedle detachment, and microneedle delivery of dye from microneedle patches with and without bubble structures. Each bar represents mean±S.D. (n=5), * $p > 0.05$.

Specifically, to evaluate penetration, separation, retention and delivery efficiency of the patches of Examples 1 and 2, patches loaded with fluorescent dye (Nile Red) were inserted into stretched porcine skin ex vivo by pressing with a thumb for 5 seconds, and then gently sliding to one side along the skin surface to apply a shear force to separate the microneedles from the patch backing.

After separation, the skin containing separated microneedles was examined by optical microscopy (Olympus, Tokyo, Japan) to identify detached microneedles embedded in the skin. In some cases, a swab was gently and repeatedly scraped across the site of microneedle patch treatment for 10 seconds to remove any detached microneedles that were partially protruding above the skin surface.

To assess the penetration of microneedle patches, patches were applied to the skin using a vertical force only, and then immediately removed. The skin was covered with Gentian Violet solution (Humco, Linden, Tex.) for 10 minutes to stain sites of microneedle penetration, and then cleaned with alcohol swabs to remove residual dye from the skin surface. The penetration, separation, and retention efficiency were calculated by dividing the number of colored spots (i.e., due to Gentian violet staining or presence of fluorescent MNs in the skin) by the number of microneedles in the patch (i.e., 100 microneedles).

Microneedle patches were applied to skin manually in order to better simulate actual use. To estimate the forces applied during insertion and detachment, an investigator pressed his or her thumb against the force gauge with a force similar to what was applied to the microneedle patches. The compressive force during microneedle patch insertion and the shear force during microneedle detachment were estimated to be about 0.25 N/needle and about 0.07 N/needle, respectively.

To evaluate delivery efficiency of the microneedle patch, fluorescence intensity from dye in the microneedle patch before and after skin insertion, as well as fluorescence from dye on the skin surface, were measured by quantitative image analysis (Microplate Reader, Bio-Rad, Hercules, Calif.). The dye delivered in the skin was quantified by subtracting the amount of dye in the residual backing and on the skin surface from that in the microneedle patch before insertion. Delivery efficiency was calculated by dividing the delivered dye in the skin by the amount of dye in the microneedle patch before insertion. Finally, skin was frozen and then cut into 10 µm sections for histological analysis.

Example 4—Levonorgestrel Release from Microneedle Patches In Vitro

Figure 15:
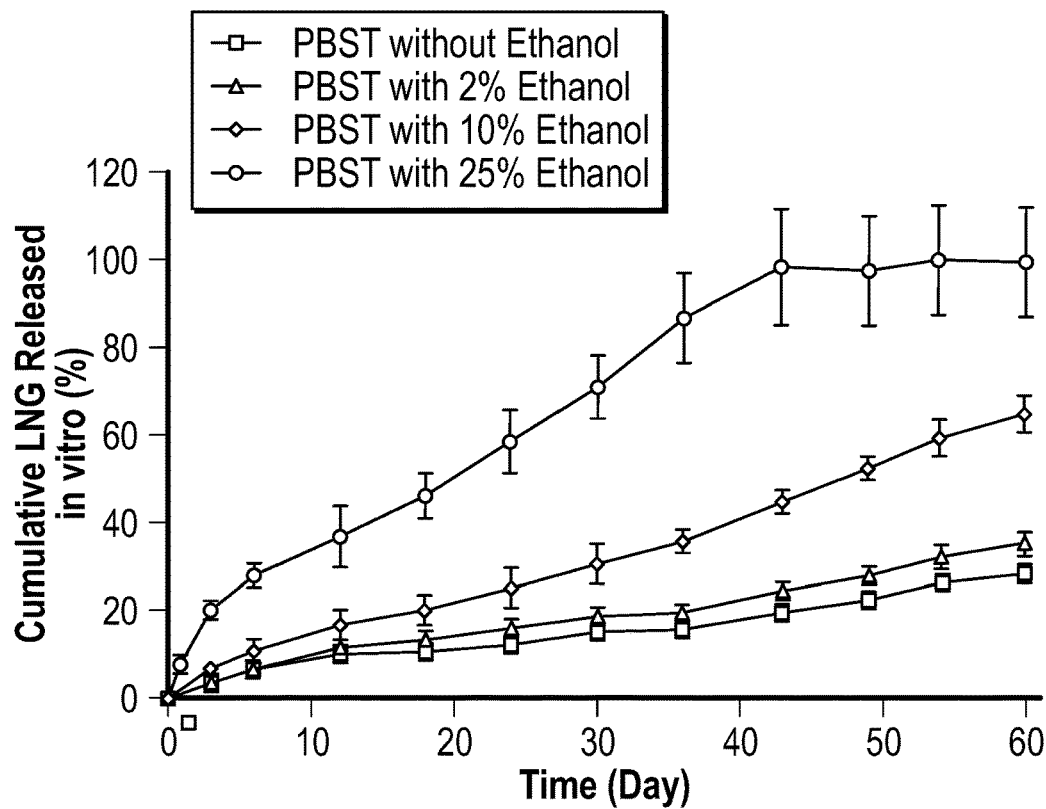
FIG. 15 is a graph depicting the cumulative amount of a contraceptive hormone released in vitro by embodiments of microneedle patches.

LNG release from bubble-microneedle patches of Example 1 was performed in vitro using a saline release media containing 0-25% ethanol, which was added to better simulate in vivo release kinetics, which is often faster than release in vitro. LNG release showed no initial burst release on day 1 (FIG. 15), and LNG release kinetics were fairly constant over time (ranging from about 0.3% to about 2.2% LNG released per day, depending on ethanol concentration). Using 25% ethanol, all LNG was released within 45 days. These data indicated that sustained release of LNG from bubble-microneedle patches is possible and can achieve a target delivery timeframe of at least one month.

In addition, microneedle patches were made by encapsulating LNG in microneedles made of highly water-soluble PVA/sucrose. These microneedles exhibited burst release of 60-90% of LNG, and all LNG was released within 6 to 12 days. All LNG was not released immediately, likely due to slow dissolution of sparingly water-soluble LNG, as opposed to resistance from the highly water-soluble PVA/sucrose microneedle matrix.

Specifically, to evaluate in vitro release of LNG from microneedle patches and predict release of LNG in vivo, PBST was used with different concentrations of ethanol as the release medium. Specifically, one microneedle patch was placed into 1 L PBST (with varying concentrations of ethanol) in a glass vessel.

The PBST solution contained 137 mM NaCl, 2.68 mM KCl, 10.14 mM $Na_2HPO_4$, 1.76 mM $KH_2PO_4$, and 0.02% (w/v) Tween-80; ethanol was added to PBST to a final concentration of 0%, 2%, 10% or 25% (v/v) ethanol. The glass vessel was incubated in a shaker water bath at 37° C. and shaken at 80 rpm. At predetermined time points (0, 1, 3, 6, 12, 18, 24, 30, 36, 43, 49, 54, 60 days), 1 mL release medium was collected and replaced with the same amount of fresh medium.

Collected samples were analyzed by UPLC-MS (Waters, Milford, Mass.) to quantify LNG concentration. LNG was separated on an Acquity UPLC BEH $C_{18}$ column (100 mm×2.1 mm i.d., 1.7 µm particle size) at 50° C. The mobile phase was a mixture of acetonitrile containing 0.1% formic acid and water containing 0.1% formic acid (8:2 ratio, v/v). The flow rate was 0.3 mL/minute with an injection volume of 10 µL. Detection of LNG was performed by electrospray ionization mass spectrometry in the positive ion mode. The target analyte of LNG ($M+H^+$; m/z=313.4) was used for quantification.

Example 5—Levonorgestrel Pharmacokinetics After Release from Microneedles In Vivo The bubble-microneedle patch of the foregoing examples achieved sustained release of LNG that maintained LNG concentration above the human therapeutic level (200 µg/ml) for one month in rats. Although average LNG plasma concentration was up to about 1 ng/ml, the therapeutic window for LNG was relatively large, and marketed LNG-releasing products generate LNG plasma levels up to 1.5 ng/mL (Sivin, I., et al., Contraception 56, 317-321 (1997)), indicating that elevated LNG plasma concentration was acceptable. The microneedle patches of the foregoing examples could be reformulated to release over shorter (weekly) or longer (biannually) times to address needs of different users. Dosages could be increased (for longer delivery times or to load a dose suitable for human use) by increasing drug loading, microneedle size, number of microneedles, or other parameters.

As demonstrated by the current example and the foregoing example, no burst-release of LNG was observed from the bubble-microneedle patches in vitro or in vivo, although burst-release is commonly seen in other biodegradable-polymer controlled-release systems (Huang, X., et al., *J. Control Release* 73, 121-136 (2001); Wang, J. et al., *J. Control Release* 82, 289-307). It was believed that burst-release did not happen in the bubble-microneedle patches of the examples herein because a film of largely drug-free polymer formed on the microneedle surfaces due to possible solvent migration into the mold that concentrates/precipitates PLGA/PLA at the microneedle-mold interface, faster LNG redistribution within the mold due to its smaller molecular size, and/or possible phase separation into a polymer-rich phase and a polymer-poor phase.

When bubble-microneedle patches of Example 1 (encapsulating hydrophobic Nile red dye) were manually applied to rat skin in vivo and gently sheared after 5 seconds, the microneedles penetrated the skin, broke off from the patch backing and were fully embedded under the skin surface. Fluorescence imaging of the skin surface showed dye release kinetics during microneedle biodegradation in the skin.

Figure 16:
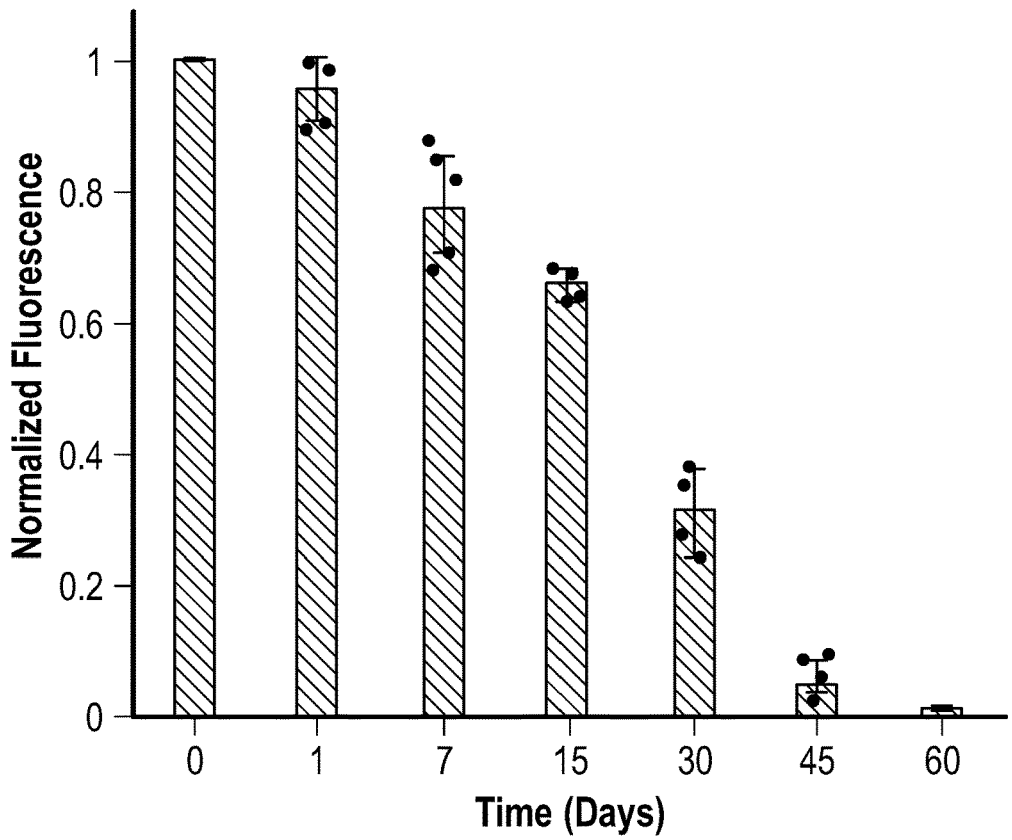
FIG. 16 is a graph depicting the fluorescent intensity of skin after administration of an embodiment of a Nile red-loaded microneedle patch.

An array of fluorescent spots corresponding to microneedles embedded in skin was initially seen, followed by gradual dimming over time. Variable fluorescence intensity at the site of each microneedle may be due to different depths of microneedle insertion into the skin, which resulted in different amounts of skin between each embedded microneedle and the skin surface that absorbed and scattered light. Quantitative analysis similarly showed steady decay in fluorescence, corresponding to slow and continuous release kinetics, with most fluorescence gone after 45 days, as depicted at FIG. 16. These release kinetics mirrored those of LNG release shown in FIG. 18.

In addition, application of a water-soluble microneedle patch made of PVA/sucrose loaded with red dye also generated an array of bright fluorescent spots in skin, but they disappeared within 18 h. This rapid disappearance showed that dye could be cleared from skin within 1 day, but encapsulation in separable PLGA/PLA microneedles extended the release for at least 1 month (see FIG. 16).

Figure 17:
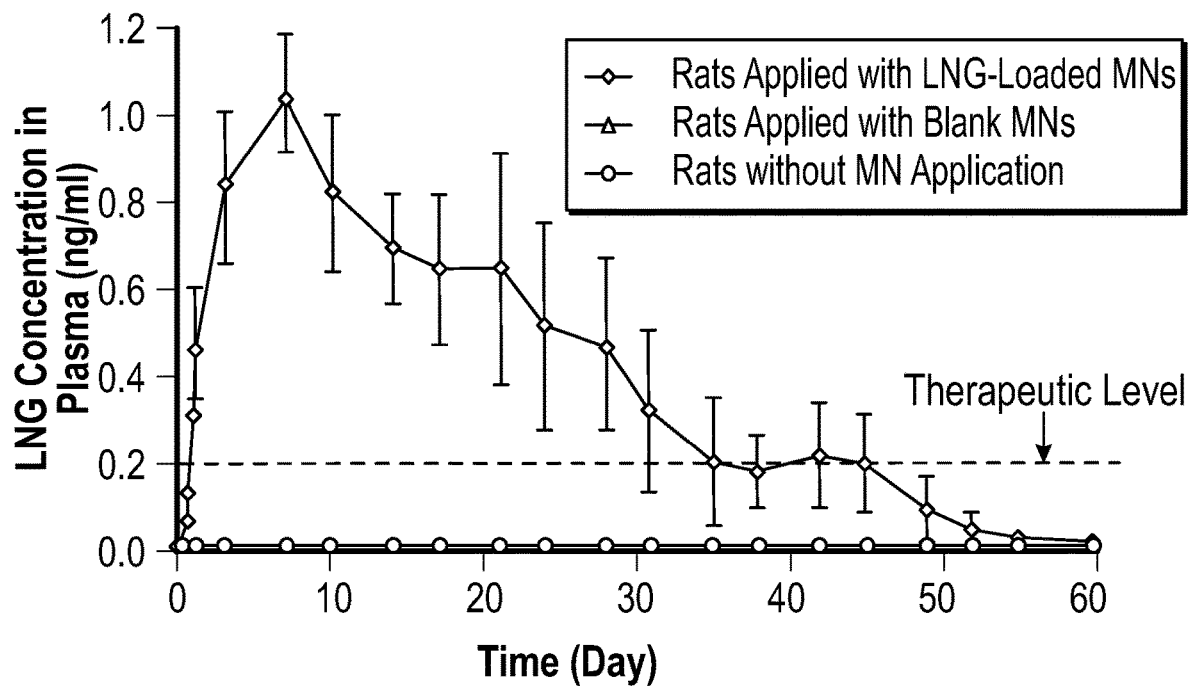
FIG. 17 is a graph depicting the concentration of a contraceptive hormone in plasma upon and after administration of an embodiment of a microneedle patch.

To assess LNG pharmacokinetics from the bubble-microneedle patches of this example, rats were each administered (i) a LNG-loaded bubble-microneedle patch, (ii) a blank bubble-microneedle patch containing no LNG, or (iii) no treatment (FIG. 17). Rats administered LNG-loaded microneedle patches exhibited LNG plasma concentrations that increased to peak concentration ($C_{max}$) of 1.05±0.14 ng/ml (mean±S.D.) at a time ($T_{max}$) of 6.0±1.9 days post-application.

TABLE 1

S1 Mean ± SD levonorgestrel pharmacokinetic parameters following intravenous injection or LNG-loaded microneedle patch administration.

| PK Parameters | LNG intravenous injection | LNG-loaded MNs patches administration |
|---|---|---|
| $T_{max}$ (h) | NA | 144 ± 46 |
| $C_{max}$ (ng/mL) | NA | 1.05 ± 0.14 |
| $AUC_{(0-t)}$ (ng*hr/mL) | 17.2 ± 0.3 | 595 ± 140 |
| $AUC_{(0-inf)}$ (ng*hr/mL) | 17.2 ± 0.3 | 598 ± 141 |
| Half-life (hr) | 20.7 ± 0.6 | 99.2 ± 12.6 |
| Ke ($hr^{-1}$) | 0.034 ± 0.01 | 0.0071 ± 0.0009 |
| F % | NA | 69.6 ± 16.4 |

$C_{max}$: Maximum plasma concentration. $T_{max}$: Time of $C_{max}$. $AUC_{(0-t)}$: Area under the concentration-time curve from time zero to time of last detection. $AUG_{(0-inf)}$: Area under the concentration-time curve from time zero to infinity. The elimination rate constant ($K_e$) of LNG was estimated using the terminal phase of the plasma concentration versus time profile following intravenous LNG injection in the control group, and the data were fit by log-linear regression to estimate the slope ($K_e$). Half-life = 0.693/Ke. % F (Bioavailability) = 100*[$AUC_{MN}$*$Dose_{IV}$]/[$AUC_{IV}$*$Dose_{MN}$]. IV injection dose = 0.006 mg/rat of 200 g each. Microneedle dose = 0.3 mg/rat of 200 g each. NA: Not applicable.

Afterward, LNG levels slowly decreased, remaining above 200 µg/ml (which is the therapeutic level in humans) for 30 days, then hovered near the therapeutic level until 45 days, after which LNG concentrations dropped to insignificant levels by 60 days.

Figure 18:
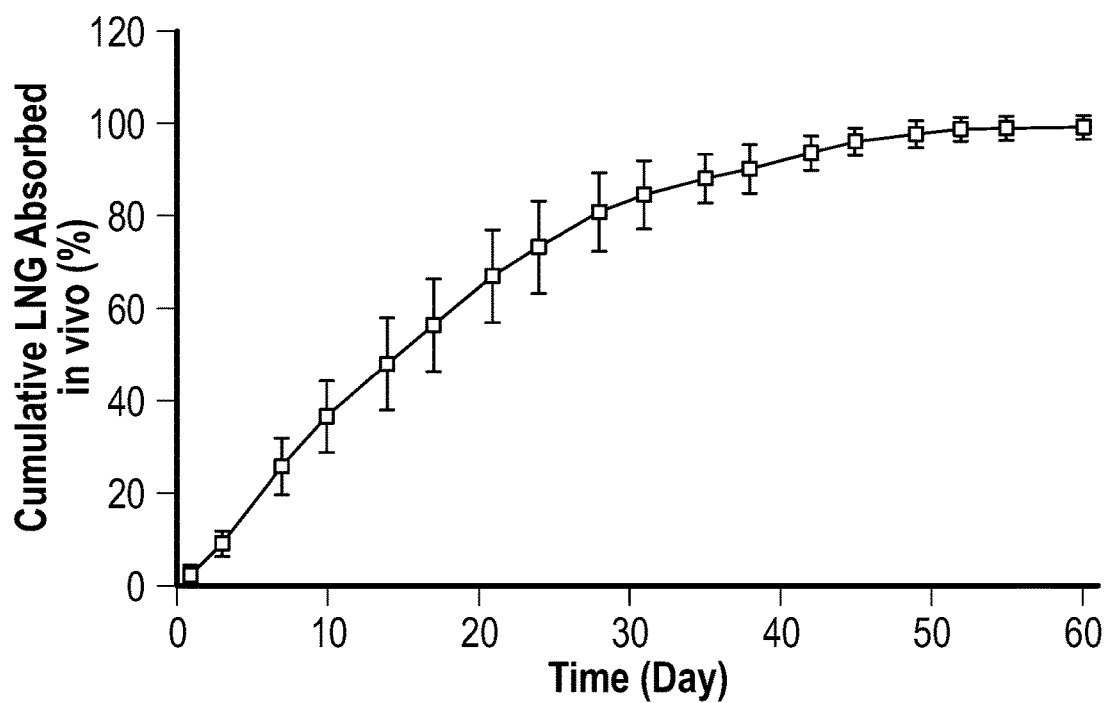
FIG. 18 is a graph depicting the cumulative amount of a contraceptive hormone absorbed in vivo after administration of an embodiment of a microneedle patch.

Pharmacokinetic analysis showed relatively faster LNG absorption for the first 30 days, followed by slower absorption with >95% absorption after 45 days (FIG. 18). This slow, continuous LNG absorption profile in vivo was similar to LNG release kinetics in vitro (using 25% ethanol release media, FIG. 15) and for dye release in vivo (FIG. 16). The in vivo LNG release profile was also similar to the target kinetics for a once-per-month contraceptive patch. Area-under-the-curve for LNG delivery from bubble-microneedles (AUC) of 598±141 ng·h/mL (FIG. 17, Table 1) indicated 70% bioavailability compared to intravenous LNG injection (Table 1). Rats receiving blank microneedle patches or no treatment did not achieve LNG concentrations above background noise.

Bubble-microneedle patch administration of LNG was well tolerated by rats, without erythema, edema or other signs of irritation during the 60-day study. Histological analysis after study completion showed no evidence of changes in skin architecture, inflammatory cells or other signs of tissue damage.

Specifically, LNG pharmacokinetics were evaluated in adult female Sprague Dawley rats (200±12 g) by applying a LNG-loaded microneedle patch to each rat while under isoflurane anesthesia. The rats' dorsal skin was shaved before application of microneedle patches, taking care not to damage skin during shaving.

To investigate polymer biodegradation and release of dye from PLGA/PLA microneedles in rats, microneedle patches containing Nile red were administered to the rats using the methods described above for ex vivo microneedle patch application to porcine skin, after which rats were imaged by fluorescence microscopy (Olympus) using a consistent imaging setup for all rats (e.g., fluorescence excitation light intensity, image capture exposure time) on different days after microneedles application (0, 1, 7, 15, 30, 45, and 60 days).

Fluorescence intensity of the microneedles embedded in rat skin was quantified by analyzing fluorescence images using ImageJ (National Institute of Health, Bethesda, MD). As a control group, a water-soluble microneedle patch containing Nile red was applied to rat skin in vivo and kept on the skin for 15 minutes to allow the microneedles to fully dissolve. The rat skin was then imaged at 0, 4, 8, 12, and 18 hours post-administration, and fluorescence intensity was quantified using the same method. As an additional control, a solution containing 10 mg/mL Nile red in dioxane was exposed to ambient light for 18 hours. There was no significant difference in fluorescence intensity of the solution between the exposed sample and (i) a freshly prepared sample or (ii) a similar sample that was left in the dark for 18 h.

To study pharmacokinetics of LNG release from separable microneedles, rats were randomly divided into three groups: the first group received LNG-loaded microneedle patches, the second group received blank microneedle patches (without LNG), and the third group did not receive any microneedle patches. A power analysis indicated that a sample size of 8 rats per group would be sufficient to distinguish pharmacokinetic profiles in animals receiving LNG from those administered a blank microneedle patch (containing no LNG) with 95% confidence.

The primary endpoint of the animal study was LNG plasma concentration above the human therapeutic level for one month. The secondary endpoint was irritation at the site of microneedle patch administration. All data collected in this study were retained; no outliers were excluded. Blood samples (~500 µL) were drawn from the tail vein at different times after microneedle patch application: 0 h, 12 h, 24 h, 3 d, 7 d, 10 d, 14 d, 17 d, 21 d, 24 d, 28 d, 31 d, 35 d, 38 d, 42 d, 45 d, 49 d, 52 d, 55 d, 60 d.

Plasma was then separated by centrifuging blood samples at 2000 g for 15 minutes at 4° C., and underwent subsequent analysis by enzyme-linked immunosorbent assay (ELISA, Thermo Fisher Scientific) following the manufacturer's instruction to determine LNG concentration. To evaluate biocompatibility of LNG delivery from separable microneedle patches, rats were euthanized by $CO_2$ asphyxiation at the end of the study (i.e., 60 days after microneedle patch application) and tissue surrounding the patch application site was excised. This tissue was fixed in 10% neutral buffered formalin for 2 days at 4° C., and then embedded in paraffin after complete dehydration, cut into sections of 5 μm thickness, and stained using hematoxylin and eosin for histological analysis.

Example 6—Pharmacokinetic Analysis

Pharmacokinetic parameters were calculated using non-compartmental pharmacokinetic analysis. Parameters included: $C_{max}$, the observed maximum plasma concentration; $T_{max}$, the time when $C_{max}$ was achieved; $K_e$, the elimination rate constant of LNG, which was estimated by fitting the data from the terminal phase of the plasma concentration versus time profile following intravenous LNG injection in the control group by log-linear regression to estimate the slope ($K_e$); $AUC_{(o-t)}$, the area under the plasma concentration-time curve from time zero to time of last detection using the linear trapezoidal rule; and $AUC_{(o-inf)}$, the area under the curve from time zero to infinity. Bioavailability of LNG delivered from microneedles was calculated from the ratio of dose-normalized AUC values after microneedle patch administration and intravenous LNG injection. The Wagner-Nelson method was used to estimate the percent of LNG absorbed in vivo, and numerical deconvolution was applied to the LNG plasma concentration versus time profiles.

Example 7—Fabrication of Microneedle Patches with Effervescent Backing

When designing the rapidly separable microneedle patches with effervescent backing in this example, PLGA was selected as the microneedle material because the biodegradable polymer is biocompatible, mechanically strong and can be formulated for controlled release for weeks to months. Other materials that may have one or more of these features may be used, however, and are envisioned.

Polyvinylpyrrolidone (PVP) was selected as the backing materials because PVP has fast solubility in water and good mechanical strength, as well as biocompatibility. Other backing materials that may have one or more of these features may be used, however, and are envisioned.

Figure 19:
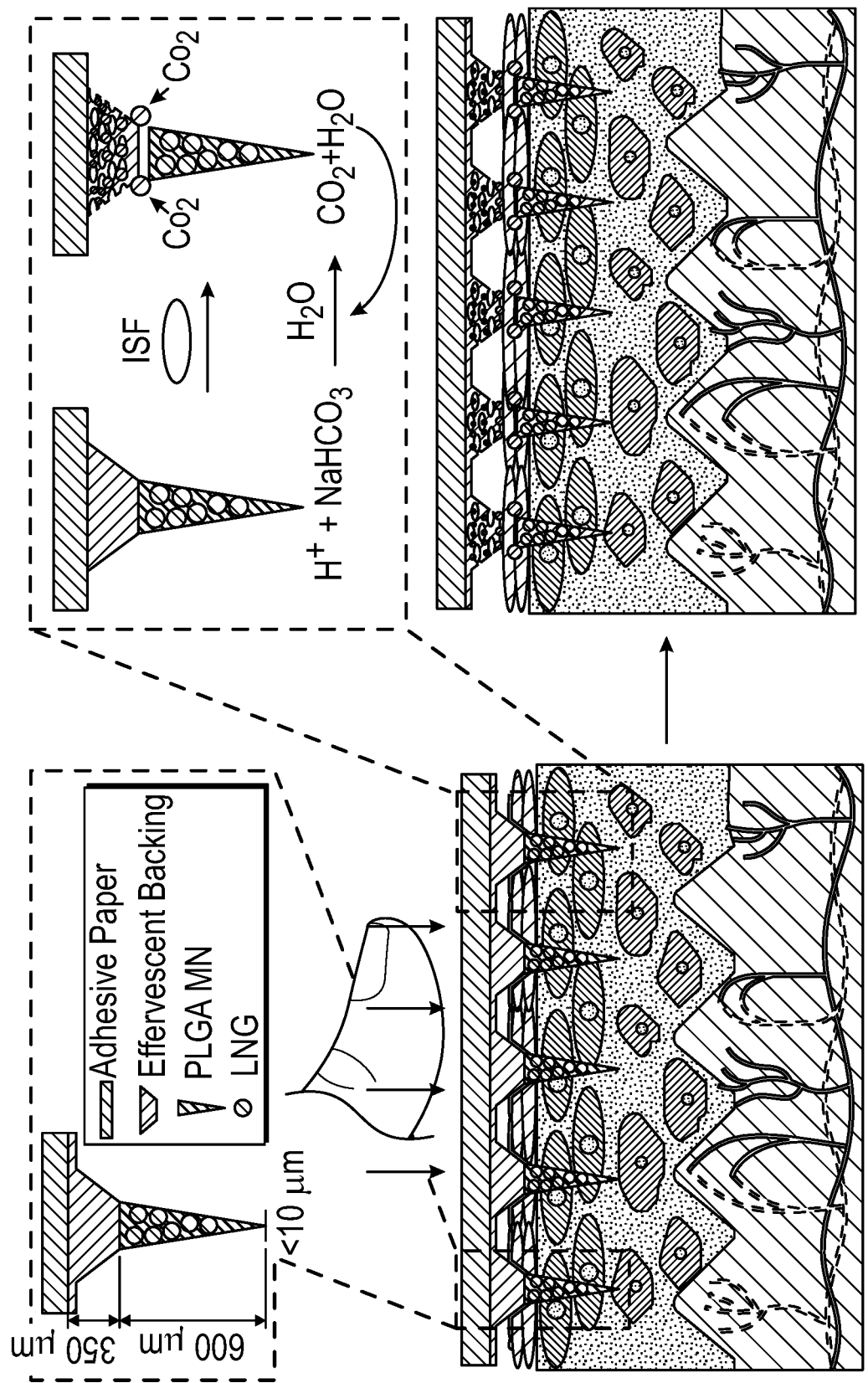
FIG. 19 depicts a schematic illustration of the application into skin of one embodiment of a microneedle patch having an effervescent backing.

To further increase the dissolving speed of backing and achieve rapid separation of microneedles, effervescence (citric acid and sodium bicarbonate) was also formulated with PVP in the backing part (FIG. 19). Once inserted in the skin tissue and contacted with the biological tissue, e.g., interstitial fluid (ISF), under the skin tissue, sodium bicarbonate and citric acid were fast dissolved and immediately reacted with each other, which generated $CO_2$ and water. The produced $CO_2$ made the backing part more porous, and the generated water dissolved more PVP polymer, citric acid, and sodium bicarbonate, and continually stimulated the reaction between the citric acid and sodium bicarbonate, further speeding up the dissolution of the backing polymer and facilitating rapid separation of microneedles.

Figure 20:
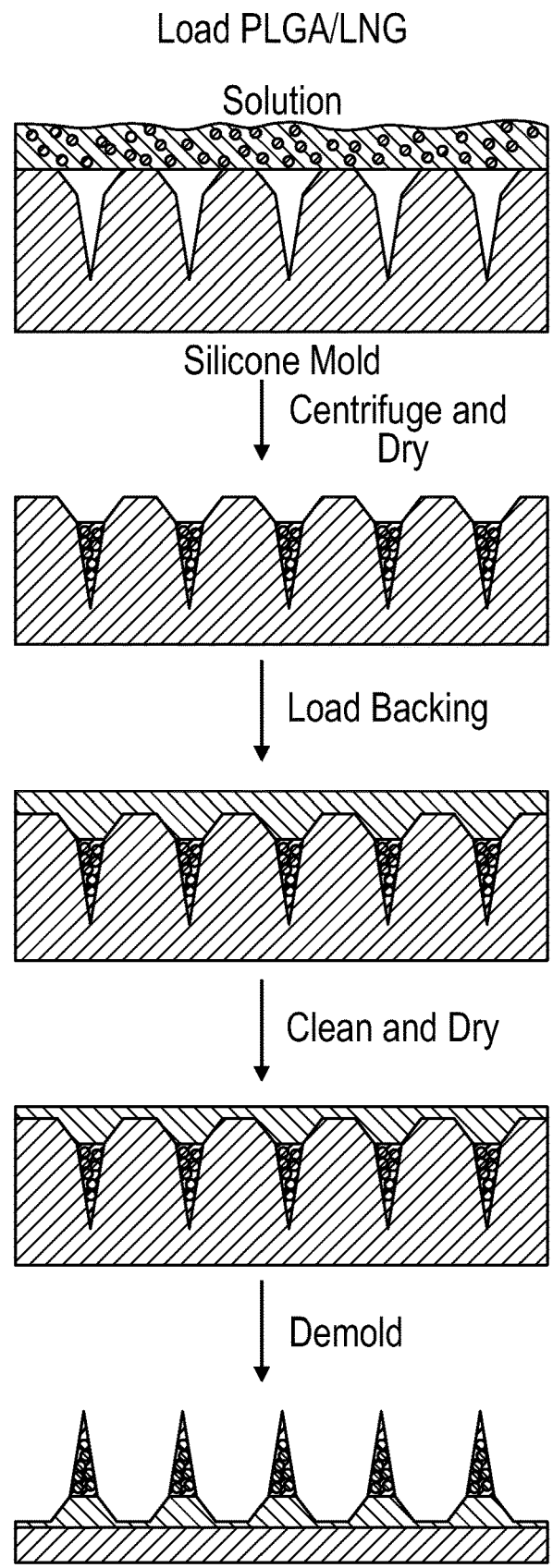
FIG. 20 is a schematic illustration of an embodiment of a fabrication process for producing an embodiment of a microneedle patch having an effervescent backing.

As depicted at FIG. 20, the microneedle patch with effervescent backing was fabricated by casting PLGA solution in diglyme/water (95%/5%, v/v) with suspended LNG crystals. Polymer and LNG were filled in the mold cavity by centrifugation to form the microneedles and enhance microneedle strength by minimizing void formation. After drying the mold, 80 μL of effervescent backing polymer was pipetted on the top of the mold surface, followed by drying in the chemical hood for 1 hour and subsequent demolding.

The resulting patch consisted of a 10×10 array of sharp microneedles in about 0.5 $cm^2$ mounted on a slightly larger, rigid tape and each microneedle was conical with a base radius of 150 μm, a height of 600 μm and a tip radius of ~10 μm. Measurement of mechanical strength by using a force gauge showed a failure force of 0.07 N/needle with the PLGA/LNG patch with effervescent backing, which indicated that the fabricated patch would have sufficient strength to penetrate the skin without breaking.

Specifically, polydimethylsiloxane (PDMS) (Dow Corning, Midland, Mich.) molds were used to fabricate microneedle patches. The microneedles were arranged in a 10×10 array with a center-to-center interval of 600 μm in an area of 7×7 mm, and each microneedle was conical with a base radius of 150 μm, a height of 600 μm, and a tip radius of about 10 μm. The patch backing contained an array of pedestals (base diameter 600 μm, top diameter 150 μm and height 350 μm) that were positioned at the base of each mircroneedle to elevate the microneedles above the base of the backing.

Microneedle patch fabrication involved sequentially casting two solutions onto the mold. The first casting solution contained 10% (w/v) solids dissolved in a mixture of diglyme/THF/water (70%/25%/5%, v/v). The solids were composed of PLGA/LNG (60% /40%, w/w).

To fabricate microneedle patches containing Nile red (Sigma-Aldrich), 20 mg Nile red powder was added into the casting solution. Seven microliters of the casting solution were applied to the top of the microneedle mold and then centrifuged at 3200 g for 20 minutes to fill the mold after waiting 5 minutes. Then 20 μL diglyme/water (95%/5%) was pipetted at the top of the mold, followed by centrifuging at 3200 g for 20 minutes to wash residual casting solution on the top of the mold into the mold cavities. After that, the mold was put in a 60° C. oven with vacuum for 12 hours for drying.

After the first casting in the mold, 80 μL of the second casting solution, which included 13% (w/v) PVP having two molecular weights (360 k/55 k, 50%/50%, Sigma-Aldrich), 4% (w/v) citric acid (Sigma-Aldrich) and 5% (w/v) sodium bicarbonate (Sigma-Aldrich) in pure ethanol, was gently applied to the dried PDMS mold surface to form the patch effervescent backing. For the control groups, the second casting solution included 13% (w/v) PVA (Sigma-Aldrich)/ 13% (w/v) sucrose (Sigma-Aldrich) in water or 13% (w/v) PVP (360 k/55 k, 50%/50%) in ethanol. After drying in the chemical hood for 1 hour, the mold with effervescent backing or normal backing was placed in a desiccator for overnight or 2 days respectively at room temperature (20-25° C.) for complete drying, after which the patch was peeled from the mold and stored in a desiccator until use.

Example 8—Microneedle Patch Mechanical Properties

Mechanical property of rapidly separable microneedle patches with effervescent backing was measured by a displacement-force test station (Force Gauge, Mark-10, Copiague, N.Y.). Briefly, a single patch was attached to a rigid stainless-steel platform positioned vertically (microneedles facing up), and the test station sensor probe moved towards the microneedles in the vertical direction at a speed of 0.1 mm/s. The initial distance between the sensor and microneedle tips was 1 cm; displacement and force measurements began when the sensor first touched the microneedle tips and continued until the sensor travelled 0.4 mm from the microneedle tips toward the patch backing.

Example 9—Detachment Test of Microneedle Patches

Figure 21:
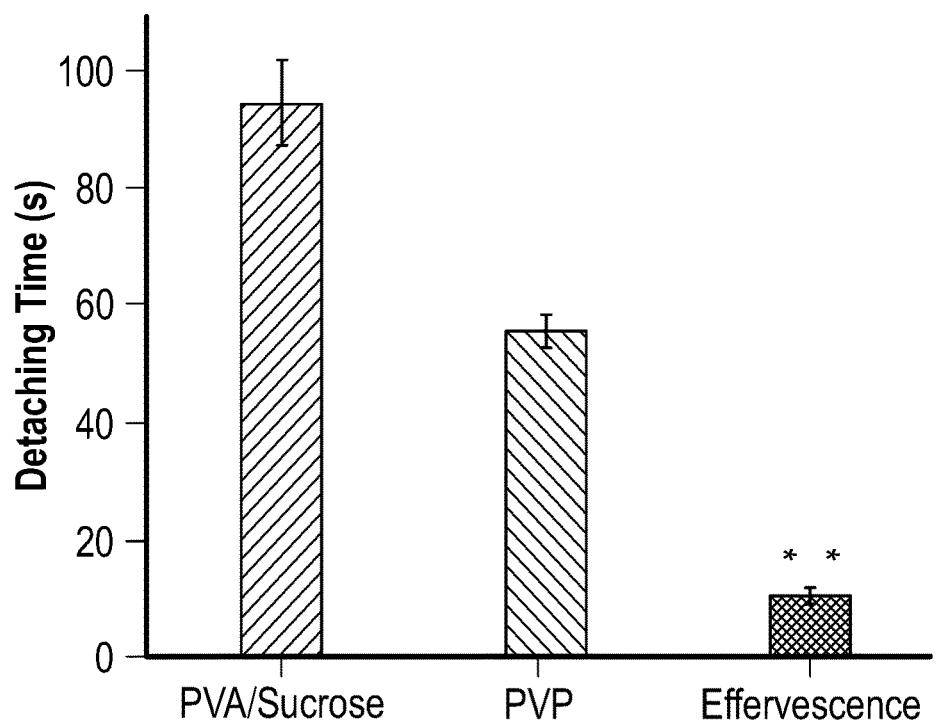
FIG. 21 is a graph depicting a quantification of detaching time for an embodiment of a microneedle patch with an effervescent backing.

To investigate whether the microneedle patches with effervescent backing of the foregoing examples could achieve rapid detachment of microneedles, the patch was immersed into phosphate buffered saline (PBS), which was used to mimic the in vivo environment. The microneedles were loaded with a fluorescent dye, Nile red, for better visualization. Bright-field microscopy images indicated that after soaking the patch in the PBS buffer, the backing part of the patch immediately generated a huge number of gas bubbles and the microneedles were rapidly separated from the patch, due at least in part to the reaction between citric acid and sodium bicarbonate and fast dissolution of the backing polymer. As depicted at FIG. 21, it took the patch with effervescent backing only 10.7±1.2 seconds to separate, compared with a detaching time of 94.0±6.6 seconds for the patch with PVP backing or 53.3±3.1 seconds for the patch with PVA/sucrose backing, demonstrating the rapid detachment of microneedles from the microneedle patch with effervescent backing.

Specifically, to assess the fast detachment of microneedle patches with effervescent backing, a single patch facing up was attached to a holder and then immersed into phosphate buffered saline (PBS) solution. A camera was used to capture the detachment process of microneedles in PBS solution with side view until all of the microneedles detached from the patch. In the control groups, detachment of microneedle patches with PVP or PVA/sucrose backing was also recorded in PBS solution.

Example 10—Skin Insertion of Microneedle Patches Ex Vivo

To determine if the microneedles patches with effervescent backing of the foregoing examples could permit rapid separation in the skin as well, the patches were applied to porcine skin in vitro. Microneedles were loaded with Nile red dye to improve visualization. The microneedle patches were pressed against the skin for 3 seconds to permit the microneedles to go into the skin, and then the patch were kept attached on the skin for another 50 seconds to permit the reaction of the effervescence backing formulation in ISF and the subsequent separation of fluorescent microneedles in the skin.

Figure 22:
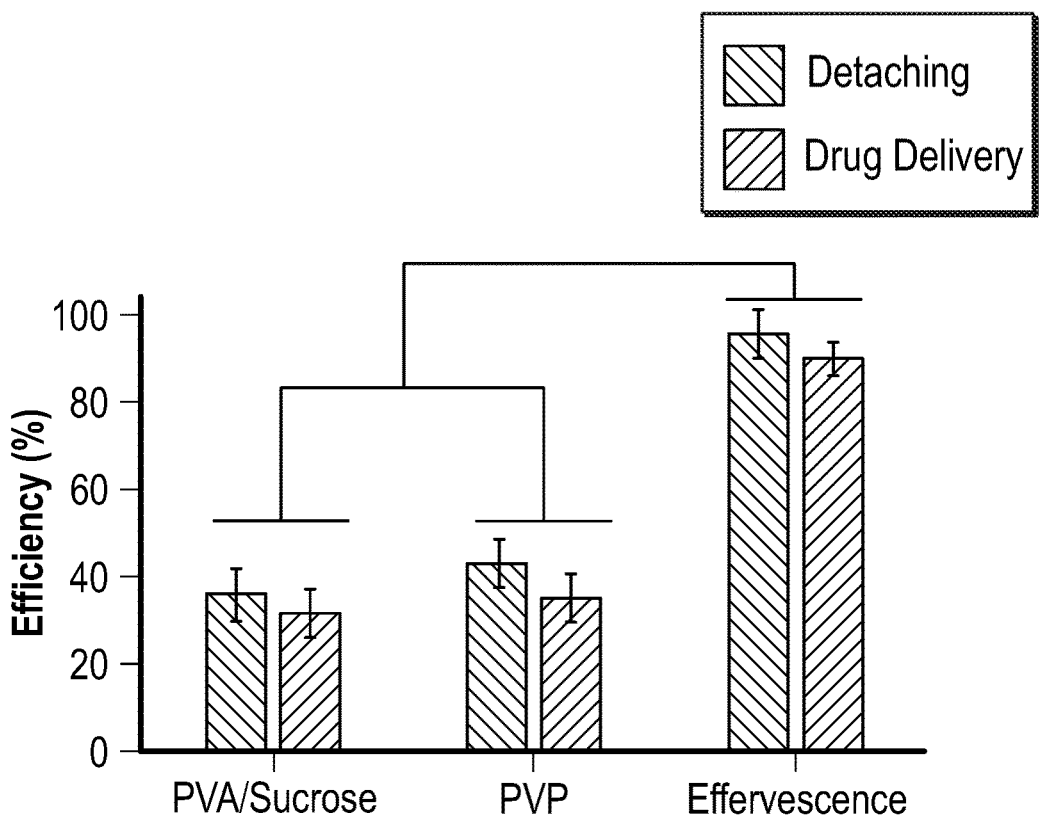
FIG. 22 is a graph depicting a quantification of the efficiency of detachment and drug delivery of an embodiment of microneedle patches having an effervescent backing.

After separation, there was very little fluorescent dye left in the residual patch, and only the dissolved backing polymer could be observed. Histological sections indicated that the separated microneedles were fully embedded. Based on the quantification depicted at FIG. 22, 100%, or nearly 100%, of the microneedles penetrated the skin, and about 96% of the microneedles were delivered into the skin after separation from the patch having an effervescent backing, and about 90.4% of the encapsulated fluorescent dye (simulating encapsulated hormone) was delivered into the skin. However, microneedle patches with PVP backing or PVA/sucrose backing only showed <45% microneedles detaching efficiency and <35% dye delivery efficiency within such a short application time on the skin. Taken together, these results evidenced successful rapid detachment of microneedles and high delivery efficiency of the patch with effervescent backing in the skin within a very short time.

Specifically, to evaluate penetration, separation, retention and delivery efficiency of microneedle patches, patches loaded with fluorescent dye (Nile Red) were inserted into stretched porcine skin ex vivo by pressing with a thumb for 10 seconds, and then leaving the patches attached to the skin for 50 seconds for full dissolution of effervescent backing and the separation of microneedles. After separation, the skin containing separated microneedles was examined by optical microscopy (Olympus, Tokyo, Japan) to identify detached microneedles embedded in the skin.

In some cases, a swab was gently and repeatedly scraped across the site of microneedle patch treatment for 10 seconds to remove any detached microneedles that were partially protruding above the skin surface. To just assess penetration of microneedle patches, patches were applied to the skin by pressing for only 5 seconds, and then immediately removed. The skin was covered with Gentian Violet solution (Humco, Linden, Tex.) for 10 min to stain sites of microneedle penetration, and then cleaned with alcohol swabs to remove residual dye from the skin surface. The penetration, separation and retention efficiency were calculated by dividing the number of colored spots (i.e., due to Gentian violet staining or presence of fluorescent microneedles in the skin) by the number of microneedles in the patch (i.e., 100 microneedles).

Specifically, to evaluate delivery efficiency of the microneedle patch, fluorescence intensity from dye in the microneedle patch before and after skin insertion, as well as fluorescence from dye on the skin surface, were measured by quantitative image analysis (Microplate Reader, Bio-Rad, Hercules, Calif.). The dye delivered in the skin was quantified by subtracting the amount of dye in the residual backing and on the skin surface from that in the microneedle patch before insertion. Delivery efficiency was calculated by dividing the delivered dye in the skin by the amount of dye in the microneedle patch before insertion. Finally, skin was frozen and then cut into 10 μm sections for histological analysis.

Example 11—Levonorgestrel Release from Microneedle Patches In Vitro

Figure 23:
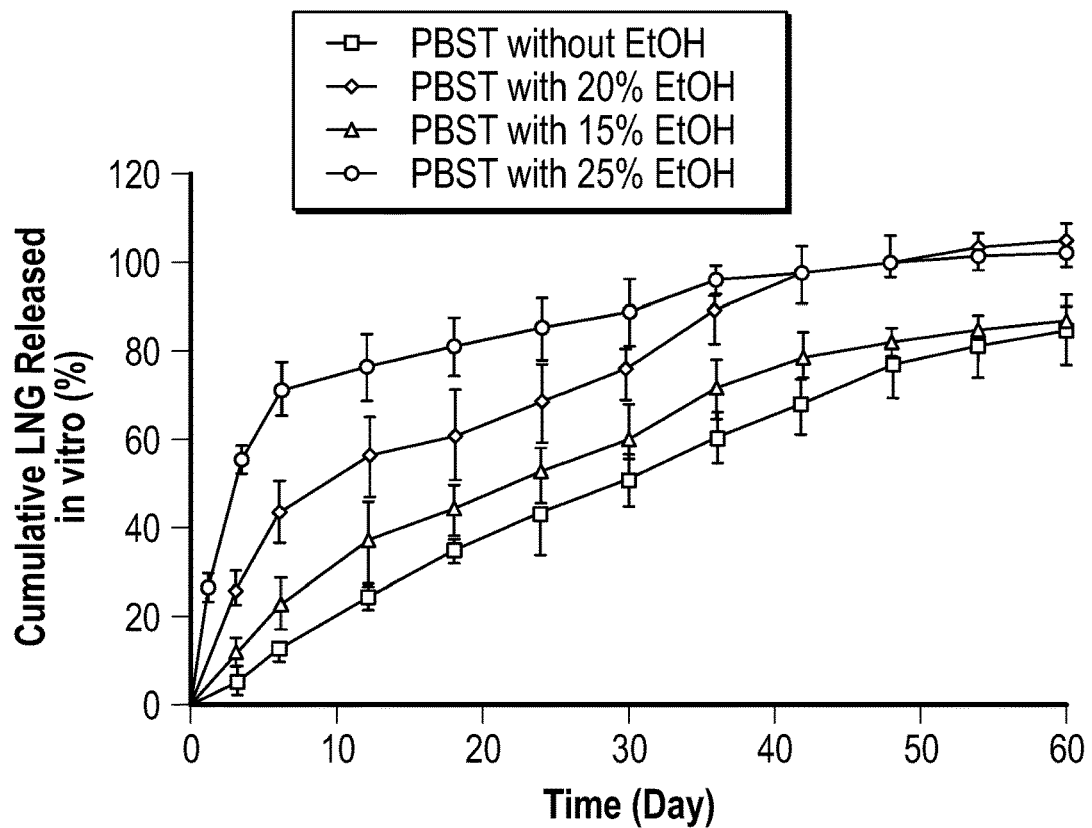
FIG. 23 is a graph depicting the cumulative amount of a contraceptive hormone released in vitro by an embodiment of a microneedle patch having an effervescent backing in different release media.

The microneedle patches with effervescent backing of the foregoing examples were further tested for the release of LNG by using a release media of saline containing 0-25% ethanol, which was added to better simulate in vivo release kinetics. Although about 25% of the LNG was released on day 1 in the medium containing 25% ethanol, as depicted at FIG. 23, there was no initial burst release of LNG in the other release mediums (i.e., medium containing 0%, 15%, 20% ethanol). The LNG release kinetics were fairly constant over time. Even though the release medium with 25% ethanol showed fastest LNG release at the rate of about 2.8% per day, it took as long as 35 days for all of the LNG to be released from the microneedle patches, which indicated that sustained release of LNG from the microneedle patches was possible, a target delivery timeframe of at least one month was achievable.

Specifically, to evaluate in vitro release of LNG from microneedle patches and predict release of LNG in vivo, PBST was used with different concentrations of ethanol as the release medium. Specifically, one microneedle patch was placed into 1 L PBST (with varying concentrations of ethanol) in a glass vessel.

The PBST solution included 137 mM NaCl, 2.68 mM KCl, 10.14 mM $Na_2HPO_4$, 1.76 mM $KH_2PO_4$, and 0.02% (w/v) Tween-80; ethanol was added to PBST to a final concentration of 0%, 2%, 10% or 25% (v/v) ethanol. The glass vessel was incubated in a shaker water bath at 37° C. and shaken at 80 rpm. At predetermined time points (0, 1, 3, 6, 12, 18, 24, 30, 36, 43, 49, 54, 60 days), 1 mL release medium was collected and replaced with the same amount of fresh medium. Collected samples were analyzed by UPLC-MS (Waters, Milford, Mass.) to quantify LNG concentration. LNG was separated on an Acquity UPLC BEH C18 column (100 mm×2.1 mm i.d., 1.7 μm particle size) at 50° C. The mobile phase was a mixture of acetonitrile containing 0.1% formic acid and water containing 0.1% formic acid (8:2 ratio, v/v). The flow rate was 0.3 mL/min with an injection volume of 10 μL. Detection of LNG was performed by electrospray ionization mass spectrometry in the positive ion mode. The target analyte of LNG (M+H$^+$; m/z=313.4) was used for quantification.

Figure 24:
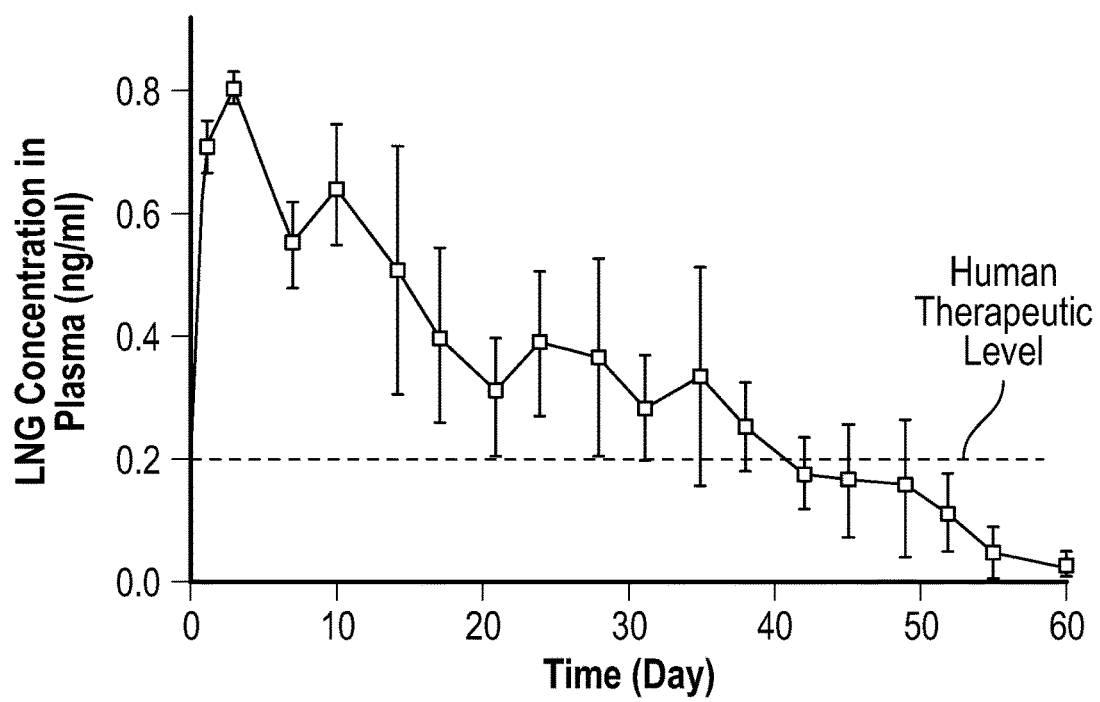
FIG. 24 is a graph depicting the concentration of a contraceptive hormone in plasma after application of an embodiment of a microneedle patch having an effervescent backing.

Example 12—Levonorgestrel Pharmacokinetics After Release from Microneedles In Vivo To test rapid detachment of microneedles and LNG pharmacokinetics from the microneedle patches with effervescent backing in vivo, the microneedle patches with effervescent backing (containing hydrophobic Nile red dye) of the foregoing examples were manually pressed against shaved rat skin in vivo for 3 seconds and then the patches remained attached on the rat skin surface for another 50 seconds for the dissolution of the effervescent backing and subsequent detachment of microneedles. The fluorescent microneedles separated from the patch after the application of the patches on rat skin for less than 1 minute (i.e. 3 seconds for pressing and 50 seconds for attaching), and the histological section demonstrated the full embedding of these microneedles in the rat skin. FIG. 24 depicts rat plasma concentration of LNG after administration of LNG-loaded microneedle patches. The therapeutic LNG level in humans is indicated by the blue dashed line. Each point represents mean±S.D. (n=10).

Specifically, LNG pharmacokinetics were evaluated in adult female Sprague Dawley rats (200±12 g) by applying a LNG-loaded microneedle patch to each rat while under isoflurane anesthesia. The rats' dorsal skin was shaved before application of microneedle patches, taking care not to damage skin during shaving.

To investigate the detachment of PLGA/LNG MNs in rats, microneedle patches containing Nile red were administered to the rats using the methods described above for ex vivo microneedle patch application to porcine skin, after which the administration sites of rats were imaged by fluorescence microscopy (Olympus).

To study pharmacokinetics of LNG release from separable microneedles, a group of 10 rats received LNG-loaded microneedle patches. A power analysis indicated that a sample size of 10 rats per group would be sufficient to distinguish pharmacokinetic profiles in animals receiving LNG from those without any application of patches with 95% confidence. The primary endpoint of the animal study was LNG plasma concentration above the human therapeutic level for one month. The secondary endpoint was irritation at the site of microneedle patch administration. All data collected in this study were retained; no outliers were excluded.

Blood samples (about 500 μL) were drawn from the tail vein at different times after microneedle patch application: 0 h, 12 h, 24 h, 3 d, 7 d, 10 d, 14 d, 17 d, 21 d, 24 d, 28 d, 31 d, 35 d, 38 d, 42 d, 45 d, 49 d, 52 d, 55 d, 60 d. Plasma was then separated by centrifuging blood samples at 2000 g for 15 minutes at 4° C., and underwent subsequent analysis by enzyme-linked immunosorbent assay (ELISA, Thermo Fisher Scientific) following the manufacturer's instruction to determine LNG concentration.

To evaluate biocompatibility of LNG delivery from separable microneedle patches, rats were euthanized by $CO_2$ asphyxiation at the end of the study (i.e., 60 days after microneedle patch application) and tissue surrounding the patch application site was excised. This tissue was fixed in 10% neutral buffered formalin for 2 days at 4° C., and then embedded in paraffin after complete dehydration, cut into sections of 5 μm thickness, and stained using hematoxylin and eosin for histological analysis.

Example 13—Microneedle Patches with Effervescent Backing in Human Study

To be eligible, participants had to be healthy non-pregnant female adults with normal skin, no known problems with pain perception and no known allergies to the materials used in this study. Ten subjects with ages from 21 to 36 were recruited.

Subjects received microneedle patches on the dorsal surface of their hands. Three subjects received two patches on both of their two hands, and others received only one patch on their left hand. The patches were applied on the subjects' hands for about 1 minute, and the skin morphology was imaged by a camera at the time of 0 h, 1 h and 24 h after patch application. For those subjects who received two microneedle patches, the application site on their right hands was stained with gentian violet and then imaged 5 minutes after staining. All subjects were required to answer a short questionnaire to solicit information about the pain of the microneedle patch administration and the acceptability of microneedle patches for delivery of drugs (e.g., contraceptives).

Figure 25:
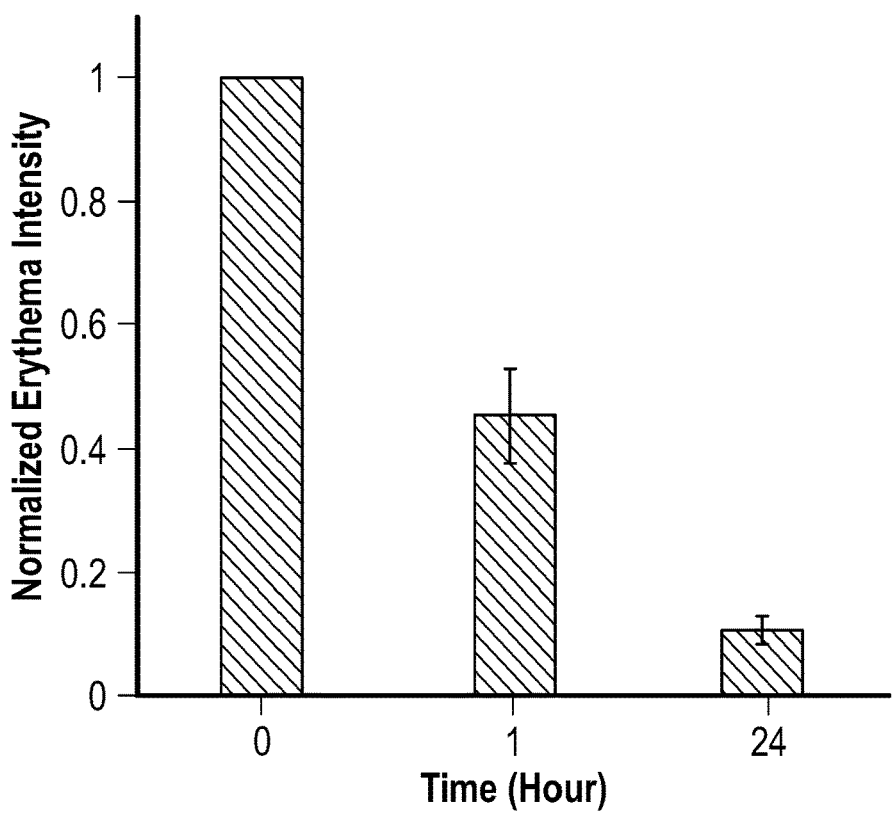
FIG. 25 is a graph depicting normalized erythema intensity after application of an embodiment of a microneedle patch having an effervescent backing.
Figure 26:
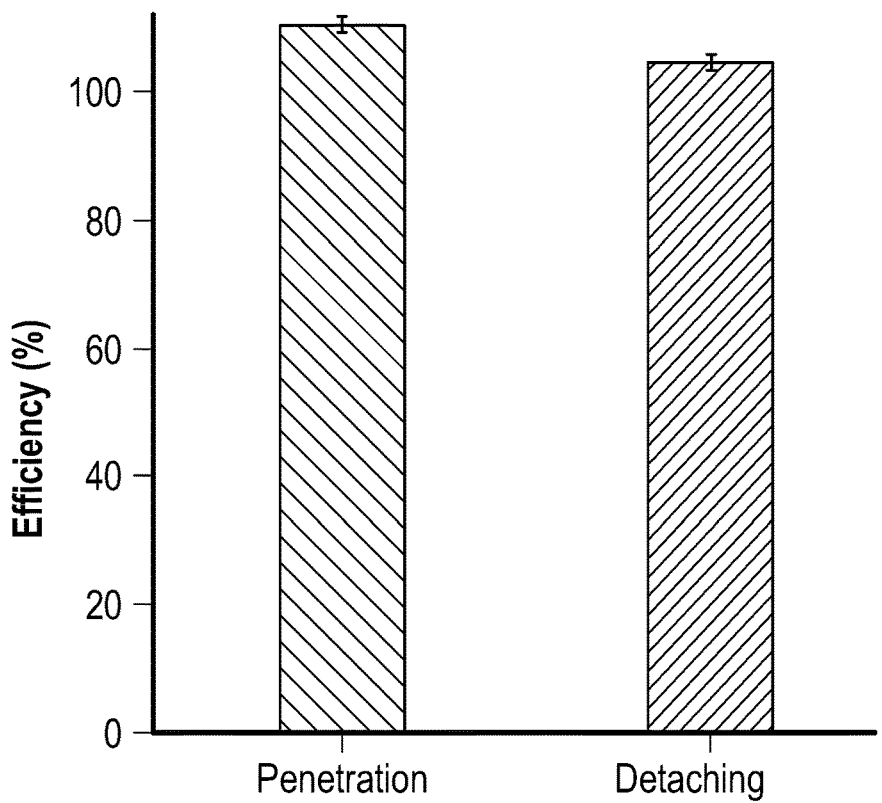
FIG. 26 is a graph depicting the efficiency of penetration and detaching for an embodiment of a microneedle patch having an effervescent backing.

FIG. 25 depicts the normalized erythema intensity of the skin site where the microneedle patches were applied over time. (n=10). FIG. 26 depicts the efficiency of penetration and detaching of the microneedle patches of this example on the subjects' skin (n=4).

Example 14—Statistical Analysis

All results presented in this study were mean±standard deviation. Statistical analysis was performed using two-sided Student's t test or an ANOVA test with the software of Origin. The probability value of less than 0.05 was considered as significant.

We claim:

1. A microneedle array for administering a substance of interest into a patient's biological tissue, the microneedle array comprising:
   a base substrate having a microneedle side and an opposing back side;
   at least one primary funnel portion extending from the microneedle side of the base substrate; and
   two or more solid microneedles extending from the at least one primary funnel portion, wherein the two or more solid microneedles comprise a substance of interest and a secondary funnel portion extending from the at least one primary funnel,
   wherein the secondary funnel portions comprise a first water soluble matrix material and an effervescent material;
   wherein the two or more solid microneedles are constructed to penetrate into the patient's biological tissue under compression and then to separate from the secondary funnel portions upon at least partial dissolution of the secondary funnel portions.

2. The microneedle array of claim 1, wherein the effervescent material comprises an acid and a salt of a base.

3. The microneedle array of claim 2, wherein the acid comprises citric acid and the salt of a base comprises sodium bicarbonate.

4. The microneedle array of claim 1, wherein the effervescent material and the first water soluble matrix material are present in the secondary funnel portions at a weight ratio of about 0.2:1 to about 1:0.2.

5. The microneedle array of claim 1, wherein the substance of interest comprises a contraceptive hormone.

6. The microneedle array of claim 5, wherein the contraceptive hormone comprises a progestin.

7. The microneedle array of claim 5, wherein the microneedle array is configured to release a therapeutically or prophylactically effective amount of the substance of interest to the patient for a sustained period of at least 2 weeks.

8. The microneedle array of claim 5, wherein the microneedle array is configured to release a therapeutically or prophylactically effective amount of the substance of interest to the patient for a sustained period of at least 4 weeks.

9. The microneedle array of claim 1, wherein the substance of interest comprises an active pharmaceutical ingredient.

10. The microneedle array of claim 1, wherein the two or more solid microneedles are formed of a composition comprising a second matrix material in which the substance of interest is dispersed.

11. The microneedle array of claim 10, wherein the second matrix material comprises poly-lactic acid, poly-lactic glycolic acid, or a combination thereof.

12. The microneedle array of claim 1, wherein the first water soluble matrix material comprises polyvinylpyrrolidone, polyvinyl alcohol, sucrose, or a combination thereof.

13. The microneedle array of claim 1, wherein the two or more microneedles have a length of about 200 µm to about 1200 µm.

14. The microneedle array of claim 1, wherein the secondary funnel portions comprise a straight, tapered sidewall.

15. A microneedle patch comprising:
the microneedle array of claim 1;
an adhesive layer; and
a handle layer affixed to the base substrate, wherein the handle layer comprises a tab portion which extends laterally away from a single side of the two or more solid microneedles and permits a person to manually hold the tab portion to manipulate the patch without contacting the two or more solid microneedles.

16. A microneedle array for administering a substance of interest into a patient's biological tissue, the microneedle array comprising:
a base substrate having a microneedle side and an opposing back side;
at least one primary funnel portion extending from the microneedle side of the base substrate; and
two or more solid microneedles extending from the at least one primary funnel portion, wherein the two or more solid microneedles comprise a substance of interest and a secondary funnel portion extending from the at least one primary funnel;
wherein the two or more solid microneedles are configured to (i) penetrate into the patient's biological tissue under compression and then to separate from the secondary funnel portions, and (ii) release a therapeutically or prophylactically effective amount of the substance of interest to the patient for a sustained period of at least 2 weeks, and
wherein the substance of interest comprises a contraceptive hormone, and
wherein (i) the two or more solid microneedles comprise a bubble structure at or near a base end of each microneedle, the bubble structures facilitating the separation of the microneedles from the secondary funnel portions, or (ii) the secondary funnel portions comprise a first water soluble matrix material and an effervescent material configured to increase a rate at which the first matrix material dissolves upon contacting a biological fluid beneath the biological tissue, thereby facilitating the separation of the microneedles from the secondary funnel portions.

17. The microneedle array of claim 16, wherein the contraceptive hormone comprises a progestin.

18. The microneedle array of claim 16, wherein the microneedle array is configured to release the therapeutically or prophylactically effective amount of the substance of interest to the patient for a sustained period of at least 4 weeks.

19. The microneedle array of claim 16, wherein the two or more solid microneedles are formed of a composition comprising a second matrix material in which the contraceptive hormone is dispersed.

20. The microneedle array of claim 19, wherein the second matrix material comprises poly-lactic acid, poly-lactic glycolic acid, or a combination thereof.

21. The microneedle array of claim 16, wherein the two or more microneedles have a length of about 200 µm to about 1200 µm.

22. The microneedle array of claim 16, wherein the secondary funnel portions comprise a straight, tapered sidewall.

23. A microneedle patch comprising:
the microneedle array of claim 16;
an adhesive layer; and
a handle layer affixed to the base substrate, wherein the handle layer comprises a tab portion which extends laterally away from a single side of the two or more solid microneedles and permits a person to manually hold the tab portion to manipulate the patch without contacting the two or more solid microneedles.

24. A microneedle array for administering a substance of interest into a patient's biological tissue, the microneedle array comprising:
a base substrate having a microneedle side and an opposing back side;
a primary funnel portion extending from the microneedle side of the base substrate; and
one or more solid microneedles extending from the primary funnel portion, wherein at least a tip end portion of each microneedle comprises a substance of interest,
wherein an effervescent material is disposed in the primary funnel portion and/or in a base end of each microneedle, in an amount effective to cause the microneedles to separate from the primary funnel portion following insertion of the one or more microneedles into the biological tissue and subsequent at least partial dissolution of the primary funnel portion and/or base end of the microneedle.

25. The microneedle array of claim 24, which is configured to provide the separation of the microneedles from the primary funnel portion within 60 seconds following insertion of the microneedles into a patient's skin.

26. The microneedle array of claim 25, wherein the inserted and separated microneedles provide controlled release of the substance of interest for at least 2 weeks following the insertion.

27. The microneedle array of claim 24, wherein the substance of interest comprises a contraceptive hormone.

28. The microneedle array of claim 27, wherein the contraceptive hormone comprises a progestin.

29. The microneedle array of claim 24, wherein the substance of interest comprises an active pharmaceutical ingredient.

30. The microneedle array of claim 29, wherein the microneedle array is configured to release a therapeutically or prophylactically effective amount of the substance of interest to the patient for a sustained period of 2 to 4 weeks.

31. The microneedle array of claim 30, wherein the substance of interest comprises a contraceptive hormone.

32. The microneedle array of claim 31, wherein the contraceptive hormone comprises a progestin.

33. A microneedle array for administering a substance of interest into a patient's biological tissue, the microneedle array comprising:

- a base substrate having a microneedle side and an opposing back side; and
- two or more solid microneedles extending from the base substrate, wherein at least a tip end portion of each microneedle comprises a substance of interest,
- wherein an effervescent material is disposed in a portion of each of the two or more solid microneedles, at least a portion of the base substrate, or a combination thereof, and
- the two or more solid microneedles are configured to penetrate into the patient's biological tissue under compression and then to separate at least the tip end portion of each microneedle from the base substrate upon at least partial dissolution of the at least a portion of the base substrate and/or the portion of each of the two or more microneedles in which the effervescent material is disposed.

34. The microneedle array of claim 33, further comprising a primary funnel portion, wherein the effervescent material is disposed in at least a portion of the primary funnel portion.

* * * * *